United States Patent
Rovis et al.

(10) Patent No.: US 12,377,407 B2
(45) Date of Patent: *Aug. 5, 2025

(54) COMPOSITIONS AND METHODS FOR VISIBLE-LIGHT-CONTROLLED RUTHENIUM-CATALYZED OLEFIN METATHESIS

(71) Applicant: The Trustees of Columbia University in the City of New York, New York, NY (US)

(72) Inventors: Tomislav Rovis, Scarsdale, NY (US); Cedric Theunissen, New York, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 17/691,257

(22) Filed: Mar. 10, 2022

(65) Prior Publication Data

US 2022/0219155 A1    Jul. 14, 2022

Related U.S. Application Data

(63) Continuation of application No. 16/597,231, filed on Oct. 9, 2019, now Pat. No. 11,331,656.

(60) Provisional application No. 62/743,509, filed on Oct. 9, 2018.

(51) Int. Cl.
| | | |
|---|---|---|
| B01J 31/30 | (2006.01) | |
| B01J 31/02 | (2006.01) | |
| B01J 31/22 | (2006.01) | |
| B01J 35/39 | (2024.01) | |
| C07C 6/04 | (2006.01) | |
| C07C 6/06 | (2006.01) | |

(52) U.S. Cl.
CPC ....... *B01J 31/2273* (2013.01); *B01J 31/0275* (2013.01); *B01J 31/2291* (2013.01); *B01J 35/39* (2024.01); *C07C 6/04* (2013.01); *C07C 6/06* (2013.01); *B01J 2231/543* (2013.01); *B01J 2531/821* (2013.01); *C07C 2531/22* (2013.01)

(58) Field of Classification Search
None
See application file for complete search history.

(56) References Cited

U.S. PATENT DOCUMENTS

2017/0240695 A1* 8/2017 Boydston ............. C08G 61/125
2019/0232267 A1* 8/2019 Burtovyy ............. B01J 31/2273

FOREIGN PATENT DOCUMENTS

WO    2019/147878 A1    8/2019

OTHER PUBLICATIONS

Vorfalt et al. (Angew. Chem., Int. Ed., 2009, 48, 5191-5194). (Year: 2009).*

(Continued)

*Primary Examiner* — Yun Qian
(74) *Attorney, Agent, or Firm* — BakerHostetler

(57) ABSTRACT

The present disclosure provides compositions and methods for metathesizing a first alkenyl or alkynyl group with a second alkenyl or alkynyl group, the composition comprising a ruthenium metathesis catalyst and a photoredox catalyst that is activated by visible light.

14 Claims, 19 Drawing Sheets

(56) References Cited

OTHER PUBLICATIONS

Anastasaki et al., "Copper(II)/Tertiary Amine Synergy in Photoinduced Living Radical Polymerization: Accelerated Synthesis of ?- Functional and a,?- Heterofunctional Poly(acrylates)", J. Am. Chem. Soc., 2014, 136, 1141-1149.
Antoni et al., "Pyrylenes: A New Class of Tunable, Redox-Switchable, Photoexcitable Pyrylium-Carbene Hybrids with Three Stable Redox-States", J. Am. Chem. Soc., 2018, 140, 14823-14835.
Bailey et al., "Confronting Neutrality: Maximizing Success in the Analysis of Transition-Metal Catalysts by MALDI Mass Spectrometry", ACS Catal., 2016, 6, 4962-4971.
Bantreil, "Synthesis of N-heterocyclic carbene ligands and derived ruthenium olefin metathesis catalysts", Nat. Protoc., 2011, 6, 69-77.
Ben-Asuly et al., "Photoactivation of Ruthenium Olefin Metathesis Initiators", Organometallics, 2009, 28, 4652-4655.
Blanco, "Artificial switchable catalysts", Chem. Soc. Rev. 2015, 44, 5341-5370.
Branchi et al., "The Role of Aromatic Radical Cations and Benzylic Cations in the 2,4,6-Triphenylpyrylium Tetrafluoroborate Photosensitized Oxidation of Ring-Methoxylated Benzyl Alcohols in CH2Cl2", J. Org. Chem., 2004, 69, 8874-8885.
Bratton et al., "Recent progress in high resolution lithography", Polym. Adv. Technol., 2006, 17, 94-103.
Broggi et al., "The Influence of Phosphane Ligands on the Versatility of Ruthenium-Indenylidene Complexes in Metathesis", Chem. Eur. J., 2010, 16, 9215-9225.
Bunnage et al., "An Expeditious Asymmetric Synthesis of Allophenylnorstatine", Tetrahedron, 1994, 50, 3975-3986.
Busque et al., "Synthesis of Some New Highly Functionalized C6-Synthons", Tetrahedron, 1995, 51, 1503-1508.
Chen, "Light-Controlled Radical Polymerization: Mechanisms, Methods, and Applications", Chem. Rev., 2016, 116, 10167-10211.
Choudhury, "Recent developments on artificial switchable catalysis", Tetrahedron Lett., 2018, 59, 487-495.
Conrad et al., "Concise Route to Highly Reactive Ruthenium Metathesis Catalysts Containing a Labile Donor and an N-Heterocyclic Carbene (NHC) Ligand", Organometallics, 2003, 22, 1986-1988.
Cunico, "The Diels-Alder Reaction of Alpha, Beta-Unsaturated Trihalosilanes with Cyclopentadiene", J. Org. Chem., 1971, 36, 929-932.
Eelman et al., "Shining New Light on an Old Problem: Retooling MALDI Mass Spectrometry for Organotransition-Metal Catalysis", Angew. Chem. Int. Ed., 2008, 47, 303-306.
Eivgi et al., "Bichromatic Photosynthesis of Coumarins by UV Filter-Enabled Olefin Metathesis", Advanced Synthesis & Catalysis, Jul. 2017, 359, 14, 2352-2357.
Eivgi et al., "Turning the Light on: Recent Developments in Photoinduced Olefin Metathesis", Synthesis, 2018, 50, 49-63.
Fors et al., "Control of a living radical polymerization of methacrylates by light", Angew. Chem. Int. Ed., 2012, 51, 8850-8853.
Fürstner et al., "Comparative Investigation of Ruthenium-Based Metathesis Catalysts Bearing N-Heterocyclic Carbene (NHC) Ligands", Chem. Eur. J., 2001, 7, 3236-3253.
Goetz et al., "Metal-Free Preparation of Linear and Cross-Linked Polydicyclopentadiene", J. Am. Chem. Soc., 2015, 137, 7572-7575.
Goetz, "Expanded Functionality of Polymers Prepared Using Metal-Free Ring-Opening Metathesis Polymerization", ACS Macro Lett. 2016, 5, 579-582.
Gostl et al., "Remote-controlling chemical reactions by light: Towards chemistry with high spatio-temporal Resolution", Chem. Soc. Rev. 2014, 43, 1982-1996.
Harris et al., "Photolithographic Patterning of Ring-Opening Metathesis Catalysts on Silicon", Adv. Mater., 2005, 17, 39-42.
Hata et al., "Iron-Mediated Intramolecular Metalative Cyclization of Alpha, Beta-Unsaturated Esters and Amides. Versatile One-Pot Preparation of Bicyclic Ketoesters", Org. Lett., 2008, 10, 5031-5033.
Henderson et al., "Allylic Oxidations of Terminal Olefins Using a Palladium Thioether Catalyst", Org. Lett., 2010, 12, 824-827.
Higman et al., "Olefin Metathesis at the Dawn of Implementation in Pharmaceutical and Specialty-Chemicals Manufacturing", Angew. Chem. Int. Ed., 2016, 55, 3552-3565.
Hongfa et al., "Heptane-Soluble Ring-Closing Metathesis Catalysts", Org. Lett., 2007, 9, 3259-3261.
Hoveyda et al., "The remarkable metal-catalysed olefin metathesis reaction", Nature 2007, 450, 243-250.
Huang et al., "Olefin Metathesis-Active Ruthenium Complexes Bearing a Nucleophilic Carbene Ligand", J. Am. Chem. Soc., 1999, 121, 2674-2678.
Jafarpour et al., "Simple and Convenient Synthetic Procedure Leading to Ruthenium Olefin Metathesis Catalysts Bearing the N,N¢-Bis(mesityl)imidazol-2-ylidene (IMes) Ligand", Organometallics, 2000, 19, 2055-2057.
Katz et al., "Olefin Metatheses and Related Reactions Initiated by Carbene Derivatives of Metals in Low Oxidation States", Angew. Chem. Int. Ed., 2005, 44, 3010-3019.
Keitz et al., "A Tandem Approach to Photoactive Metathesis: Combining a Photoacid Generator with an Acid Activated Catalyst", J. Am. Chem. Soc., 2009, 131, 2038-2039.
Khalimon et al., "Photogeneration of a Phosphonium Alkylidene Olefin Metathesis Catalyst", Organometallics, 2012, 31, 5634-5637.
Khalimon et al., Photogeneration of a Phosphomium Alkylidene Olefin Metethesis Catalyst, Organometallics, 2012, 5634-5637.
Kotyk et al., "Geometric and Electronic Structure of a C1-Symmetric Ruthenium-Aryloxide Metathesis Catalyst: An Experimental and Computational Study", Organometallics, 2009, 28, 5424-5431.
Leibfarth et al., "External Regulation of Controlled Polymerizations", Angew. Chem. Int. Ed. 2013, 52, 199-210.
Levin et al., "Regioselective Chromatic Orthogonality with Light-Activated Metathesis Catalysts", Angew. Chem. Int. Ed., 2015, 54, 12384-12388.
Li et al., "Pd-Catalyzed Olefination of Perfluoroarenes with Allyl Esters", Org. Let, 2012, 14, 74-77.
Lipschutz et al., "TPGS-750-M: A Second-Generation Amphiphile for Metal-Catalyzed Cross-Couplings in Water at Room Temperature", J. Org. Lett., 2011, 76, 4379-4391.
Lu et al., "Bidirectional Metal-Free ROMP from Difunctional Organic Initiators", Journal of Polymer Science, Part A: Polymer Chemistry, 2017, 55, 2977-2982.
Monsaert et al., "Latent olefin metathesis catalysts", Chem. Soc. Rev., 2009, 38, 3360-3372.
Munoz et al., "New Platinum-Catalysed Dihydroalkoxylation of Allenes", Adv. Synth. Catal., 2010, 352, 2189-2194.
Neilson et al., "Illuminating Photoswitchable Catalysis", ACS Catal., 2013, 3, 1874-1885.
Ogawa et al., "Developments in Externally Regulated Ring-Opening Metathesis Polymerization", Synlett, 2016, 27, 203-214.
Ogawa, "Metal-Free Ring-Opening Metathesis Polymerization", J. Am. Chem. Soc., 2015, 137, 1400-1403.
Ogba et al., "Recent advances in ruthenium-based olefin metathesis", Chem. Soc. Rev., 2018, 47, 4510-4544.
Pan et al., "Photoinduced Atom Transfer Radical Polymerization with ppm-Level Cu Catalyst by Visible Light in Aqueous Media", J. Am. Chem. Soc., 2015, 137, 15430-15433.
Pascual et al., "Comparison of Pyrlium and Thiopyrylium Photooxidants in Met-al-Free Ring-Opening Metathesis Polymerization", Synlett, 2016, 27, 759-762.
Pascual et al., "Investigation of Tacticity and Living Characteristics of Photoredox-Mediated Metal-Free Ring-Opening Metathesis Polymerization", Macromolecular Rapid Communications, 2017, 38, 1600766, 6 pages.
U.S. Appl. No. 16/597,231, filed Oct. 9, 2019.
Piers et al. Organometallics, 2012, 31, 5634-5637 (Year: 2012).
Polyzos et al., "Two-photon absorption properties of novel organic materials for three-dimensional optical memories", Chemical Physics Letters, 2003, 369, 264-268.
Prier et al., "Visible Light Photoredox Catalysis with Transition Metal Complexes: Applications in Organic Synthesis", Chem. Rev. 2013, 113, 5322-5363.

(56) References Cited

OTHER PUBLICATIONS

Ramnial et al., "Reactions of N-heterocyclic carbenes (NHCs) with one-electron oxidants: possible formation of a carbene cation radical", Chem. Commun., 2004, 1054-1055.
Ravetz et al., "External Regulation of Cobalt-Catalyzed Cycloaddition Polymerization with Visible Light", ACS Catal., 2018, 8, 5323-5327.
Ravetz et al., "Photoinduced Ligand-to-Metal Charge Transfer Enables Photocatalyst-Independent Light-Gated Activation of Co(II)", ACS Catal., 2019, 9, 200-204.
Romero et al., "Organic Photoredox Catalysis", Chem. Rev., 2016, 116, 10075-10166.
Rühe, "And There Was Light: Prospects for the Creation of Micro- and Nanostructures through Maskless Photolithography", ACSNano, 2017, 11, 8537-8541.
Ruhl et al., "Visible Light-Gated Cobalt Catalysis for a Spatially and Temporally Resolved [2+2+2] Cycloaddition", J. Am. Chem. Soc., 2015, 138, 15527-15530.
Samojlowicz et al., "Ruthenium-Based Olefin Metathesis Catalysts Bearing N-Heterocyclic Carbene Ligands", Chem. Rev., 2009, 109, 3708-3742.
Sanford et al., "A Versatile Precursor for the Synthesis of New Ruthenium Olefin Metathesis Catalysts", Organometallics, 2001, 20, 5314-5318.
Skubi et al., "Dual Catalysis Strategies in Photochemical Synthesis", Chem. Rev., 2016, 116, 10035-10074.
Stoll et al., "Artificial Light-Gated Catalyst Systems", Angew. Chem. Int. Ed., 2010, 49, 5054-5075.
Sutar et al., "A Light-Activated Olefin Metathesis Catalyst Equipped with a Chromatic Orthogonal Self-Destruct Function", Angew. Chem. Int. Ed., 2016, 55, 764-767.
Szadkowska et al., "Initiation at Snail's Pace: Design and Applications of Latent Olefin Metathesis Catalysts Featuring Chelating Alkylidene Ligands", Curr. Org. Chem., 2008, 12, 1631-1647.
Teator et al., "A Photoswitchable Olefin Metathesis Catalyst", Organometallics 2017, 36, 490-497.
Teator et al., "Switchable Polymerization Catalysts", Chem. Rev. 2016, 116, 1969-1992.
Teator, J. Polym. Sci. Pol. Chem. 2017, 55, 2949-2960.
Tellis, Acc. Chem. Res. 2016, 49, 1429-1439.
Theunissen et al., "Visible-Light-Controlled Ruthenium-Catalyzed Olefin Metathesis", J. Am. Chem. Soc., 2019, 141, 6791-6796.
Tomar et al., "Photochemical Activation of SF6 by N-Heterocyclic Carbenes to Provide a Deoxyfluorinating Reagent", Chem. Commun., 2018, 54, 9753-9756.
Treat et al., "Metal-Free Atom Transfer Radical Polymerization", J. Am. Chem. Soc., 2014, 136, 16096-16101.
Trnka et al., "Synthesis and Activity of Ruthenium Alkylidene Complexes Coordinated with Phosphine and N-Heterocyclic Carbene Ligands", J. Am. Chem. Soc., 2003, 125, 2546-2558.
Trnka et al., "The Development of L2X2RudCHR Olefin Metathesis Catalysts: An Organometallic Success Story", Acc. Chem. Res., 2001, 34, 18-29.
Vidavsky et al., "Light-induced olefin metathesis", J. Org. Chem., 2010, 6, 1106-1119.
Wang et al., "Cationic versus Neutral RuII N-HeteroACHTUNGTRENUNGcyclic Carbene Complexes as Latent Precatalysts for the UV-Induced Ring-Opening Metathesis Polymerization", Chem. Eur. J., 2010, 16, 12928-12934.
Wang et al., "Cu(I) ToI-BINAP-Catalyzed Enantioselective Michael Reactions of Grignard Reagents and Unsaturated Esters", J. Am. Chem. Soc., 2007, 129, 276-277.
Wang et al., "Cationic RuII Complexes with N-Heterocyclic Carbene Ligands forUVInduced Ring-Opening Metathesis Polymerization", Angew. Chem. Int. Ed. 2008, 47, 3267-3270.
Weitekamp et al., "Photolithographic Olefin Metathesis Polymerization", J. Am. Chem. Soc., 2013, 135, 16817-16820.
Weskamp et al., "A Novel Class of Ruthenium Catalysts for Olefin Metathesis", Chem. Int. Ed. 1998, 37, 2490-2492.
Wu et al., "Synthesis of Pyrimidine-Modified NHC Ruthenium-Alkylidene Catalysts and Their Application in RCM, CM, EM and ROMP Reactions", Eur. J. Org. Chem., 2012, 6777-6784.
Xi et al., Analogs of Grubbs' Second Generation Catalyst with Hydrophilic Phosphine Ligands: Phase Transfer Activation of Ring Closing Alkene Metathesis, Org. Lett., 2011, 13, 6188-6191.
Xu et al. In pursuit of Moore's Law: polymer chemistry in action, Polymer J., 2018, 50, 45-55.
Yao et al., "Poly(fluoroalkyl acrylate)-Bound Ruthenium Carbene Complex:? A Fluorous and Recyclable Catalyst for Ring-Closing Olefin Metathesis", J. Am. Chem. Soc., 2004, 126, 74-75.

* cited by examiner

Before wash with DCM

After wash with DCM

Right after irradiation      5 hours after irradiation

Right after irradiation      5 hours after irradiation

Right after irradiation      5 hours after irradiation

Right after irradiation      5 hours after irradiation

- 5-ethylidene-2-norbornene
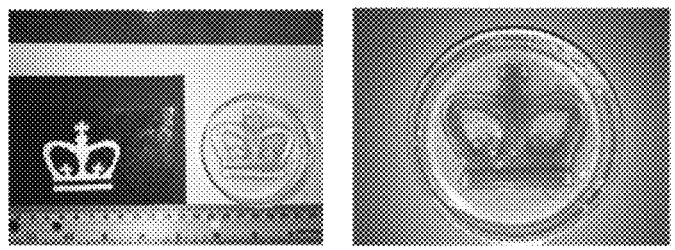
Right after irradiation    5 hours after irradiation
FIG. 28A
- Dicyclopentadiene
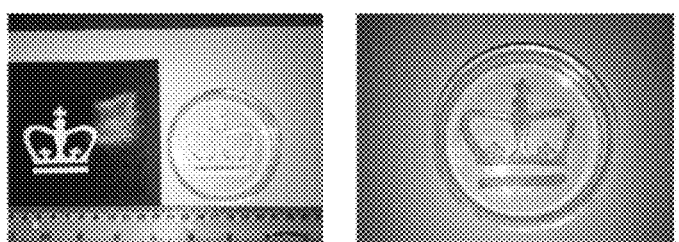
Right after irradiation    5 hours after irradiation
FIG. 28B
- Dicyclopentadiene
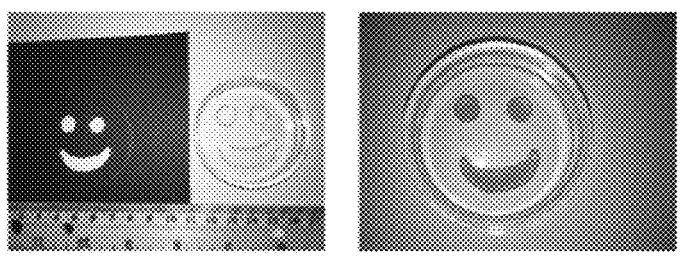
Right after irradiation    5 hours after irradiation
FIG. 28C
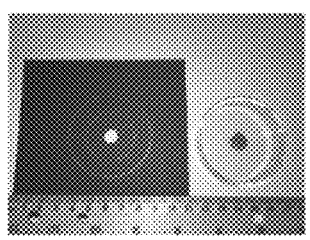 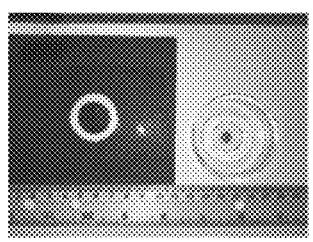 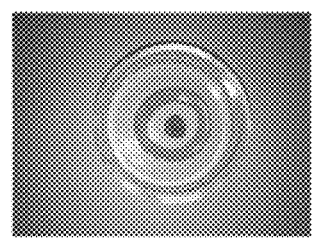
1st polymerization    2nd polymerization    5 hours after 2nd polymerization
FIG. 29A    FIG. 29B    FIG. 29C

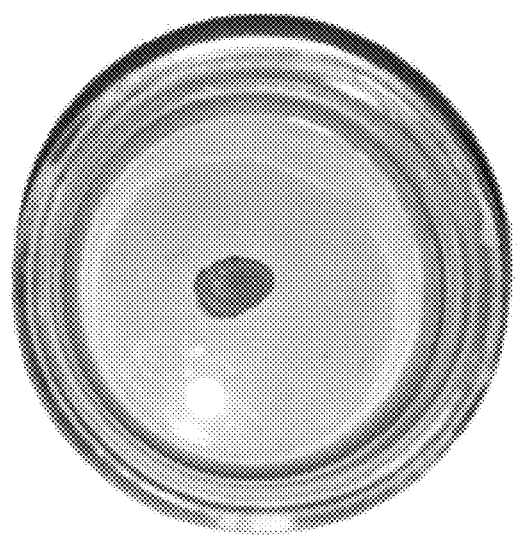 
FIG. 30A                                    FIG. 30B

COMPOSITIONS AND METHODS FOR VISIBLE-LIGHT-CONTROLLED RUTHENIUM-CATALYZED OLEFIN METATHESIS

CROSS-REFERENCE TO RELATED APPLICATIONS

This application is a divisional of U.S. patent application Ser. No. 16/597,231, filed Oct. 9, 2019, now U.S. Pat. No. 11,331,656, issued May 17, 2022, which claims the benefit of U.S. Provisional Patent Application No. 62/743,509, filed Oct. 9, 2018, which foregoing applications are incorporated by reference herein in their entireties for any and all purposes.

GOVERNMENT RIGHTS

This invention was made with government support under GM125206 awarded by the National Institutes of Health. The government has certain rights in the invention.

FIELD OF INVENTION

The present invention provides, inter alia, compositions and methods for controllable olefin metathesis.

BACKGROUND OF THE INVENTION

Controlling polymer chain length and the average molecular weight dispersity is important for production of highly functional polymers at industrial scales. Ring-opening metathesis polymerization (ROMP) is an efficient polymerization method used to manufacture polymers with high fidelity and accuracy. The ring opening metathesis polymerization (ROMP) of alkenes is an important class of chain-growth polymerization that produces industrially important products. The driving force of these reactions is the relief of ring strain in cyclic olefins and a variety of heterogeneous and homogeneous catalysts have been developed and used in this context. ROMP is an attractive method to synthesize functional polymers as it is robust, produces linear materials with narrow molecular weight distributions and controlled average molecular weights. However, ROMP is typically activated by metal catalysts that can make controlling chain length and molecular weight challenging.

As such, there is an unmet need for methods and compositions that precisely tune catalysis of ROMP, which would enable improved control of polymer production. The present disclosure is meant to address these limitations.

SUMMARY OF THE INVENTION

In some embodiments, the disclosure provides compositions for metathesizing a first alkenyl or alkynyl group with a second alkenyl or alkynyl group, the composition comprising a ruthenium metathesis catalyst and a photoredox catalyst that is activated by visible light. In certain aspects, the visible light has a wavelength of about 350 nm to about 750 nm.

In other embodiments, the disclosure provides methods of spatially controlling a metathesis, comprising forming a mixture of a ruthenium metathesis catalyst, a photoredox catalyst, and one or more compounds susceptible to metathesis; and applying visible light to one or more regions of the mixture so as to give rise to one or more metathesized regions and one or more unmetathesized regions. In certain aspects, the visible light is applied using a high resolution light source. In other aspects, at least one of the unmetathesized regions is covered with a photomask. In further aspects, the photomask is substantially opaque. In yet other aspects, the substrate is functionalized with the one or more compounds susceptible to metathesis.

The disclosed technology has application in a broad range of fields, including, e.g., polymer production, polymer patterning, photolithography and 3-D printing, among others. The disclosed technology presents numerous advantages over existing approaches, which advantages include, for example, minimal reagent requirements, the ability to use visible light (thereby reducing or even eliminating the need for more complicated illumination sources), the ability to utilize a broad range of starting materials as to arrive at a broad range of products, and the ability to exert both temporal and spatial control over product formation.

BRIEF DESCRIPTION OF THE DRAWINGS

The present application is further understood when read in conjunction with the appended drawings. For the purpose of illustrating the subject matter, exemplary embodiments of the subject matter are shown in these drawings; however, the presently disclosed subject matter is not limited to the specific methods, devices, and systems disclosed. In addition, the drawings are not necessarily drawn to scale. In the drawings:

FIG. 24A is a photograph of poly(dicyclopentadiene 12). FIG. 24B is a photograph of poly(norbornadiene 9).

FIG. 24C is a photograph of poly(1,5-cyclooctadiene 10). FIG. 24D is a photograph of poly(5-ethylidene-2-norbornene 11).

FIG. 25A is a photograph obtained after 5 minutes of irradiation. FIG. 25B is a photograph obtained after 15 minutes of irradiation. FIG. 25C is a photograph obtained after 60 minutes of irradiation.

FIG. 26A is before the wash with dichloromethane and FIG. 26B is after the wash.

FIGS. 28A-28C are photographs of the ROMP of 5-ethylidene-2-norbornene (FIG. 28A) and dicyclopentadiene (FIGS. 28B and 28C). Photographs on the left are immediately after irradiation and photographs on the right are 5 hours after irradiation.

FIGS. 29A-29C are photographs of the ROMP using sequential patterning. FIG. 29A is a photograph after a first polymerization using a first mask. FIG. 29B is a photograph after the second polymerization using a second mask. FIG. 29C is a photograph 5 hours after the second polymerization.

FIGS. 30A and 30B are photographs of the ROMP of dicyclopentadiene using blue-light laser pointer instead of Kessil lamps.

DETAILED DESCRIPTION OF ILLUSTRATIVE EMBODIMENTS

Figure 1:
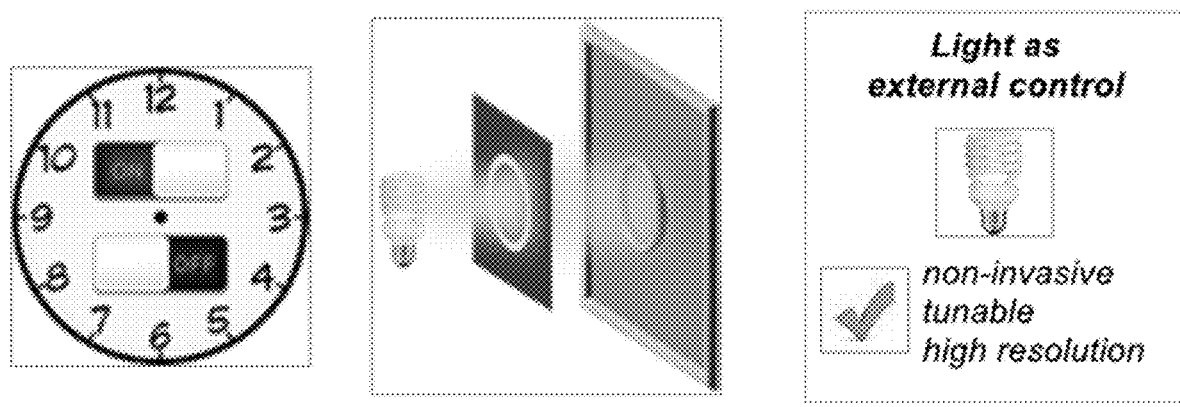
FIG. 1 is a schematic showing temporal and spatial control in catalysis.

The present invention may be understood more readily by reference to the following description taken in connection with the accompanying Figures and Examples, all of which form a part of this disclosure. It is to be understood that this invention is not limited to the specific products, methods, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer to compositions and methods of making and using said compositions. That is, where the disclosure describes or claims a feature or embodiment associated with a composition or a method of making or using a composition, it is appreciated that such a description or claim is intended to extend these features or embodiment to embodiments in each of these contexts (i.e., compositions, methods of making, and methods of using).

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such the combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially of" For those embodiments provided in terms of "consisting essentially of" the basic and novel characteristic(s) is the facile operability of the methods (and the systems used in such methods and the compositions derived therefrom) to prepare and use the inventive materials, and the materials themselves, where the methods and materials are capable of delivering the highlighted properties using only the elements provided in the claims. That is, while other materials may also be present in the inventive compositions, the presence of these extra materials is not necessary to provide the described benefits of those compositions or devices (i.e., the effects may be additive) and/or these additional materials do not compromise the performance of the product compositions or devices. Similarly, where additional steps may also be employed in the methods, their presence is not necessary to achieve the described effects or benefits and/or they do not compromise the stated effect or benefit.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C." This includes, without limitation, that a genus presenting multiple parameters, each parameter presenting multiple options, represents that collection of individual embodiments including any and every combination of these variables and options. By means of illustration only, a composition described in terms of two variables A and B, each variable presenting two options (a) and (b), includes, as independent embodiments, the subgenera A(a)–B(a), A(a)–B(b), A(b)–B(a), and A(b)–B(b). This principle can be applied to larger numbers of variables and options, such that any one or more of these variable or options can be independently claimed or excluded. Likewise, a definition such as $C_{1-3}$-alkyl includes $C_1$-alkyl, $C_2$-alkyl, $C_3$-alkyl, $C_{1-2}$-alkyl, $C_{2-3}$-alkyl, and $C_{1-3}$-alkyl as separate embodiments.

Because each individual element of a list, and every combination of that list, is a separate embodiment, it should be apparent that any description of a genus or subgenus also included those embodiments where one or more of the elements are excluded, without the need for the disclosure of the exclusion. For example, a genus described as containing elements "A, B, C, D, E, or F" also includes the embodiments excluding one or more of these elements, for example "A, C, D, E, or F;" "A, B, D, E, or F;" "A, B, C, E, or F;" "A, B, C, D, or F;" "A, B, C, D, or E;" "A, D, E, or F;" "A, B, C, or F;" "A, E, or F;" "A, C, E, or F;" "A or F;" etc., without the need to explicitly delineate the exclusions.

The term "alkyl" as used herein refers to a linear, branched, or cyclic saturated hydrocarbon group typically although not necessarily containing 1 to about 30 carbon atoms, in some cases, from 1 to about 12 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like, or in other cases from about 12 to about 24 or 30 carbon atoms (e.g., oleic and other fatty or saturated acids). Generally, although again not necessarily, alkyl groups herein can also contain 1 to about 12 carbon atoms or 1 to 6 carbon atoms. The term "cycloalkyl" intends a cyclic alkyl group, typically having 4 to 8, preferably 5 to 7, carbon atoms. The term "substituted alkyl" refers to alkyl groups substituted with one or more substituent groups, and the terms "heteroatom-containing alkyl" and "heteroalkyl" refer to alkyl groups in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl groups, respectively.

The term "haloalkyl" as used herein refers to an alkyl groups as described, wherein one or more hydrogen atom is replaced with a halo. In some embodiments, haloalkyl includes an alkyl group substituted with one or more F. In some embodiments, haloalkyl includes an alkyl group substituted with one or more Br. In some embodiments, haloalkyl includes an alkyl group substituted with one or more Cl. In some embodiments, haloalkyl includes an alkyl group substituted with one or more I. Examples of haloalkyl groups include fluorinated alkyl groups including, without limitation, $CF_3$, $CF_2H$, $CFH_2$, $CH_2CF_3$, $CH_2CH_2CF_3$, $CH_2CH_2CH_2CF_3$, and $CH_2CH_2CH_2CH_2CF_3$.

The term "alkenyl" as used herein refers to a linear, branched, or cyclic hydrocarbon group of 2 to about 30 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. In some embodiments, alkenyl groups contain 2 to about 12 carbon atoms, preferably 2 to about 6 carbon atoms. "Alkenyl" also includes vinyl groups, wherein the double bond is at a terminal location of the molecule. The term "substituted alkenyl" refers to alkenyl groups substituted with one or more substituent groups. If not otherwise indicated, the term "alkenyl" includes linear, branched, cyclic, unsubstituted, and/or substituted alkenyl groups, respectively.

The term "alkynyl" as used herein refers to a linear, branched, or cyclic hydrocarbon group of 2 to about 30 carbon atoms containing at least one triple bond, such as ethynyl, n-propynyl, isopropynyl, n-butynyl, isobutynyl, octynyl, decynyl, tetradecynyl, hexadecynyl, eicosynyl, tetracosynyl, and the like. In some embodiments, alkynyl groups contain 2 to about 12 carbon atoms, preferably 2 to about 6 carbon atoms. The term "substituted alkynyl" refers to alkynyl groups substituted with one or more substituent groups. If not otherwise indicated, the term "alkynyl" includes linear, branched, cyclic, unsubstituted, and/or substituted alkynyl groups, respectively.

The term "alkoxy" as used herein intends an alkyl group bound through a single, terminal ether linkage; that is, an "alkoxy" group may be represented as —O-alkyl where alkyl is as defined above. An "alkoxy" group includes an alkoxy group containing 1 to 6 carbon atoms, i.e., methoxy, ethoxy, propoxy, butoxy, pentoxy, or hexoxy.

The term "aryl" as used herein, and unless otherwise specified, refers to an aromatic substituent or structure containing a single aromatic ring or multiple aromatic rings that are fused together, directly linked, or indirectly linked (such that the different aromatic rings are bound to a common group such as a methylene or ethylene moiety). In some embodiments, the aryl ring is unfused. In other embodiments, the aryl is a fused aryl. In further embodiments, the aryl is a bridged aryl. Unless otherwise modified, the term "aryl" refers to carbocyclic structures. Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups.

The term "acyl" refers to substituents having the formula —(CO)-alkyl (alkylcarbonyl), —(CO)-aryl (arylcarbonyl), or —(CO)-aralkyl, and the term "acyloxy" refers to substituents having the formula —O(CO)-alkyl, —O(CO)-aryl, or —O(CO)-aralkyl, wherein "alkyl," "aryl, and "aralkyl" are as defined above.

The terms "halo," "halide," and "halogen" are used in the conventional sense to refer to a chloro, bromo, fluoro, or iodo substituent.

The term "heteroatom-containing" refers to a hydrocarbon molecule or a molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl."

Non-limiting examples of heteroaryl groups include azepinyl, acridinyl, carbazolyl, cinnolinyl, furanyl, furazanyl, furanonyl, isothiazolyl, imidazolyl, indazolyl, indolyl, isoindolyl, indolinyl, isoindolinyl, isoquinolyl, indolizinyl, isoxazolyl, naphthyridinyl, oxadiazolyl, oxazolyl, oxiranyl, phenazinyl, phenothiazinyl, phenoxazinyl, phthalazinyl, pteridinyl, purinyl, pyranyl, pyrrolyl, pyrrolidinyl, pyrazolyl, pyridinyl, pyrazinyl, pyrimidinyl, pyridazinyl, quinazolinyl, quinoxalinyl, quinolinyl, isoquinolinyl, tetrahydroquinolinyl, thiazolyl, thiadiazolyl, thiapyranyl, triazolyl, tetrazolyl, triazinyl, and thiophenyl. Non-limiting examples of heteroatom-containing alicyclic groups are pyrrolidino, morpholino, piperazino, and piperidino.

The term "aryloxy" as used herein refers to a O-aryl group, wherein the aryl group is defined herein.

The term "aralkyl" refers to an alkyl group with an aryl substituent (-alkyl-aryl), wherein aryl and alkyl are defined herein. Similarly, the term "aralkyloxy" refers to an alkyl group with a O-aryl group -alkyl-O-aryl), wherein aryl and alkyl are defined herein.

The term "acyloxy" as used herein refers to an —O-acyl, wherein acyl is defined herein. The term "acyloxy" includes groups such as alkylcarbonyloxy (—OC(O)alkyl), arylcarbonyloxy (—OC(O)aryl), alkoxycarbonyl (—C(O)Oalkyl), and aryloxycarbonyl (—C(O)Oaryl), wherein the alkyl, aryl, and alkoxy groups are defined herein.

The term "halocarbonyl" as used herein refers to the —C(O)—X, wherein X is a halo group defined herein.

The term "carboxy" refers to a —C(O)OH, carboxylato or "carboxyl" refers to a —C(O)O—, and carbamoyl refers to a —C(O)NH$_2$ group.

The terms mono-(alkyl)-substituted carbamoyl and di-(alkyl)-substituted carbamoyl refers to —C(O)NH(alkyl) and —C(O)N(alkyl)$_2$ groups, respectively, wherein the alkyl groups are defined herein and independently chosen.

The terms "mono-(aryl)-substituted carbamoyl", di-(aryl) substituted carbamoyl," and ", di-N-(alkyl),N-(aryl)-substituted carbamoyl" refer to —C(O)NH-aryl, —C(O)N(aryl)$_2$), and —C(O)N(aryl)(alkyl) groups, wherein alkyl and aryl are defined herein and independently chosen.

The term "thiocarbamoyl" refers to the —C(S)NH$_2$ group. Similarly, the terms mono-(alkyl)-substituted thiocarbamoyl refers to the —C(S)NH(alkyl)) and the di-(alkyl)-substituted thiocarbamoyl refers to the —C(S)N(alkyl)$_2$), wherein the alkyl group is defined herein and is independently selected.

The terms "mono-(aryl)substituted thiocarbamoyl" and "di-($C_{5-24}$aryl)-substituted thiocarbamoyl" refers to —C(S) NH-aryl and —C(S)N($C_{5-24}$aryl)$_2$ groups, wherein the aryl groups are defined herein and are independently chosen.

The term "amino" refers to the NH$_2$ group. Similarly, alkyl-substituted amino groups include "mono-(alkyl)-substituted amino" and di-(alkyl)-substituted amino, wherein the alkyl groups are defined herein and independently chosen. Further, aryl-substituted amino groups include mono-(aryl)substituted amino and di-(aryl)-substituted amino, wherein the aryl groups are defined herein and independently chosen.

The term "amido" refers to the —NHC(O)— group, and includes alkylamido and arylamido groups. The terms "alkylamido" and "arylamido" refers to —NHC(O)alkyl and —NHC(O)aryl, wherein alkyl and aryl are defined herein.

The terms "alkylthio" and "arylthiol" as used herein refer to —S-alkyl and —S-aryl, groups, respectively, wherein alkyl and aryl are defined herein.

The term "sulfonyl" refers to the SO$_2$ group.

The term "germyl" refers to a GeR$^Z_3$ group, the term "stannyl" refers to a SnR$^Z_3$ group, the term "boryl" refers to a BH$_2$, BH(R$^Z$), B(R$^Z$)$_2$, or B(OR$^Z$)$_2$, group, and "silyl" refers to a SiR$^Z_3$, wherein R$^Z$ is, independently, in each instance $C_{1-12}$alkyl or aryl as defined herein.

By "substituted" as in "substituted alkyl," "substituted aryl," and the like, as alluded to in some of the aforementioned definitions, is meant that in the alkyl, aryl, heteroaryl, or other moiety, at least one hydrogen atom bound to a carbon (or other) atom is replaced with one or more non-hydrogen substituents. Examples of such substituents include, without limitation, halo (e.g., F, Cl, Br, I), OH, sulfhydryl, alkoxy, aryloxy, aralkyloxy, acyl (including alkylcarbonyl, arylcarbonyl, acyloxy (alkylcarbonyloxy and arylcarbonyloxy), alkoxycarbonyl, aryloxycarbonyl, halocarbonyl, carboxy, carboxylate), carbamoyl, mono-(alkyl)-substituted carbamoyl, di-(alkyl)-substituted carbamoyl, mono-(aryl)-substituted carbamoyl, di-(aryl)substituted, di-N-(alkyl),N-(aryl)-substituted carbamoyl, thiocarbamoyl, mono-(alkyl)-substituted thiocarbamoyl, di-(alkyl)-substituted thiocarbamoyl, mono-(aryl)substituted thiocarbamoyl, di-(aryl)-substituted thiocarbamoyl, di-N-(alkyl), N-(aryl)-substituted thiocarbamoyl, CN, OCN, thiocyanato, formyl, C(S)H, NH$_2$, mono-(alkyl)-substituted amino, di-(alkyl)-substituted amino, mono-(aryl)substituted amino, di-(aryl)-substituted amino, alkylamido, arylamido, NO$_2$, NO, alkylthio (—S-alkyl), arylthio (—S-aryl), alkyl, alkenyl, alkynyl, aryl, and aralkyl. Within these substituent structures, the "alkyl," "alkylene," "alkenyl," "alkenylene," "alkoxy," "aromatic," "aryl," "aryloxy," and "aralkyl" moieties may be optionally fluorinated or perfluorinated.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

Compositions

The present disclosure is related to compositions and methods for metathesizing unsaturated compounds using one or more of a ruthenium catalyst, a photoredox catalyst, and visible light. In some embodiments, it is believed that the mode of activation is the energy or electron transfer from/to the excited state of the photocatalyst that induces ligand dissociation and thus starts metathesis. In other embodiments, upon irradiation by visible light, the photocatalyst is excited by absorption of a photon. In further embodiments, it also is believed that the methods induce dissociation of one of the carbene ligands from the latent metathesis catalyst, thus generating the active species that can start to promote ROMP or its mechanistically related congeners. In yet other embodiments, turning the light off leads to re-coordination of the carbene ligand onto the ruthenium catalyst and therefore is thought to shut down metathesis since the active catalyst is no longer present in the media. As a consequence, in some embodiments, the methods permit controlling initiation of the ROMP and accurately controlling the length of the polymer chains by modulating the irradiation time—these features that cannot be achieved with current systems in ROMP, and further expands the scope and ease of production of industrially relevant materials.

According to some embodiments, this disclosure relies on the activation of an external photocatalyst in order to activate the ruthenium metathesis catalyst and therefore start the polymerization event via an on and off process. In other embodiments, this disclosure provides a photocatalyst that is only catalytically-active upon absorption of visible light, providing an external handle for precisely controlling initiation and termination of ROMP. As such, in further embodiments, this disclosure provides a switchable photocatalyst for the industrial fabrication of polymers with controlled weights, chain length, and dispersity. In yet other embodiments, the photoredox-promoted ring opening metathesis polymerization provides increased control over initiation and should serve as a tool that enables to precisely control the length of the polymer chains, and thus the properties of the polymer, by controlling the irradiation time.

Accordingly, one embodiment of the present disclosure is a composition for olefin metathesis comprising a latent metathesis catalyst, and a photocatalyst, wherein the olefin metathesis is controlled by visible light irradiation. Thus, in some embodiments, the present disclosure provides the use of a latent ruthenium metathesis catalyst bearing two poorly dissociable carbene ligands that is not active for metathesis at ambient temperature without external activation.

As used herein, an "olefin metathesis" is an organic reaction that entails the redistribution of fragments of alkenes (olefins) by the scission and regeneration of carbon-carbon double bonds. As used herein, a "latent catalyst" is a catalyst that can be "switched on" from an inactive state by application of an external trigger such as, e.g., heat or light.

In other embodiments of the present disclosure, compositions for alkyne metathesis are provided comprising a latent metathesis catalyst, and a photocatalyst, wherein the alkyne metathesis is controlled by visible light irradiation.

In further embodiments of the present disclosure, compositions for mixed olefin/alkyne metathesis are provided comprising a latent metathesis catalyst, and a photocatalyst, wherein the olefin/alkyne metathesis is controlled by visible light irradiation.

The metathesis described herein is performed using a ruthenium metathesis catalyst and a photoredox catalyst that is activated by visible light. The terms "photocatalyst" and "photoredox catalyst" are interchangeable and refer to a catalyst that is activated by visible light. "Visible light" as used herein refers to light that has a wavelength of about 350 nm to about 750 nm. In some embodiments, the visible light has a wavelength of about 350 to about 700 nm, about 350 to about 650 nm, about 350 to about 600 nm, about 350 to about 550 nm, about 350 to about 500 nm, about 300 to about 450 nm, about 300 to about 400 nm, about 400 to about 750 nm, about 450 to about 750 nm, about 500 to about 750 nm, about 550 to about 750 nm, about 600 to about 750 nm, or about 650 to about 750 nm. In further embodiments, the visible light wavelength is about 400 to about 500 nm, about 410 to about 490 nm, about 420 to about 450 nm, about 430 to about 450 nm, or about 44 nm. The term "activated by visible light" refers to the state of photoredox catalyst going from unreactive to reactive.

The inventors determined that photoredox catalysts that are highly oxidizing contribute to the ease of metathesis. Thus, in some embodiments, the photoredox catalyst has an oxidizing potential of about 1.5 to about 3 volts, i.e., "highly oxidizing". In further embodiments, the oxidizing potential of the photoredox catalyst is about 1.5 to about 2.75 volts, about 1.5 to about 2.5 volts, about 1.5 to about 2 volts, about 1.75 to about 3 volts, about 1.75 to about 2.75 volts, about 1.75 to about 2.5 volts, about 1.75 to about 2 volts, about 2 to about 3 volts, or about 2 to about 2.5 volts. In other embodiments, the oxidizing potential is about 1.5 volts, 1.6 volts, 1.7 volts, 1.75 volts, 1.8 volts, 1.9 volts, 2 volts, 2.1 volts, 2.2 volts, 2.3 volts, 2.4 volts, 2.5 volts, 2.6 volts, 2.7 volts, 2.8 volts, 2.9 volts, or about 3 volts.

In some embodiments, the photoredox catalyst is of Formula (A):

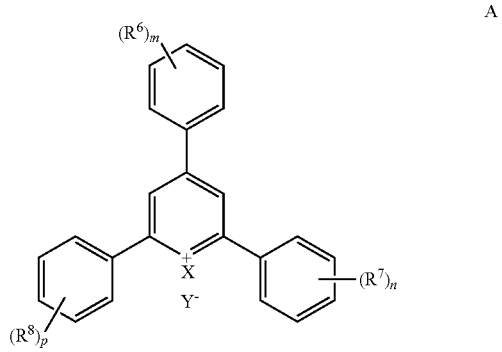

In these compounds, $R^6$, $R^7$, and $R^8$ are, independently, in each occurrence, H, halo, optionally substituted $C_{1-6}$alkyl, optionally substituted $C_{1-6}$alkoxy, optionally substituted $C_{1-6}$haloalkyl, CN, $NO_2$, optionally substituted aryl, optionally substituted heteroaryl, optionally substituted vinyl, $C(O)OR^L$, $CON(R^L)_2$, or $C(O)R^L$, where $R^L$ is optionally substituted H, $C_{1-6}$alkyl, $C_{1-6}$heteroalkyl, $C_{3-8}$cycloalkyl, aryl, or heteroaryl. In some embodiments, one, two, or all of $R^6$, $R^7$, and $R^8$ are halo. In other embodiments, one, two, or all of $R^6$, $R^7$, and $R^8$ are optionally substituted $C_{1-6}$alkyl. In further embodiments, one, two, or all of $R^6$, $R^7$, and $R^8$ are optionally substituted $C_{1-6}$alkoxy. In other embodiments, one, two, or all of $R^6$, $R^7$, and $R^8$ are optionally substituted $C_{1-6}$haloalkyl. In further embodiments, one two, or all of $R^6$, $R^7$, and $R^8$ are CN. In still other embodiments, one two, or all of $R^6$, $R^7$, and $R^8$ are $NO_2$. In yet further embodiments, one two, or all of $R^6$, $R^7$, and $R^8$ are optionally substituted aryl. In other embodiments, one two, or all of $R^6$, $R^7$, and $R^8$ are optionally substituted heteroaryl. In further embodiments, embodiments, one two, or all of $R^6$, $R^7$, and $R^8$ are optionally substituted vinyl. In still other embodiments, one two, or all of $R^6$, $R^7$, and $R^8$ are $C(O)OR^L$, where $R^L$ is optionally substituted $C_{1-6}$alkyl, $C_{1-6}$heteroalkyl, $C_{3-8}$cycloalkyl, aryl, or heteroaryl. In yet further embodiments, one, two, or all of $R^6$, $R^7$, and $R^8$ are $CON(R^L)_2$, where $R^L$ is H, optionally substituted $C_{1-6}$alkyl, $C_{1-6}$heteroalkyl, $C_{3-8}$cycloalkyl, aryl, or heteroaryl. In other embodiments, one, two, or all of $R^6$, $R^7$, and $R^8$ are $C(O)R^L$, where $R^L$ is H, optionally substituted $C_{1-6}$alkyl, $C_{1-6}$heteroalkyl, $C_{3-8}$cycloalkyl, aryl, or heteroaryl. In yet other embodiments, $R^6$, $R^7$, and $R^8$ are H or halo. In other embodiments, $R^6$, $R^7$, and $R^8$ are H or optionally substituted $C_{1-6}$alkyl. In further embodiments, $R^6$, $R^7$, and $R^8$ are H or optionally substituted $C_{1-6}$alkoxy. In other embodiments, $R^6$ is H. In further embodiments, $R^6$ is halo. In yet other embodiments, $R^6$ is optionally substituted $C_{1-6}$alkyl. In still further embodiments, $R^6$ is $C_{1-6}$alkoxy. In other embodiments, $R^6$ is optionally substituted $C_{1-6}$haloalkyl. In further embodiments, $R^6$ is CN. In still other embodiments, $R^6$ is $NO_2$. In yet further embodiments, $R^6$ is optionally substituted aryl. In other embodiments, $R^6$ is optionally substituted heteroaryl. In still further embodiments, $R^6$ is optionally substituted vinyl. In still other embodiments, $R^6$ is $C(O)OR^L$, wherein $R^L$ is defined herein. In yet further embodiments, $R^6$ is $CON(R^L)_2$, wherein $R^L$ is defined herein. In still other embodiments, $R^6$ is $C(O)R^L$, wherein $R^L$ is defined herein. In other embodiments, $R^7$ is H. In further embodiments, $R^7$ is halo. In yet other embodiments, $R^7$ is optionally substituted $C_{1-6}$alkyl. In still further embodiments, $R^7$ is optionally substituted $C_{1-6}$alkoxy. In other embodiments, $R^7$ is optionally substituted $C_{1-6}$haloalkyl. In further embodiments, $R^7$ is CN. In still other embodiments, $R^7$ is $NO_2$. In yet further embodiments, $R^7$ is optionally substituted aryl. In other embodiments, $R^7$ is optionally substituted heteroaryl. In still further embodiments, $R^7$ is optionally substituted vinyl. In still other embodiments, $R^7$ is $C(O)OR^L$, wherein $R^L$ is defined herein. In yet further embodiments, $R^7$ is $CON(R^L)_2$, wherein $R^L$ is defined herein. In still other embodiments, $R^7$ is $C(O)R^L$, wherein $R^L$ is defined herein. In other embodiments, $R^8$ is H. In further embodiments, $R^8$ is halo. In yet other embodiments, $R^8$ is optionally substituted $C_{1-6}$alkyl. In still further embodiments, $R^8$ is optionally substituted $C_{1-6}$alkoxy. In other embodiments, $R^8$ is optionally substituted $C_{1-6}$haloalkyl. In further embodiments, $R^8$ is CN. In still other embodiments, $R^8$ is $NO_2$. In yet further embodiments, $R^8$ is optionally substituted aryl. In other embodiments, $R^8$ is optionally substituted heteroaryl. In still further embodiments, $R^8$ is optionally substituted vinyl. In still other embodiments, $R^8$ is $C(O)OR^L$, wherein $R^L$ is defined herein. In yet further embodiments, $R^8$ is $CON(R^L)_2$, wherein $R^L$ is defined herein. In still other embodiments, $R^8$ is $C(O)R^L$, wherein $R^L$ is defined herein.

m, n, and p are, independently, 0 to 5. In some embodiments, m, n, and p are 1. In other embodiments, m, n, and p are 2. In further embodiments, m, n, and p are 3. In yet other embodiments, m, n, and p are 4. In still other embodiments, m, n, and p are 5. In other embodiments, m is 0. In further embodiments, m is 1. In still other embodiments, m is 2. In yet further embodiments, m is 3. In other embodiments, m is 4. In further embodiments, m is 5. In other embodiments, n is 0. In other embodiments, n is 1. In still other embodiments, n is 2. In yet further embodiments, n is 3. In other embodiments, n is 4. In further embodiments, n is 5. In other embodiments, p is 0. In further embodiments, p is 1. In still other embodiments, p is 2. In yet further embodiments, p is 3. In other embodiments, p is 4. In further embodiments, p is 5.

X is O or S. In some embodiments, X is O. In other embodiments, X is S.

Y is a counter anion. In some embodiments, Y is tetrafluoroborate ($BF_4$), hexafluorophosphate ($PF_6$), $SbF_6$, B(optionally substituted aryl)$_4$, $ClO_4^-$, halo, or an anion where the conjugate acid has a pKa lower than 4.5. In some embodiments, Y is $BF_4$. In other embodiments, Y is $PF_6$. In further embodiments, Y is $SbF_6$. In still other embodiments, Y is B(optionally substituted aryl)$_4$, where optionally substituted aryl is defined herein. In some embodiments, Y is B(phenyl)$_4$ or B(3,5-bis(trifluoromethyl)phenyl)$_4$. In other embodiments, Y is $ClO_4^-$. In yet further embodiments, Y is halo, such as F, Cl, Br, or I. In certain embodiments, Y is Br. In other embodiments, Y is Cl. In still further embodiments, Y is I. In other embodiments, Y is an anion where the conjugate acid has a pKa lower than 4.5 such as triflate ($CF_3SO_3^-$) and p-toluenesulfonate (p-$CH_3$—$C_6H_4$—$SO_3^-$).

In certain embodiments, the photoredox catalyst is:

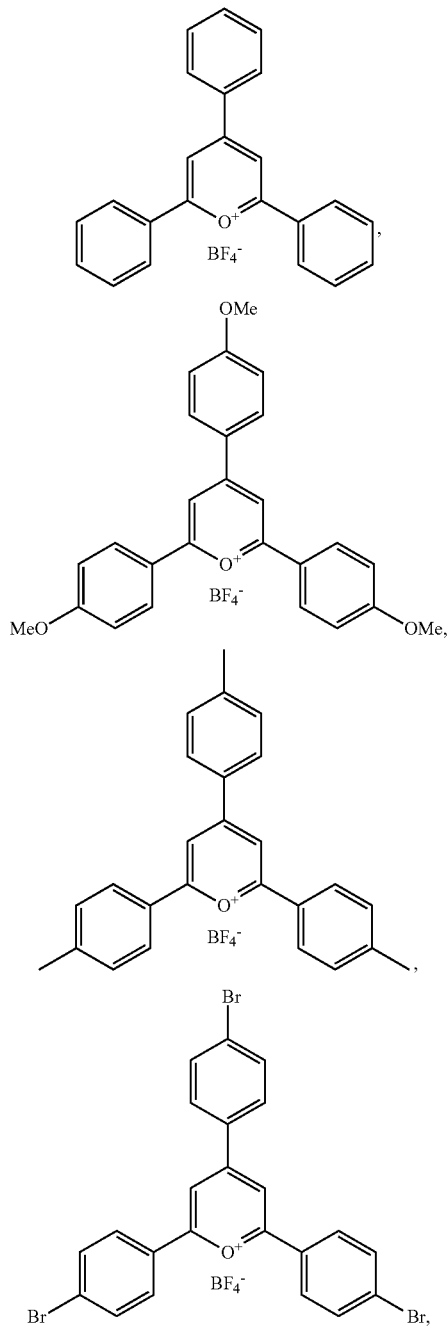

-continued
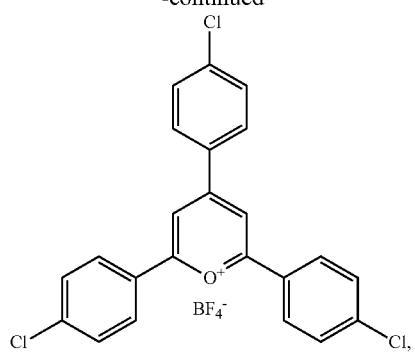
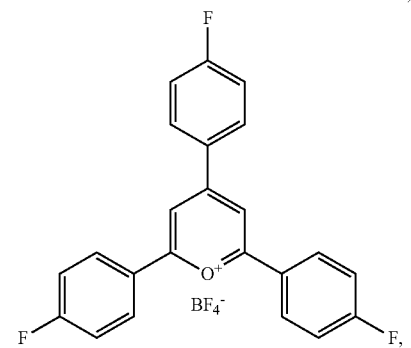
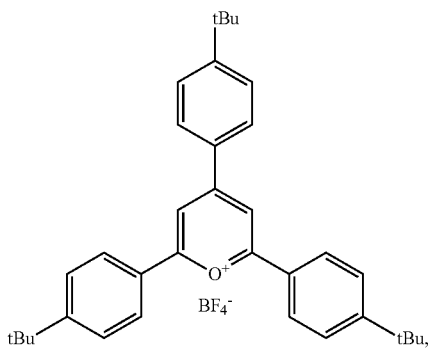
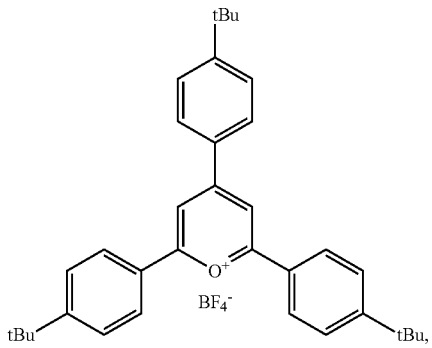
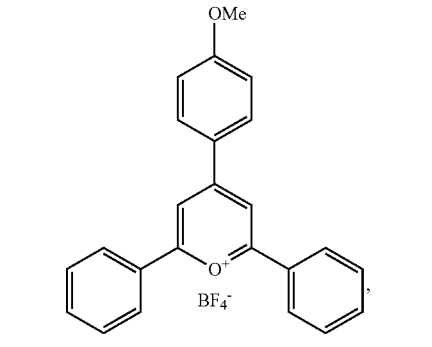
-continued
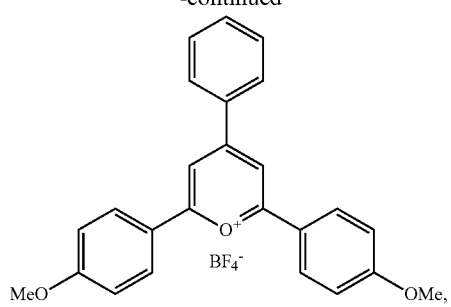
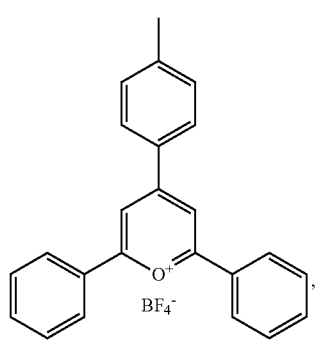
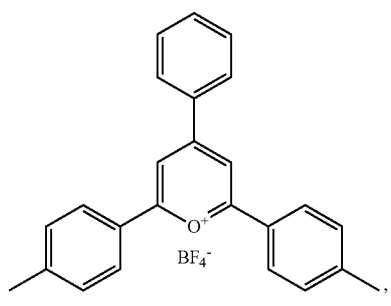
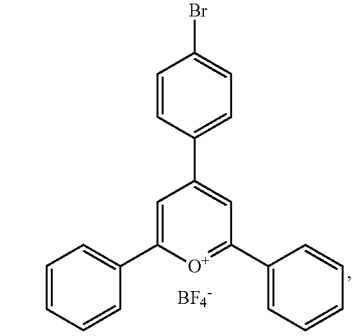
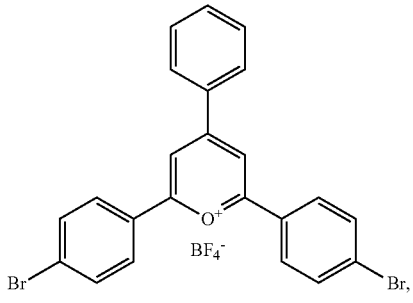

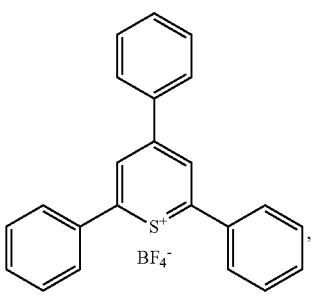
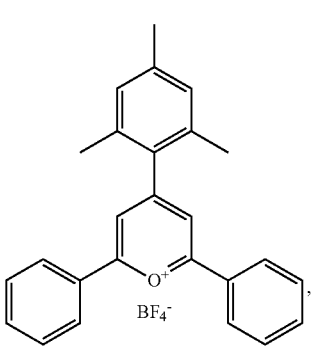
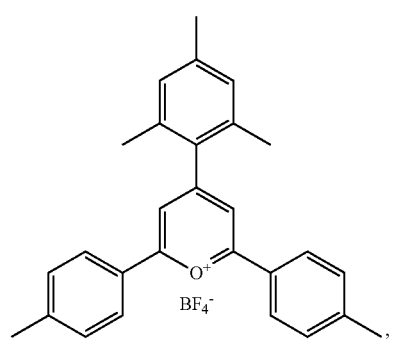
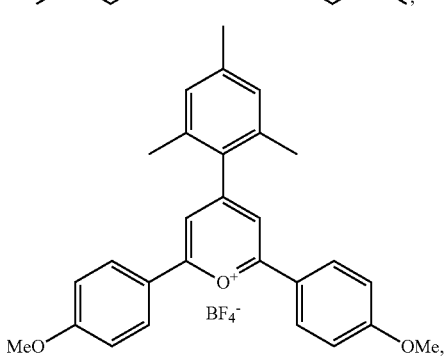
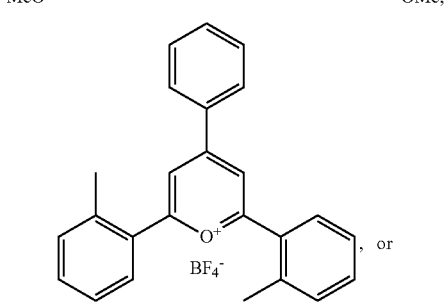
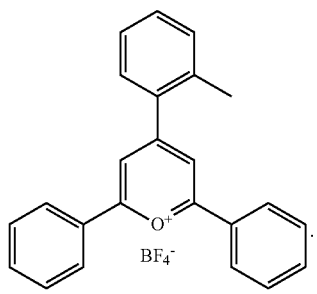
In other embodiments, the photoredox catalyst is 2,4,6-triphenylpyrylium tetrafluoroborate (TPPT):
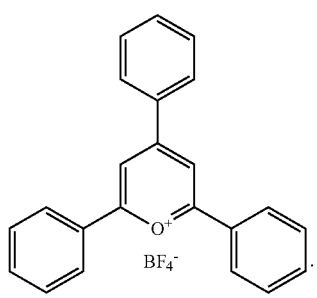
In further embodiments, the photoredox catalyst is
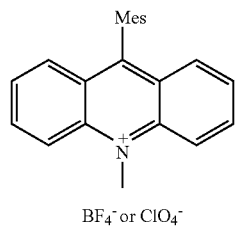
In yet other embodiments, the photoredox catalyst is:
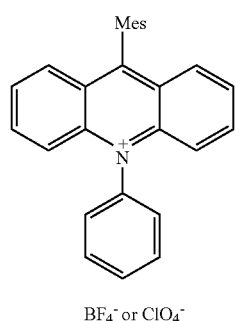

In still further embodiments, the photoredox catalyst is:

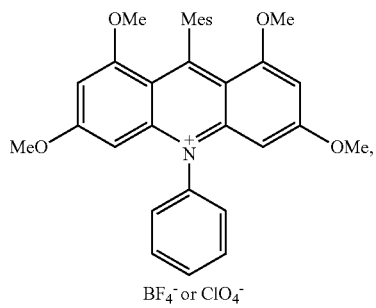

BF$_4^-$ or ClO$_4^-$

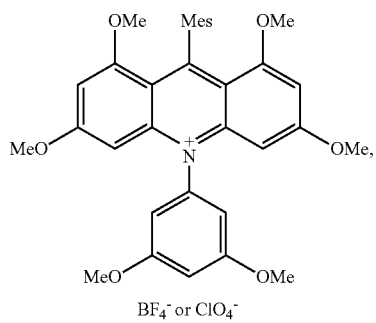

BF$_4^-$ or ClO$_4^-$

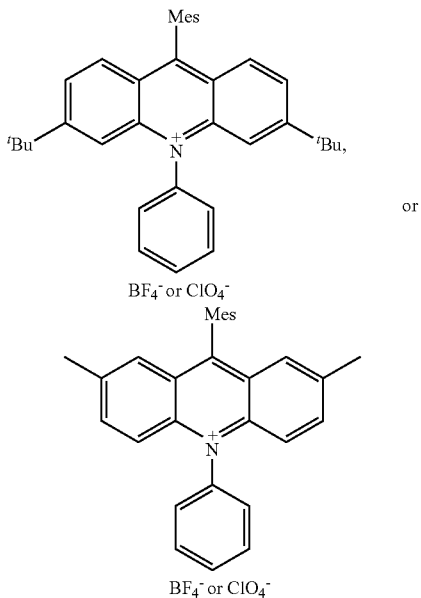

BF$_4^-$ or ClO$_4^-$ or

BF$_4^-$ or ClO$_4^-$

The metathesis of the disclosure also comprises the inclusion of a ruthenium catalyst. In some embodiments, the ruthenium catalyst is a latent ruthenium catalyst. The term "latent" as used herein refers to the state of the catalyst when it is inactivated, i.e., inactive or extremely sluggish. In some aspects, it is believed that the latent form of the ruthenium catalyst converts to an activated or active version of the ruthenium catalyst upon loss of one or more of its ligands. In some aspects, this loss of ligand is believed to arise by interaction of the Ru catalyst with the excited state of the photocatalyst leading to ligand oxidation and dissociation from Ru. In some embodiments, the ruthenium catalyst of Formula (I):

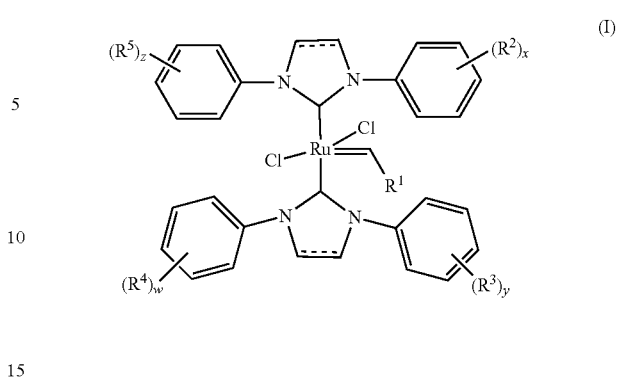

In the structure of Formula (I), $R^L$ is H, $C_{1-6}$alkyl, $C_{2-6}$alkenyl, aryl, or heteroaryl. In some embodiments, $R^1$ is H. In further embodiments, $R^1$ is $C_{1-6}$alkyl, such as methyl, ethyl, propyl, butyl, pentyl, or hexyl. In other embodiments, le is $C_{2-6}$alkenyl, such as ethenyl, propenyl, butenyl, pentenyl, or hexenyl. In further embodiments, le is aryl such as a $C_{5-24}$ aryl, more preferably $C_{5-14}$ aryl. In other embodiments, the aryl is an optionally substituted phenyl, naphthyl, or biphenyl. In yet further embodiments, $R^1$ is phenyl. In yet other embodiments, $R^1$ is heteroaryl such as azepinyl, acridinyl, carbazolyl, cinnolinyl, furanyl, furazanyl, furanonyl, isothiazolyl, imidazolyl, indazolyl, indolyl, isoindolyl, indolinyl, isoindolinyl, isoquinolyl, indolizinyl, isoxazolyl, naphthyridinyl, oxadiazolyl, oxazolyl, oxiranyl, phenazinyl, phenothiazinyl, phenoxazinyl, phthalazinyl, pteridinyl, purinyl, pyranyl, pyrrolyl, pyrrolidinyl, pyrazolyl, pyridinyl, pyrazinyl, pyrimidinyl, pyridazinyl, quinazolinyl, quinoxalinyl, quinolinyl, isoquinolinyl, tetrahydroquinolinyl, thiazolyl, thiadiazolyl, thiapyranyl, triazolyl, tetrazolyl, triazinyl, or thiophenyl.

$R^2$ to $R^5$ are, independently in each occurrence, H, $C_{1-6}$alkyl, $C_{1-6}$alkoxy, halo, or aryl. In some embodiments, $R^2$ to $R^5$ are H. In further embodiments, $R^2$ to $R^5$ are, independently in each occurrence, H or $C_{1-6}$alkyl. In other embodiments, $R^2$ to $R^5$ are, independently in each occurrence, H or $C_{1-6}$alkoxy. In further embodiments, $R^2$ to $R^5$ are, independently in each occurrence, H or halo. In yet other embodiments, $R^2$ to $R^5$ are, independently in each occurrence, H or aryl.

w to z are, independently, 0 to 5. In some embodiments, w is 0 to 5. In other embodiments, w is 1. In further embodiments, w is 2. In yet other embodiments, w is 3. In still further embodiments, w is 4. In other embodiments, x is 5. In some embodiments, x is 0 to 5. In other embodiments, x is 1. In further embodiments, x is 2. In yet other embodiments, x is 3. In still further embodiments, x is 4. In other embodiments, x is 5. In some embodiments, y is 0 to 5. In other embodiments, y is 1. In further embodiments, y is 2. In yet other embodiments, y is 3. In still further embodiments, y is 4. In other embodiments, y is 5. In some embodiments, z is 0 to 5. In other embodiments, z is 1. In further embodiments, z is 2. In yet other embodiments, z is 3. In still further embodiments, z is 4. In other embodiments, z is 5. In some embodiments, w, x, y, and z are 0. In other embodiments, w, x, y, and z are 1. In further embodiments, w, x, y, and z are 2. In yet other embodiments, w, x, y, and z are 3. In still further embodiments, w, x, y, and z are 4.

In some embodiments, the ruthenium catalyst is:

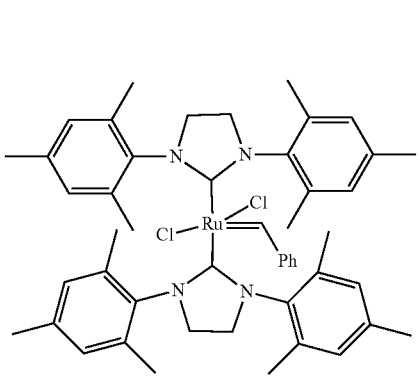

(SIMes)₂RuCl₂CHPh | RuCl₂(CHPh)(SIMes)₂

In other embodiments, the ruthenium catalyst is:

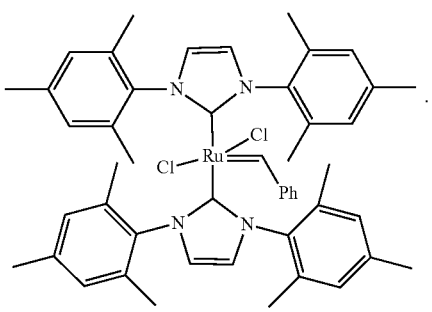

(IMes)₂RuCl₂CHPh | RuCl₂(CHPh)(IMes)₂

In other embodiments, the ruthenium catalyst is:

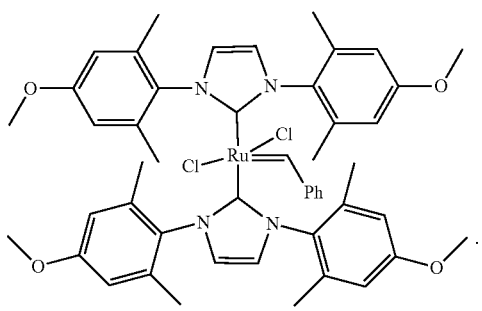

[(OMe)SIMes]₂RuCl₂CHPh

In other embodiments, the ruthenium catalyst is:

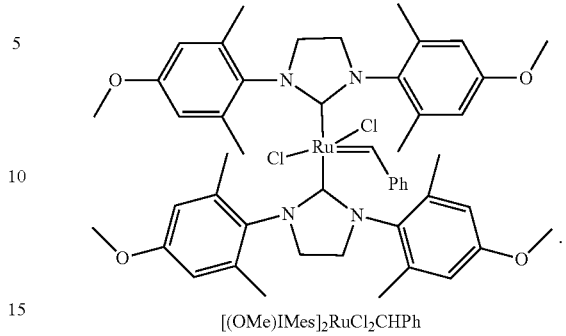

[(OMe)IMes]₂RuCl₂CHPh

For any one of the compositions or methods disclosed above, in some embodiments, the latent metathesis catalyst is a bis(NHC)-ruthenium complex. Non-limiting examples of a bis(NHC)-ruthenium complex include IMes₂RuCl₂CHPh and SIMes₂RuCl₂CHPh. In certain aspects, the bis(NHC)-ruthenium complex is IMes₂RuCl₂CHPh. In other aspects, the photocatalyst is a highly oxidizing photocatalyst, which is selected from acridinium and pyrylium derivatives. In further aspects, the photocatalyst is 2,4,6-tri-phenylpyrylium tetrafluoroborate (TPPT).

In some embodiments, the compositions comprise IMes₂RuCl₂CHPh and 2,4,6-tri-phenylpyrylium tetrafluoroborate (TPPT).

A scope of the metathesis described herein is not limited to those disclosed herein. Instead, one of skill in the art would be able to select suitable compounds to utilize in the metathesis described herein. In general, the compounds that may be metathesized according to the disclosure contain at least one point of unsaturation. The term "unsaturation" as used herein refers to a double or triple bond or any combination thereof. The term "double bond" as noted herein refers to a C=C group and a "triple bond" refers to a C≡C bond, either of which being contained in a chemical compound. The chemical compound containing a double bond is known in the art as an "alkene" or "olefin," which terms may be used interchangeably. Thus, a substituent on a molecule having a double bond is an "alkenyl" group. Similarly, a chemical compound containing a triple bond is known in the art as an "alkyne." Thus, a substituent on a molecule having a triple bond is an "alkynyl" group. In some embodiments, the metathesis is performed on a compound having two points of unsaturation. In other embodiments, the metathesis is performed on a first compound having at least one point of unsaturation and a second compound having at least one point of unsaturation.

As such, the present disclosure is directed to metathesizing a first alkenyl or alkynyl group with a second alkenyl or alkynyl group. In some embodiments, the present disclosure provides metathesizing a first alkenyl group with a second alkenyl group. In other embodiments, the present disclosure provides metathesizing a first alkenyl group with a first alkynyl group. In further embodiments, the present disclosure provides metathesizing a first alkynyl group and a second alkynyl group. In further embodiments, the present disclosure provides metathesizing a first alkenyl group, a second alkenyl group, and a third alkenyl group. In still other embodiments, the present disclosure provides metathesizing a first alkenyl group, a second alkenyl group, and a first alkynyl group. In yet further embodiments, the present disclosure provides metathesizing a first alkenyl group, a first alkynyl group, and a second alkynyl group.

The points of unsaturation may be present in the same molecule, thereby effecting a ring closing metathesis or intramolecular ring closing. As such, the single compound comprises at least the first alkenyl or alkynyl group and the second alkenyl or alkynyl group. The alkenyl and/or alkynyl group may be a terminal or internal group. The single compound may also contain other points of unsaturation or substituents that do not interfere with the metathesis.

In some embodiments, the one or more compound that can undergo a metathesis is of Formula (X1)-(X5):

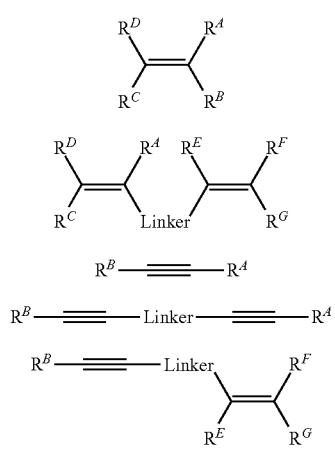

In these compounds, $R^A$ to $R^G$ are, independently, H, optionally substituted $C_{1-12}$alkyl, optionally substituted $C_{2-12}$alkenyl, optionally substituted $C_{2-12}$alkynyl, optionally substituted $C_{1-12}$haloalkyl, optionally substituted $C_{1-12}$heteroalkyl, optionally substituted $C_{3-12}$cycloalkyl, optionally substituted aryl, optionally substituted heteroaryl, optionally substituted heterocyclyl, OH, sulfonyl, CN, $NO_2$, halo, amino, C(O)H, COOH, acyl, carboxyl, amido, silyl, boryl, stannyl, or germyl. In other embodiments, $R^A$ to $R^G$ are, independently, H, halo (e.g., F, Cl, Br, I), OH, sulfhydryl, alkoxy, aryloxy, aralkyloxy, acyl (including alkylcarbonyl, arylcarbonyl, acyloxy (alkylcarbonyloxy and arylcarbonyloxy), alkoxycarbonyl, aryloxycarbonyl, halocarbonyl, carboxy, carboxylate), carbamoyl, mono-(alkyl)-substituted carbamoyl, di-(alkyl)-substituted carbamoyl, mono-(aryl)-substituted carbamoyl, di-(aryl)substituted, di-N-(alkyl),N-(aryl)-substituted carbamoyl, thiocarbamoyl, mono-(alkyl)-substituted thiocarbamoyl, di-(alkyl)-substituted thiocarbamoyl, mono-(aryl)substituted thiocarbamoyl, di-(aryl)-substituted thiocarbamoyl, di-N-(alkyl), N-(aryl)-substituted thiocarbamoyl, CN, OCN, thiocyanato, formyl, C(S)H, $NH_2$, mono-(alkyl)-substituted amino, di-(alkyl)-substituted amino, mono-(aryl)substituted amino, di-(aryl)-substituted amino, alkylamido, arylamido, $NO_2$, NO, alkylthio (—S-alkyl), arylthio (—S-aryl), alkyl, alkenyl, alkynyl, aryl, or aralkyl.

The Linker is absent or may be optionally substituted $C_{1-20}$alkyl, optionally substituted $C_{1-20}$heteroalkyl, optionally substituted $C_{3-12}$cycloalkyl, optionally substituted aryl, optionally substituted heteroaryl, optionally substituted heterocyclyl, sulfonyl, amino, carboxyl, or amido. In some embodiments, the Linker is a size that provides a product having about 4 to about 10 atoms. In other embodiments, the linker is a size that provides a product having about 5 to about 8 atoms, i.e., 5 atoms, 6 atoms, 7 atoms, or 8 atoms. Thus, in some embodiments, the linker has about 3 atoms, 4 atoms, 5 atoms, or 6 atoms.

In some embodiments, the compound is:

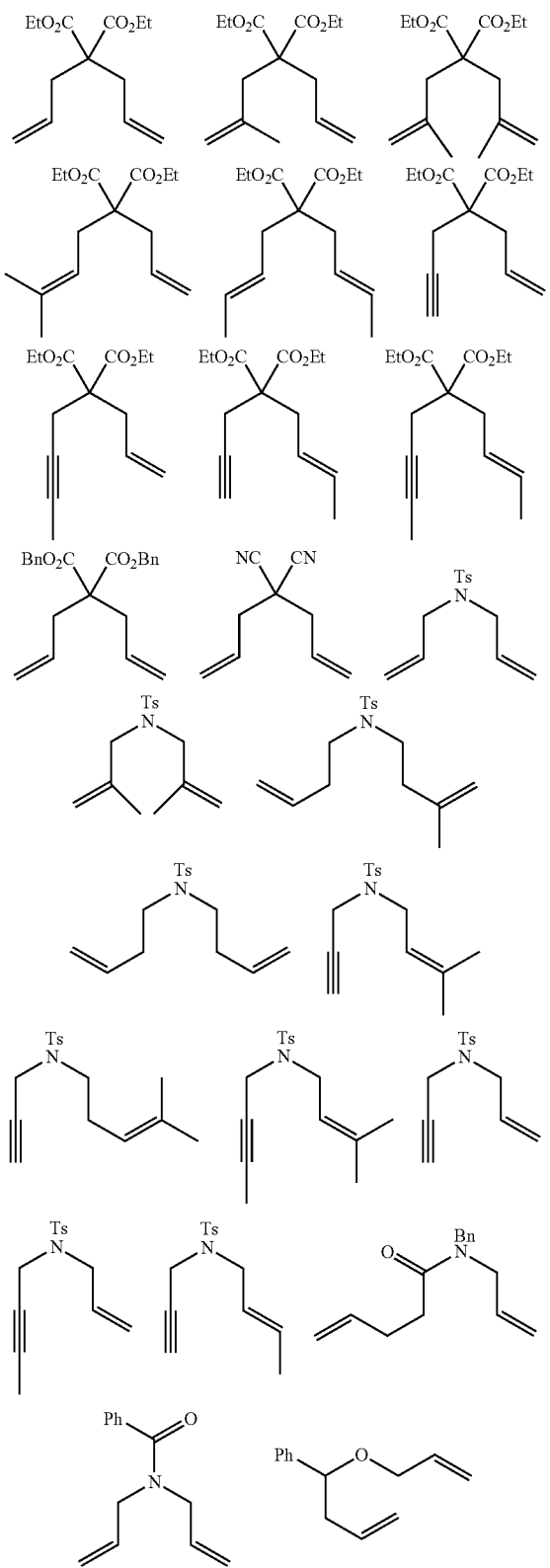

-continued

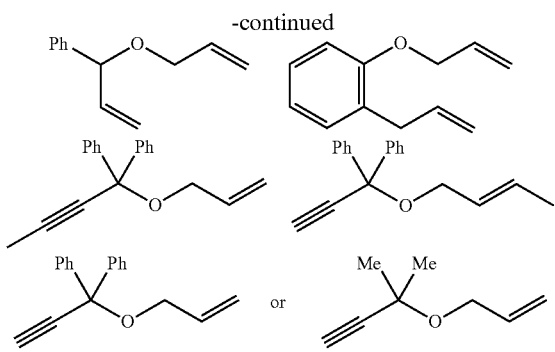

Alternatively, the points of unsaturation may be in two or more molecules. As such a first compound contains one point of unsaturation and a second compound contains the second point of unsaturation. Thus, the metathesis is an intermolecular reaction. In some embodiments, the first compound comprises the first alkenyl or alkynyl group and the second compound comprises the second alkenyl or alkynyl group. The alkenyl and/or alkynyl group may be a terminal or internal group. The single compound may also contain other points of unsaturation or substituents that do not interfere with the metathesis.

In some embodiments, the first compound and second compound are independently (X1)-(X5):

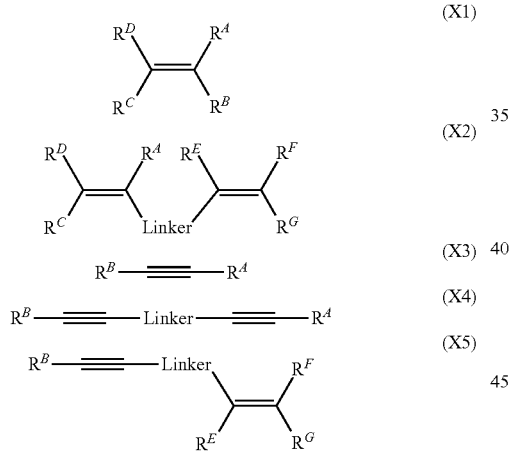

In these compounds, $R^A$ to $R^G$ are, independently, H, optionally substituted $C_{1-12}$alkyl, optionally substituted $C_{2-12}$alkenyl, optionally substituted $C_{2-12}$alkynyl, optionally substituted $C_{1-12}$haloalkyl, optionally substituted $C_{1-12}$heteroalkyl, optionally substituted $C_{3-12}$cycloalkyl, optionally substituted aryl, optionally substituted heteroaryl, optionally substituted heterocyclyl, OH, sulfonyl, CN, $NO_2$, halo, amino, C(O)H, COOH, acyl, carboxyl, amido, silyl, boryl, stannyl, or germyl. In other embodiments, $R^A$ to $R^G$ are, independently, H, halo (e.g., F, Cl, Br, I), OH, sulfhydryl, alkoxy, aryloxy, aralkyloxy, acyl (including alkylcarbonyl, arylcarbonyl, acyloxy (alkylcarbonyloxy and arylcarbonyloxy), alkoxycarbonyl, aryloxycarbonyl, halocarbonyl, carboxy, carboxylate), carbamoyl, mono-(alkyl)-substituted carbamoyl, di-(alkyl)-substituted carbamoyl, mono-(aryl)-substituted carbamoyl, di-(aryl)substituted, di-N-(alkyl),N-(aryl)-substituted carbamoyl, thiocarbamoyl, mono-(alkyl)-substituted thiocarbamoyl, di-(alkyl)-substituted thiocarbamoyl, mono-(aryl)substituted thiocarbamoyl, di-(aryl)-substituted thiocarbamoyl, di-N-(alkyl), N-(aryl)-substituted thiocarbamoyl, CN, OCN, thiocyanato, formyl, C(S)H, $NH_2$, mono-(alkyl)-substituted amino, di-(alkyl)-substituted amino, mono-(aryl)substituted amino, di-(aryl)-substituted amino, alkylamido, arylamido, $NO_2$, NO, alkylthio (—S-alkyl), arylthio (—S-aryl), alkyl, alkenyl, alkynyl, aryl, or aralkyl.

The Linker is absent or may be optionally substituted $C_{1-20}$alkyl, optionally substituted $C_{1-20}$heteroalkyl, optionally substituted $C_{3-12}$cycloalkyl, optionally substituted aryl, optionally substituted heteroaryl, optionally substituted heterocyclyl, sulfonyl, amino, carboxyl, or amido. In some embodiments, the Linker is a size that provides a product having about 4 to about 10 atoms. In other embodiments, the linker is a size that provides a product having about 5 to about 8 atoms, i.e., 5 atoms, 6 atoms, 7 atoms, or 8 atoms. Thus, in some embodiments, the linker has about 3 atoms, 4 atoms, 5 atoms, or 6 atoms.

In other embodiments, the two or more compounds are selected from among:

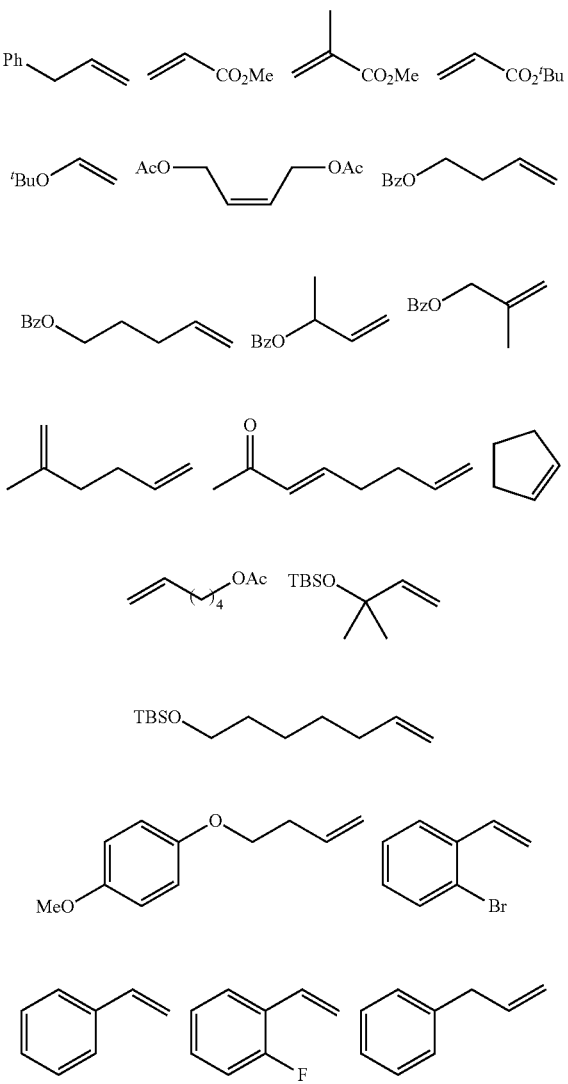

-continued

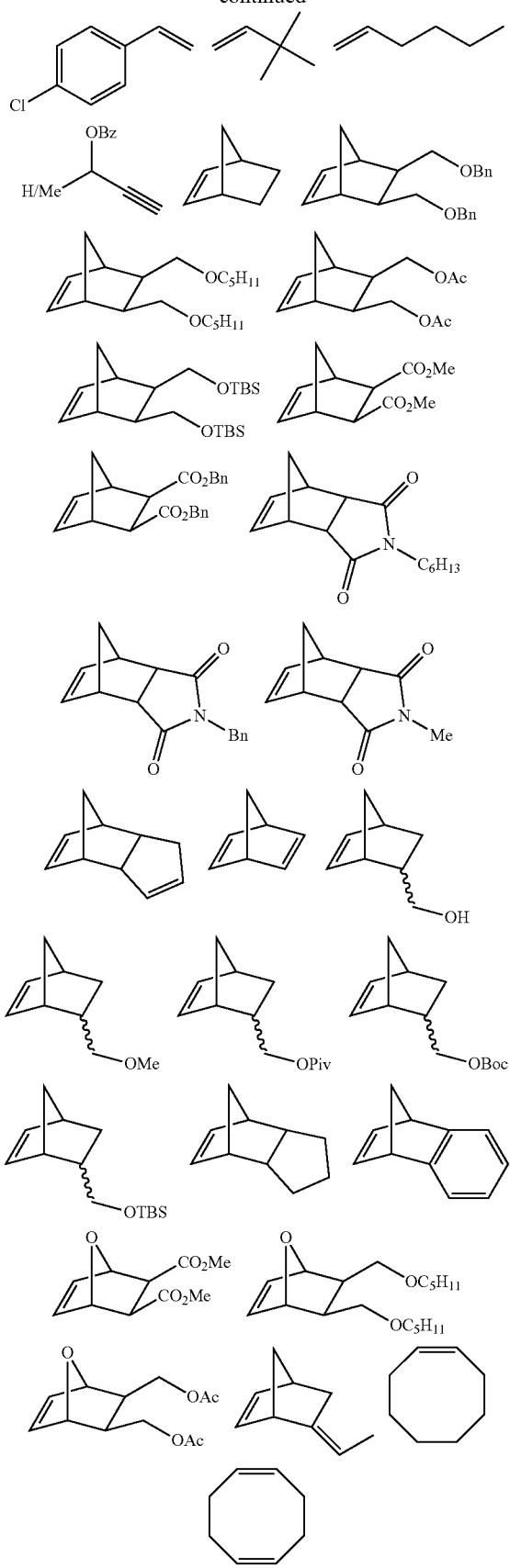

Metathesis Methods

As described herein, the present disclosure is directed to methods for chemical metathesis that can be performed easily, with high yields, and at ambient temperatures. The methods include the use of visible light, a ruthenium metathesis catalyst and a photoredox catalyst that is activated by the visible light. In some embodiments, these methods include applying visible light to one compound comprising a first alkenyl or alkynyl group and a second alkenyl or alkynyl group. In other embodiments, these methods include applying visible light to a first compound comprising a first alkenyl or alkynyl group and a second compound comprising a second alkenyl or alkynyl group. The visible light is applied to the compounds in the presence of the ruthenium metathesis catalyst and photoredox catalyst.

The metathesis may be any type of chemical reaction that exchanges chemical bonds to result in one or more products that differ from the reactants. Thus, the metathesis may be a ring-closing metathesis, cross-metathesis, ring-opening metathesis polymerization, photolithographic olefin metathesis polymerization. In some embodiments, the methods described herein relate to ring-closing metathesis, i.e., an intramolecular metathesis. In other embodiments, the methods described herein relate to cross-metathesis, i.e., an intermolecular metathesis. In further embodiments, the methods described herein related to ring-opening metathesis polymerization. In yet other embodiments, the methods relate to photolithographic olefin metathesis polymerization.

Advantageously, the methods discussed herein may be performed at a range of temperatures without an adverse effect of the yield or conversion. In some embodiments, the metathesis is performed at a temperature of about −80 to about 200° C. In further embodiments, the metathesis may be performed at about −80° C., about −75° C., about −70° C., about −65° C., about −60° C., about −55° C., about −50° C., about −45° C., about −40° C., about −35° C., about −30° C., about −25° C., about −20° C., about −15° C., about −10° C., about −5° C., about 0° C., about 10° C., about 15° C., 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., 140° C., about 145° C., about 150° C., about 155° C., about 160° C., about 165° C., about 170° C., about 175° C., about 180° C., about 185° C., about 190° C., about 195° C., or about 200° C. In other embodiments, the metathesis may be performed at a temperature at about −80 to about 180° C., about −80 to about 150° C., about −80 to about 125° C., about −80 to about 100° C., about −80 to about 75° C., about −80 to about 50° C., about −80 to about 25° C., about −80 to about 0° C., about −80 to about −20° C., about −30 to about 180° C., about −30 to about 150° C., about −30 to about 125° C., about −30 to about 100° C., about −30 to about 75° C., about −30 to about 50° C., about −30 to about 25° C., about −30 to about 0° C., about −30 to about −20° C., about −10 to about 180° C., about −10 to about 150° C., about −10 to about 125° C., about −10 to about 100° C., about −10 to about 75° C., about −10 to about 50° C., about −10 to about 25° C., about −10 to about 0° C., about 0 to about 180° C., about 0 to about 150° C., about 0 to about 125° C., about 0 to about 100° C., about 0 to about 75° C., about 0 to about 50° C., about 0 to about 25° C., 10 to about 180° C., about 10 to about 150° C., about 10 to about 125° C., about 10 to about 100° C., about 10 to about 75° C., about 10 to about 50° C., or about 10 to about 25° C. In yet other embodiments, the metathesis is performed at room temperature. In still further embodiments, the metathesis is performed at a temperature of about 20 to about 30° C.

The amount of the ruthenium metathesis catalyst and/or photoredox catalyst depends on the compound to be metathesized and product to be prepared. In some embodiments, lower amounts of the ruthenium metathesis catalyst and/or photoredox catalyst are used. In other embodiments, it is contemplated that higher amounts of the ruthenium metathesis catalyst and/or photoredox catalyst may be required. Thus, in some embodiments, the metathesis is performed using about 0.01 to about 10 mol %, based on the mol % of the one compound or first and second compound, of the ruthenium metathesis catalyst. In other embodiments, the metathesis is performed using about 0.05 to about 10 mol %, about 1 to about 10 mol %, about 1.5 to about 10 mol %, about 2 to about 10 mol %, about 2.5 to about 10 mol %, about 3 to about 10 mol %, about 3.5 to about 10 mol %, about 4 to about 10 mol %, about 4.5 to about 10 mol %, about 5 to about 10 mol %, about 5.5 to about 10 mol %, about 6 to about 10 mol %, about 6.5 to about 10 mol %, about 7 to about 10 mol %, about 7.5 to about 10 mol %, about 8 to about 10 mol %, about 8.5 to about 10 mol %, about 9 to about 10 mol %, about 0.01 to about 9 mol %, about 0.01 to about 8 mol %, about 0.01 to about 7 mol %, about 0.01 to about 6 mol %, about 0.01 to about 5 mol %, about 0.01 to about 4 mol %, about 0.01 to about 3 mol %, about 0.01 to about 2 mol %, about 0.01 to about 1 mol %, about 2 to about 7.5 mol %, about 2.5 to about 7.5 mol %, about 5 to about 7 mol %, or about 5 to about 10 mol %, based on the mol % of the one compound or first and second compound, of the ruthenium metathesis catalyst. In further embodiments, the metathesis is performed using about 2 to about 7.5 mol %, based on the mol % of the one compound or first and second compound, of the ruthenium metathesis catalyst. In still other embodiments, the metathesis is performed using about 5 mol %, based on the mol % of the one compound or first and second compound, of the ruthenium metathesis catalyst.

Thus, in some embodiments, the metathesis is performed using about 0.05 to about 10 mol %, based on the mol % weight of the one compound or first and second compound, of the photoredox catalyst. In other embodiments, the metathesis is performed using about 1 to about 10 mol %, about 1.5 to about 10 mol %, about 2 to about 10 mol %, about 2.5 to about 10 mol %, about 3 to about 10 mol %, about 3.5 to about 10 mol %, about 4 to about 10 mol %, about 4.5 to about 10 mol %, about 5 to about 10 mol %, about 5.5 to about 10 mol %, about 6 to about 10 mol %, about 6.5 to about 10 mol %, about 7 to about 10 mol %, about 7.5 to about 10 mol %, about 8 to about 10 mol %, about 8.5 to about 10 mol %, about 9 to about 10 mol %, about 0.05 to about 9 mol %, about 0.05 to about 8 mol %, about 0.05 to about 7 mol %, about 0.05 to about 6 mol %, about 0.05 to about 5 mol %, about 0.05 to about 4 mol %, about 0.05 to about 3 mol %, about 0.05 to about 2 mol %, about 0.05 to about 1 mol %, about 2 to about 7.5 mol %, about 2.5 to about 7.5 mol %, about 5 to about 7 mol %, or about 5 to about 10 mol %, based on the mol % of the one compound or first and second compound, of the photoredox catalyst. In further embodiments, the metathesis is performed using about 2 to about 7.5 mol %, based on the mol % of the one compound or first and second compound, of the photoredox catalyst. In still other embodiments, the metathesis is performed using about 7.5 mol %, based on the mol % of the one compound or first and second compound, of the photoredox catalyst.

The inventors also found that the concentration of the one or more compounds containing the points of unsaturation can be adjusted to optimize the metathesis. In some embodiments, the concentration of the one compound or first and second compound, all containing points of unsaturation, is about 0.01 to about 5M. In other embodiments, the concentration is about 0.01 to about 4.5M, about 0.01 to about 4M, about 0.01 to about 3.5M, about 0.01 to about 3M, about 0.01 to about 2.5M, about 0.01 to about 2M, about 0.01 to about 1.5M, about 0.01 to about 1M, about 0.01 to about 0.05M, about 0.5M to about 5M, about 0.1 to about 1M, about 0.1 to about 0.8M, about 0.1 to about 0.75M, about 0.1 to about 0.5M, about 0.1 to about 0.4M, about 0.1 to about 0.3M, about 0.1 to about 0.2M, about 1 to about 5M, about 1.5 to about 5M, about 2 to about 5M, about 2.5 to about 5M, about 3 to about 5M, about 3.5 to about 5M, about 4 to about 5M, or about 4.5 to about 5M. In further embodiments, the concentration is about 0.01 to about 0.5 M. In yet other embodiments, the concentration is about 0.1 to about 0.3 M.

The metathesis is performed for a period of time as determined by those skilled in the art depending on the ruthenium catalyst, photoredox catalyst, temperature, and one or more compounds to be metathesized. The reaction time can be varied as needed to control the thickness of the metathesized compound, among others. Thus, shorter periods of times may result in thinner polymers, whereas longer periods of time may result in thicker polymers. In some embodiments, the metathesis is performed for at least about 10 seconds. In other embodiments, the metathesis is performed for at least about 1 minute. In further embodiments, the metathesis is performed for at least about 2 minutes, 3 minutes, 4 minutes, 5 minutes, 10 minutes, 30 minutes, 60 minutes, 2 hours, 3 hours, 4 hours, 5 hours, 6 hours, 12 hours, or 24 hours, or longer.

Spatial Control Methods

In addition to the fact that the metatheses described herein may be performed with high yields and conversions, optionally at ambient conditions when needed, the inventors found that they could be spatially controlled. As such, methods for spatially controlling a metathesis also are provided by the disclosure, as are methods for preparing polymeric materials or patterns, and patterning surfaces on a micro scale as described below.

The term "micro scale" as used herein refers to patterned polymers having a size of about 1 mm or less. The size may be in any direction of the patter, i.e., width, length or depth. In some embodiments, micro scale refers to a size of about 1 nm to about 1 mm. In other embodiments, micro scale refers to a size of about 1 nm to about 1 In further embodiments, micro scale refers to a size of about 1 μm to about 1 mm. In still other embodiments, micro scale refers to a size of about 10 to about 100 μm, about 20 to about 100 μm, about 30 to about 100 μm, about 40 to about 100 μm, about 50 to about 100 µm, about 60 to about 100 µm, about 70 to about 100 µm, about 80 to about 100 µm, about 90 to about 100 µm, about 10 to about 90 µm, about 10 to about 80 µm, about 10 to about 80 µm, about 10 to about 70 µm, about 10 to about 60 µm, about 10 to about 50 µm, about 10 to about 40 µm, about 10 to about 30 µm, about 10 to about 20 µm, about 20 to about 90 µm, about 20 to about 80 µm, about 20 to about 70 µm, about 20 to about 60 µm, about 20 to about 50 µm, about 20 to about 40 µm, about 20 to about 30 µm, about 30 to about 90 µm, about 30 to about 80 µm, about 30 to about 70 µm, about 30 to about 60 µm, about 30 to about 60 µm, about 30 to about 50 µm, about 30 to about 40 µm, about 40 to about 90 µm, about 30 to about 80 µm, about 30 to about 70 µm, about 30 to about 60 µm, about 30 to about 50 µm, about 30 to about 40 µm, about 40 to about 90 µm, about 40 to about 80 µm, about 40 to about 70 µm, about 40 to about 60 µm, about 40 to about 50 µm, about 50 to about 90 µm, about 50 to about 80 µm, about 50 to about 70 µm, about 50 to about 60 µm, about 60 to about 90 µm, about 60 to about 80 µm, about 60 to about 70 µm, about 70 to about 90 µm, about 70 to about 80 µm, or about 80 to about 90 µm.

Methods of spatially controlling a metathesis comprise forming a mixture of a ruthenium metathesis catalyst, a photoredox catalyst, and one or more compounds susceptible to metathesis and applying visible light to one or more regions of the mixture. By doing so, the methods provide one or more metathesized regions and one or more unmetathesized regions.

The mixture may be formed or added to a substrate that contains the mixture. In some embodiments, the substrate is a glass, plastic, an organic surface including a metal such as gold, or iron, cloth, wood, silicon, diamond, graphite, charcoal, metal organic framework, among others. In some embodiments, the substrate is a petri dish. In other embodiments, the substrate is a wafer, such as a silicon wafer. As such, the substrate does not participate in the metathesis or otherwise form any bonds with the one or more compounds, ruthenium metathesis catalyst, photoredox catalyst, or product formed therefrom.

Thus, in certain embodiments, the mixture may be disposed on the substrate prior to metathesis. In further embodiments, the mixture is disposed on a substrate that does not participate in the metathesis.

The disclosure also envisions embodiments wherein substrate is functionalized with the one or more compounds susceptible to metathesis, ruthenium metathesis catalyst, photoredox catalyst, or combinations thereof. By doing so, the substrate is linked to a metathesized region. In some embodiments, the substrate is functionalized with the one or more compounds susceptible to metathesis. In other embodiments, the substrate is pre-functionalized with the one or more compound before adding the photoredox catalyst or ruthenium metathesis catalyst. In further embodiments, the substrate is functionalized with the photoredox catalyst. In yet other embodiments, the substrate is functionalized with the ruthenium metathesis catalyst. As but one example, the present disclosure provides methods that comprise applying visible light to a ruthenium metathesis catalyst, a photoredox catalyst, and one or more compounds susceptible to metathesis, the applying being performed so as to give rise to one or more metathesized regions, at least one of the ruthenium metathesis catalyst and the photoredox catalyst (or even both of the foregoing) being linked to a substrate, the substrate optionally being stationary. The visible light can be applied in a predetermined pattern. The visible light can also be applied from two or more sources.

The visible light may be applied using any light source known in the art. On some embodiments, the visible light is applied using a high resolution light source. The term "high resolution" as used herein refers to light that is delivered to a specific location on a substrate. In some embodiments, the high resolution light source is a laser. In other embodiments, the high resolution light source is a fine beam of light.

In order to spatially control the metathesis, the regions that are not to be metathesized, i.e., the unmetathesized regions, are covered with a photomask. By doing so, the light penetrates the mask in intended locations as determined by the shape and placement of the mask. The terms "mask" and "photomask" as used herein are interchangeable and refer to an object that physically covers regions of the compounds susceptible to metathesis. Desirably, the mask is substantially opaque to visible light. In some embodiments, the mask is black in color or made of a material that reflects visible light. In other embodiments, the mask is black paper, black plastic, a metal sheet, or a metal foil. The mask may also have one or more openings whereby visible light may pass through. By doing so, those openings permit the visible light to only be applied to those regions of the mixture that are intended to metathesize. As the final product, the mixture will contain unmetathesized and metathesized regions.

The disclosure also provides steps for recovering only those metathesized regions. In doing so, the unmetathesized regions may be removed by rinsing with a solvent. In some embodiments, the solvent is added to the mixture and thereby removed to provide the metathesized region. The solvent selected desirably is effect to only solubilize the unmetathesized regions, and not the metathesized regions. One skilled in the art would understand how long the rinsing should be performed and how best to remove the solvent after rinsing.

A further embodiment of the present disclosure is a method of exerting spatial control over metathesis comprising: (a) providing a reaction mixture of a latent metathesis catalyst, a photocatalyst, and a substrate; and (b) applying visible light to selected areas of the reaction mixture; wherein the selected areas of the reaction mixture are selected by: (i) macroscopic or microscopic photomask; or (ii) high resolution light source. In some embodiments, the reaction mixture is provided on a support surface. In certain embodiments, the support surface is a pre-functionalized support surface.

Another embodiment of the present disclosure is a method for visible light controlled olefin metathesis, comprising: (a) providing a reaction mixture of a latent metathesis catalyst, a photocatalyst, and a substrate; and (b) applying visible light to the reaction mixture for a desired time. In some embodiments, the olefin metathesis is selected from ring-closing metathesis (RCM), cross-metathesis (CM), and ring-opening metathesis polymerization (ROMP). In some embodiments, step (b) of the method disclosed above is carried out at room temperature.

The present disclosure further provides compositions and processes as disclosed or depicted in the Appendix attached hereto, and/or kits containing such compositions or for carrying out such processes.

The embodiments described in this disclosure can be combined in various ways. Any aspect or feature that is described for one embodiment can be incorporated into any other embodiment mentioned in this disclosure. While various novel features of the inventive principles have been shown, described and pointed out as applied to particular embodiments thereof, it should be understood that various omissions and substitutions and changes may be made by those skilled in the art without departing from the spirit of this disclosure. Those skilled in the art will appreciate that the inventive principles can be practiced in other than the described embodiments, which are presented for purposes of illustration and not limitation.

The following listing of aspects is intended to complement, rather than displace or supersede, the previous descriptions.

Aspects

Aspect 1: A composition for olefin metathesis comprising a latent metathesis catalyst and a photocatalyst, wherein the olefin metathesis is controlled by visible light irradiation.

Aspect 2: The composition of aspect 1, wherein the latent metathesis catalyst is a bis(NHC)— ruthenium complex.

Aspect 3: The composition of aspect 2, wherein the bis(NHC)-ruthenium complex is selected from IMes$_2$RuCl$_2$CHPh and SIMes$_2$RuCl$_2$CHPh.

Aspect 4: The composition of aspect 2, wherein the bis(NHC)-ruthenium complex is IMes$_2$RuCl$_2$CHPh.

Aspect 5: The composition of aspect 1, wherein the photocatalyst is a highly oxidizing photocatalyst.

Aspect 6: The composition of aspect 1, wherein the photocatalyst is selected from acridinium and pyrylium derivatives.

Aspect 7: The composition of aspect 1, wherein the photocatalyst is 2,4,6-tri-phenylpyrylium tetrafluoroborate (TPPT).

Aspect 8: A composition comprising IMes$_2$RuCl$_2$CHPh and 2,4,6-tri-phenylpyrylium tetrafluoroborate (TPPT).

Aspect 9: A method for visible light controlled olefin metathesis, comprising: providing a reaction mixture of a latent metathesis catalyst, a photocatalyst, and a substrate; and applying visible light to the reaction mixture for a desired time.

Aspect 10: The method of aspect 9, wherein the olefin metathesis is selected from ring-closing metathesis (RCM), cross-metathesis (CM), and ring-opening metathesis polymerization (ROMP).

Aspect 11: The method of aspect 9, wherein the latent metathesis catalyst is a bis(NHC)— ruthenium complex and the photocatalyst is a highly oxidizing photocatalyst.

Aspect 12: The method of aspect 9, wherein step (b) is carried out at room temperature.

Aspect 13: The method of aspect 11, wherein the bis (NHC)-ruthenium complex is selected from IMes$_2$RuCl$_2$CHPh and SIMes$_2$RuCl$_2$CHPh, and the photocatalyst is selected from acridinium and pyrylium derivatives.

Aspect 14: The method of aspect 9, wherein the latent metathesis catalyst is IMes$_2$RuCl$_2$CHPh and the photocatalyst is 2,4,6-tri-phenylpyrylium tetrafluoroborate (TPPT).

Aspect 15: A method of exerting spatial control over metathesis comprising: providing a reaction mixture of a latent metathesis catalyst, a photocatalyst, and a substrate; and applying visible light to selected areas of the reaction mixture; wherein the selected areas of the reaction mixture are selected by: (i) macroscopic or microscopic photomask; or (ii) high resolution light source.

Aspect 16: The method of aspect 15, wherein the reaction mixture is provided on a support surface.

Aspect 17: The method of aspect 16, wherein the support surface is a pre-functionalized support surface.

Aspect 18: The method of aspect 15, wherein the latent metathesis catalyst is a bis(NHC)— ruthenium complex.

Aspect 19: The method of aspect 18, wherein the bis (NHC)-ruthenium complex is selected from IMes$_2$RuCl$_2$CHPh and SIMes$_2$RuCl$_2$CHPh.

Aspect 20: The method of aspect 15, wherein the photocatalyst is a highly oxidizing photocatalyst.

Aspect 21: The method of aspect 15, wherein the photocatalyst is selected from acridinium and pyrylium derivatives.

Aspect 22: The method of aspect 15, wherein the photocatalyst is 2,4,6-tri-phenylpyrylium tetrafluoroborate (TPPT).

Aspect 23: The method of aspect 15, wherein the latent metathesis catalyst is IMes$_2$RuCl$_2$CHPh and the photocatalyst is 2,4,6-tri-phenylpyrylium tetrafluoroborate (TPPT).

Aspect 24: A composition or process as disclosed or depicted in Appendix 1.

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

EXAMPLES

Example 1

Olefin metathesis is one of the most attractive and powerful tools for the creation of carbon-carbon π bonds, finding numerous applications in synthetic chemistry, fine chemical synthesis and materials science. See, Grela, Olefin Metathesis: Theory and Practice; Wiley: Hoboken, NJ, 2014; Grubbs, Handbook of Metathesis, 2nd ed.; Wiley-VHC: Weinheim, 2015; Trnka, Acc. Chem. Res. 2001, 34, 18-29; Hoveyda, Nature 2007, 450, 243-250. Ogba, Chem. Soc. Rev. 2018, 47, 4510-4544. Katz, Angew. Chem. Int. Ed. 2005, 44, 3010-3019; Higman, Angew. Chem. Int. Ed. 2016, 55, 3552-3565. While most synthetic efforts have been devoted to the development of ever-more efficient catalysts, increased attention has been paid to the development of catalysts that can be activated/deactivated on demand. See, Blanco, Chem. Soc. Rev. 2015, 44, 5341-5370; Choudhury, Tetrahedron Lett. 2018, 59, 487-495. Such latent catalysts are dormant species under ambient conditions and require an external stimulus to become active. Increased control on reactions is crucial not only from an understanding viewpoint but also for applications in materials science for the production of new well-defined materials. See, Leibfarth, Angew. Chem. Int. Ed. 2013, 52, 199-210; Teator, Chem.

Rev. 2016, 116, 1969-1992; Ogawa, Synlett 2016, 27, 203-214; Teator, J. Polym. Sci. Pol. Chem. 2017, 55, 2949-2960. Various stimuli have been exploited to achieve such control in metathesis reactions, including heat, light, ultrasound, acid and redox switches. See, Szadkowska, Curr. Org. Chem. 2008, 12, 1631-1647; Monsaert, Chem. Soc. Rev. 2009, 38, 3360-3372; Vidaysky, J. Org. Chem. 2010, 6, 1106-1119; Eivgi, Synthesis 2018, 50, 49-63. Light is arguably the most convenient and attractive stimulus since it is non-invasive, can be easily manipulated and provides the opportunity for high temporal and spatial resolution (FIG. 1). See, Stoll, Angew. Chem. Int. Ed. 2010, 49, 5054-5075; Neilson, ACS Catal. 2013, 3, 1874-1885; Gostl, Chem. Soc. Rev. 2014, 43, 1982-1996. As a consequence, several recent reports have described light-promoted olefin metathesis. See, Wang, Angew. Chem. Int. Ed. 2008, 47, 3267-3270; Wang, Chem. Eur. J. 2010, 16, 12928-12934; Keitz, J. Am. Chem. Soc. 2009, 131, 2038-2039; Khalimon, Organometallics 2012, 31, 5634-5637; Ben-Asuly, Organometallics 2009, 28, 4652-4655; Levin, Angew. Chem. Int. Ed. 2015, 54, 12384-12388; Sutar, Angew. Chem. Int. Ed. 2016, 55, 764-767; Teator, Organometallics 2017, 36, 490-497. While these have been important developments, they are dominated by UV light with most reports describing activation rather than gating control of alkene metathesis.

We considered that the merger of olefin metathesis with photoredox catalysis could lead to visible light control of alkene metathesis. See, Prier, Chem. Rev. 2013, 113, 5322-5363; Tellis, Acc. Chem. Res. 2016, 49, 1429-1439; Romero, Chem. Rev. 2016, 116, 10075-10166; Skubi, Chem. Rev. 2016, 116, 10035-10074. Visible light photoredox catalysis has already proven successful for metal-free olefin metathesis polymerization via a radical mechanism. See, Ogawa, J. Am. Chem. Soc. 2015, 137, 1400-1403; Goetz, J. Am. Chem. Soc. 2015, 137, 7572-7575; Goetz, ACS Macro Lett. 2016, 5, 579-582. In particular, excitation of the appropriate photocatalyst by visible-light irradiation should permit the activation of a latent metathesis catalyst, most probably by inducing ligand dissociation, and therefore lead to the development of an on-demand metathesis system. Importantly, the use of visible light is more convenient than UV light while still providing high levels of temporal and spatial resolution. See, Ruhl, J. Am. Chem. Soc. 2015, 138, 15527-15530; Ravetz, ACS Catal. 2018, 8, 5323-5327; Ravetz, ACS Catal. 2019, 9, 200-204. Overall, the development of such a system would open new perspectives in photolithography and in materials science for the design of new materials, as already illustrated by the impact of recent work reported for photo-controlled, living radical polymerizations. See, Bratton, Polym. Adv. Technol. 2006, 17, 94-103; Madou, Fundamentals of Microfabrication and Nanotechnology, 3rd ed., CRC Press: Boca Raton, FL, 2011; ISBN 9780849331800; (c) Xu, Polym. J. 2018, 50, 45-55; Harris, Adv. Mater. 2005, 17, 39-42; Weitekamp, J. Am. Chem. Soc. 2013, 135, 16817-16820; Teator, Chem. Rev. 2016, 116, 1969-1992; Chen, Chem. Rev. 2016, 116, 10167-10211; Fors, Angew. Chem. Int. Ed. 2012, 51, 8850-8853; Anastasaki, J. Am. Chem. Soc. 2014, 136, 1141-1149; Treat, J. Am. Chem. Soc. 2014, 136, 16096-16101; Pan, J. Am. Chem. Soc. 2015, 137, 15430-15433.

Figure 2:
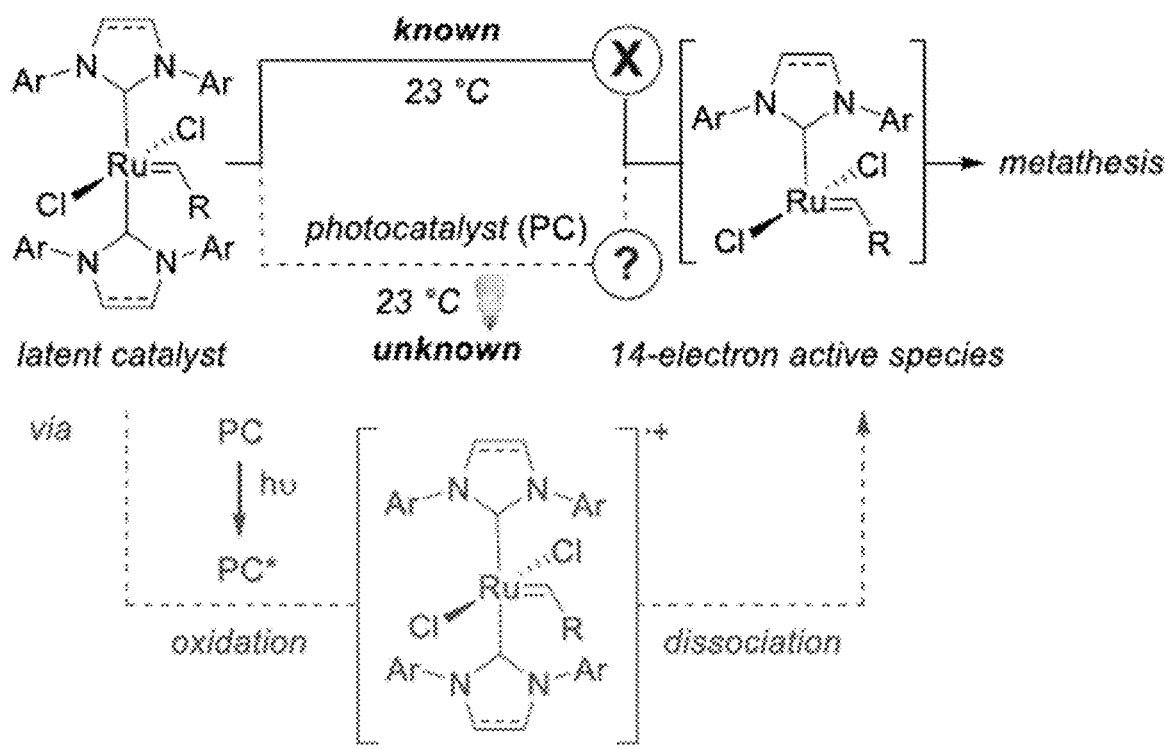
FIG. 2 is a schematic showing bis(NHC)-ruthenium complexes as latent catalysts using visible light.

At the outset of these studies, we needed a ruthenium-based complex that is inactive at ambient temperature, and identified bis-NHC ligated Ru complexes first introduced by Herrmann. See, Weskamp, Chem. Int. Ed. 1998, 37, 2490-2492. When substituted with aromatic groups on the nitrogen atoms, these catalysts lack activity for metathesis at room temperature, most probably because of the difficult dissociation of one NHC ligand to generate the corresponding 14-electron active catalyst. See, Trnka, J. Am. Chem. Soc. 2003, 125, 2546-2558. At higher temperatures, the activity of these catalysts is restored. In this regard, we surmised that the NHC dissociation event could be promoted at room temperature by using photoredox catalysis. A carefully chosen photocatalyst should be capable, after excitation upon irradiation with visible light, of activating these catalysts and therefore toggling them into their corresponding active species after dissociation of one NHC (FIG. 2).

To test our hypothesis, we first evaluated the benchmark ring closing metathesis (RCM) of diethyl diallylmalonate using $RuCl_2(CHPh)(IMes)_2$ and $RuCl_2(CHPh)(SIMes)_2$, previously reported by Fogg and Grubbs, in the presence of different photocatalysts under visible-light irradiation. See, Trnka cited above and Conrad, Organometallics 2003, 22, 1986-1988. After screening several photocatalysts and reaction conditions (see Example 2 for further details), we found that a combination of $RuCl_2(CHPh)(IMes)_2$ ($Ru_1$) and 2,4,6-triphenylpyrylium tetrafluoroborate (TPPT) as photocatalyst gives the desired product in 87% yield after 4 h of irradiation under blue LEDs at room temperature (Table 1, entry 9). While screening photocatalysts, we observed that only highly oxidizing ones such as acridinium and pyrylium derivatives provide some reactivity (entries 6-8), while no product is observed when switching to less oxidizing photocatalysts (entries 1-5). This is consistent with an activation mode involving oxidation of the Ru catalyst followed by dissociation of one NHC to generate the catalytically active species forming the corresponding radical cation. See, Eelman, Angew. Chem. Int. Ed. 2008, 47, 303-306; and Bailey, ACS Catal. 2016, 6, 4962-4971. We indeed note that Ru1 has two distinct oxidation events as identified by cyclic voltammetry, with the first occurring at +0.44 V, likely corresponding to the generation of the radical cation by a metal-centered oxidation (see Example 2). While all photoredox catalysts should allow oxidation to the radical cation, the dissociation event might be caused by a second oxidation occurring at one NHC ligand that would only be promoted by highly oxidizing photocatalysts and explain that traditional Ir and Ru photocatalysts are not effective (see table 1, entries 1-5). See, Ramnial, Chem. Commun. 2004, 1054-1055. Importantly, no reaction is observed in the absence of ruthenium, light or photocatalyst (entries 10-12). The lack of reactivity under light without photocatalyst also rules out a mechanism solely based on photo-induced dissociation of one NHC ligand and highlights the importance of the photoredox system. Finally, the use of $RuCl_2(CHPh)(SIMes)_2$ ($Ru_2$) delivers similar reactivity (entry 13). However, background reactivity is observed in the absence of light and photocatalyst (entry 14), indicating that dissociation of one NHC happens slowly at ambient temperature. $RuCl_2(CHPh)(IMes)_2$ (Ru1) was chosen as it displays optimal latent behavior.

TABLE 1

Reaction optimization and scope of RCM, CM, and ROCM reactions.

(1) Reaction Optimization

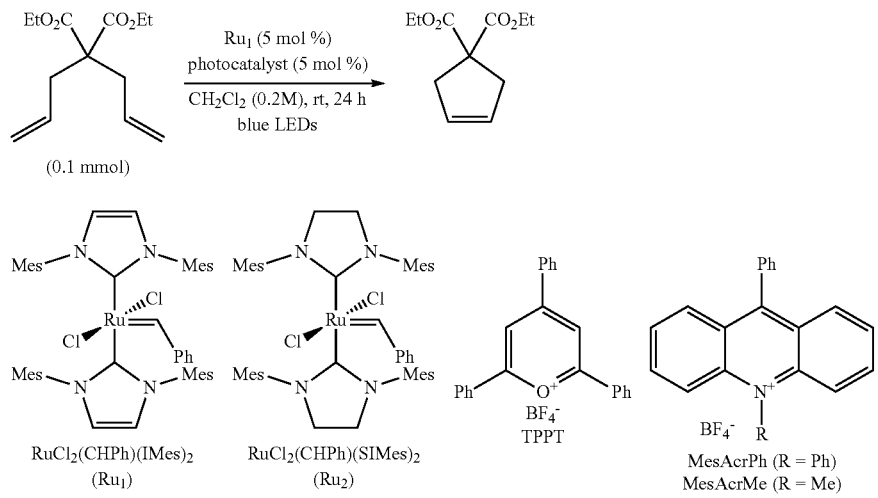

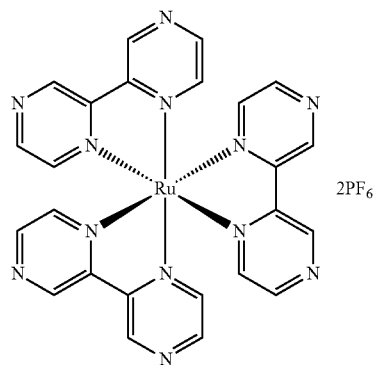

Ru(bpz)₃(PF₆)₂

| Entry | Conditions | $E_{ox}$* (V vs. SCE) | Yield[b] (%) |
|---|---|---|---|
| 1 | Ir(ppy)₃ | 0.31 | 0 |
| 2 | [Ir(ppy)₂(dtbbpy)]PF₆ | 0.66 | 0 |
| 3 | Ru(bpy)₃Cl₂ | 0.77 | 0 |
| 4 | [Ir(dF—CF₃ppy)₂(dtbbpy)]PF₆ | 1.21 | 0 |
| 5 | Ru(bpz)₃Cl₂ | 1.45 | 0 |
| 6 | MesAcrPh | 2.12 | 33 |
| 7 | MesAcrMe | 2.18 | 16 |
| 8 | TPPT | 2.66 | 84 |
| 9 | Ru₁ (2 mol %), TPPT (3 mol %), 4 h | — | 87 |
| 10 | No Ru₁ | — | 0 |
| 11 | No light | — | 0 |
| 12 | No photocatalyst | — | 0 |
| 13 | Ru₂ instead of Ru₁ | — | 75 |
| 14 | Ru₂, no light, no photocatalyst | — | 15 |
|  | Ru(bpz)₃(PF₆)₂ |  | 17 |

(b) Scope of RCM reactions[c]

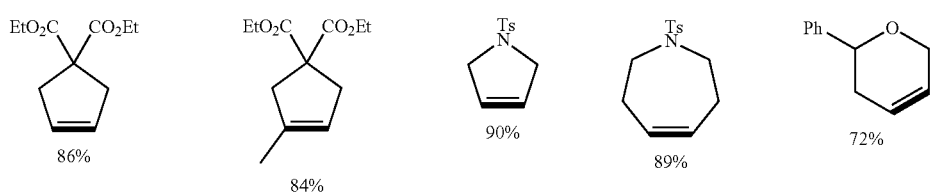

TABLE 1-continued

Reaction optimization and scope of RCM, CM, and ROCM reactions.

(1) Reaction Optimization

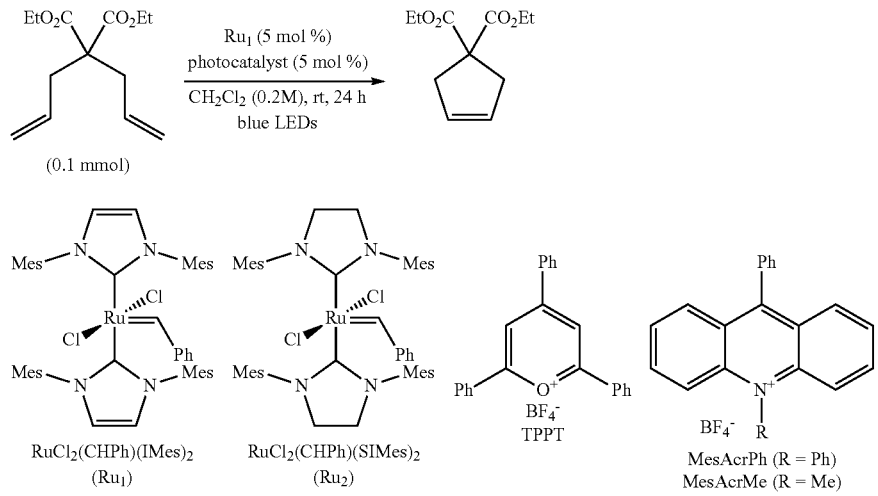

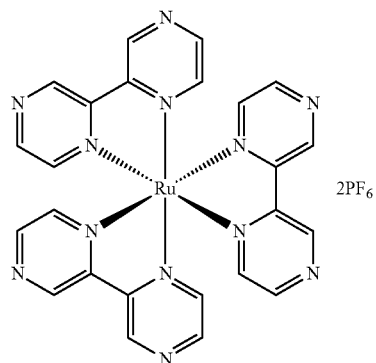

Ru(bpz)$_3$(PF$_6$)$_2$

| Entry | Conditions | $E_{ox}$* (V vs. SCE) | Yield[b] (%) |
|---|---|---|---|
| (c) Scope of CM and ROCM reactions[c] | | | |
| | Ph⁀⁀ + ⁀CO$_2$Me → Ph⁀⁀CO$_2$Me | | 60%[d,e] |
| | BzO⁀⁀⁀ + AcO⁀⁀⁀OAc → BzO⁀⁀⁀⁀OAc | | 70%[d,e] |
| | ⁀()$_4$OAc + styrene-F → ArCH=CH⁀()$_4$OAc | | 46%[d,e] |
| | cyclooctene + ⁀CO$_2$Me → MeO$_2$C⁀⁀()$_6$⁀⁀CO$_2$Me | | 51%[d,f] |

[a]All optimization reactions were conducted on a 0.1 mmol scale,
[b]Determined by $^1$H NMR spectroscopy using 1,2-dibromoethane as an internal standard.
[c]Conditions: substrate (0.2 mmol), RuCl$_2$(CHPh)(IMes)$_2$ (2 mol %), TPPT (3 mol %), CH$_2$Cl$_2$ (0.2M), rt, blue LEDs, 4 h.
[d]4 mol % of TPPT.
[e]Left substrate (0.2 mmol), right substrate (0.4 mmol).
[f]Left substrate (0.2 mmol), right substrate (0.6 mmol).
[g]For additional samples, see Example 2.

With an efficient system in hand, we first explored its ability to promote different types of metathesis reactions. While standard metathesis reactions can be readily promoted using this photoredox catalytic system, as illustrated with representative examples in Table 1 and Example 2, we were more interested in interrogating ring-opening metathesis polymerization (ROMP) applications. To this end, several monomers such as norbornene derivatives 1-8,11, norbornadiene 9,1,5-cyclooctadiene 10 and dicyclopentadiene 12 could be readily polymerized within 1 h under blue LED irradiation in the presence of $RuCl_2(CHPh)(IMes)_2$ and TPPT (Table 2).

TABLE 2

Scope of ROMP reactions.

| Entry | Monomer | Conversion[b] (%) | Theo. $M_n$ (kDa) | Exp. $M_n$[c] (kDa) | Đ[c] |
|---|---|---|---|---|---|
| 1 | 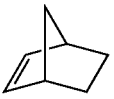 | >95 | 18.8 | 99.6 | 1.88 |
| 2 | 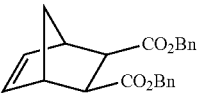 [SMILES: O=C(OCc1ccccc1)C1C2C=CC(C2)C1C(=O)OCc1ccccc1] | >95 | 66.9 | 215.2 | 1.66 |
| 3 | 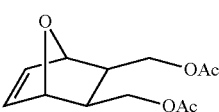 [SMILES: CC(=O)OCC1C2C=CC(O2)C1COC(C)=O] | >95 | 48.0 | 327.4 | 1.63 |
| 4 | 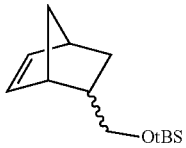 | >95 | 47.7 | 424.8 | 1.84 |
| 5 | 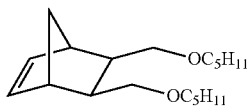 | | | | |
| 6 | 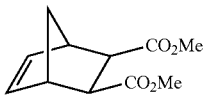 [SMILES: COC(=O)C1C2C=CC(C2)C1C(=O)OC] | 40-60 | | | |
| 7 | 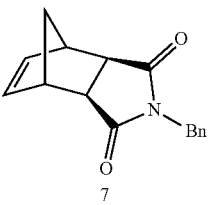 [SMILES: O=C1[C@@H]2C3C=CC(C3)[C@@H]2C(=O)N1Cc1ccccc1] | 65 | | | |
| 8 | 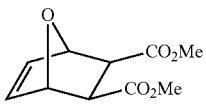 [SMILES: COC(=O)C1C2C=CC(O2)C1C(=O)OC] | | | | |
| 9 | 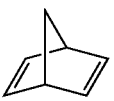 | 99 | | 14.4 | |
| 10 | 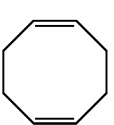 | 99 | | | |

TABLE 2-continued

Scope of ROMP reactions.

| Entry | Monomer | Conversion[b] (%) | Theo. $M_n$ (kDa) | Exp. $M_n$[c] (kDa) | Đ[c] |
|---|---|---|---|---|---|
| 11 | | | | | |
| 12[d] | | 99 | | | |
| 13 | | >80 | 66.9 | 214.2 | 1.67 |
| 14 | | | | | |
| 15 | | | | | |
| 16 | | | | | |
| 17 | | | | | |
| 18 | | | | | |
| 19 | | | | | |
| 20 | | | | | |

TABLE 2-continued

Scope of ROMP reactions.

| Entry | Monomer | Conversion[b] (%) | Theo. $M_n$ (kDa) | Exp. $M_n$[c] (kDa) | Đ[c] |
|---|---|---|---|---|---|
| 21 | norbornene-OBoc structure | | | | |
| 22 | dicyclopentane-fused norbornene | >80 | 26.8 | 48.1 | 1.32 |
| 23 | indane-fused norbornene | | | | |
| 24 | oxanorbornene with two $OC_5H_{11}$ groups | | | | |
| 25 | cyclooctene | 99 | | 5 | |

[a]Conditions: monomer (0.2 mmol), $RuCl_2(CHPh)(IMes)_2$ (0.5 mol %), TPPT (1 mol %), $CD_2Cl_2$ (0.2M), rt, blue LEDs, 1 h.
[b]Determined by $^1H$ NMR spectroscopy using mesitylene as internal standard.
[c]Determined by GPC.
[d]Using $IMes_2RuCl_2CHPh$ (0.01 mol %), TPPT (0.05 mol %) for 15 min under blue LEDs.

Molecular weights (Mn) obtained after polymerization of monomers 1-4 are significantly higher than the expected values which suggests that polymerization is faster than catalyst initiation. Dispersities were found in the range of 1.63 to 1.88. Monomers 5-10 are also smoothly polymerized within an hour of irradiation but lead to insoluble polymers, which precludes GPC analysis. Finally, cross-linking monomers 11 and 12 could also be efficiently polymerized to afford complete gelation within an hour, the latter only requiring 0.01 mol % of Ru1, 0.05 mol % of TPPT and 15 minutes of irradiation. Importantly, the latency is successfully maintained with dicyclopentadiene 12 since, in the absence of light, less than 5% polymerization is observed after 24 h (5% after 3 days, 9% after a week). When stopped after 90 seconds under light, 16% polymerization is observed. The rate of polymerization under visible light can therefore be estimated to be 12,000 times faster than in the dark.

Figure 3:
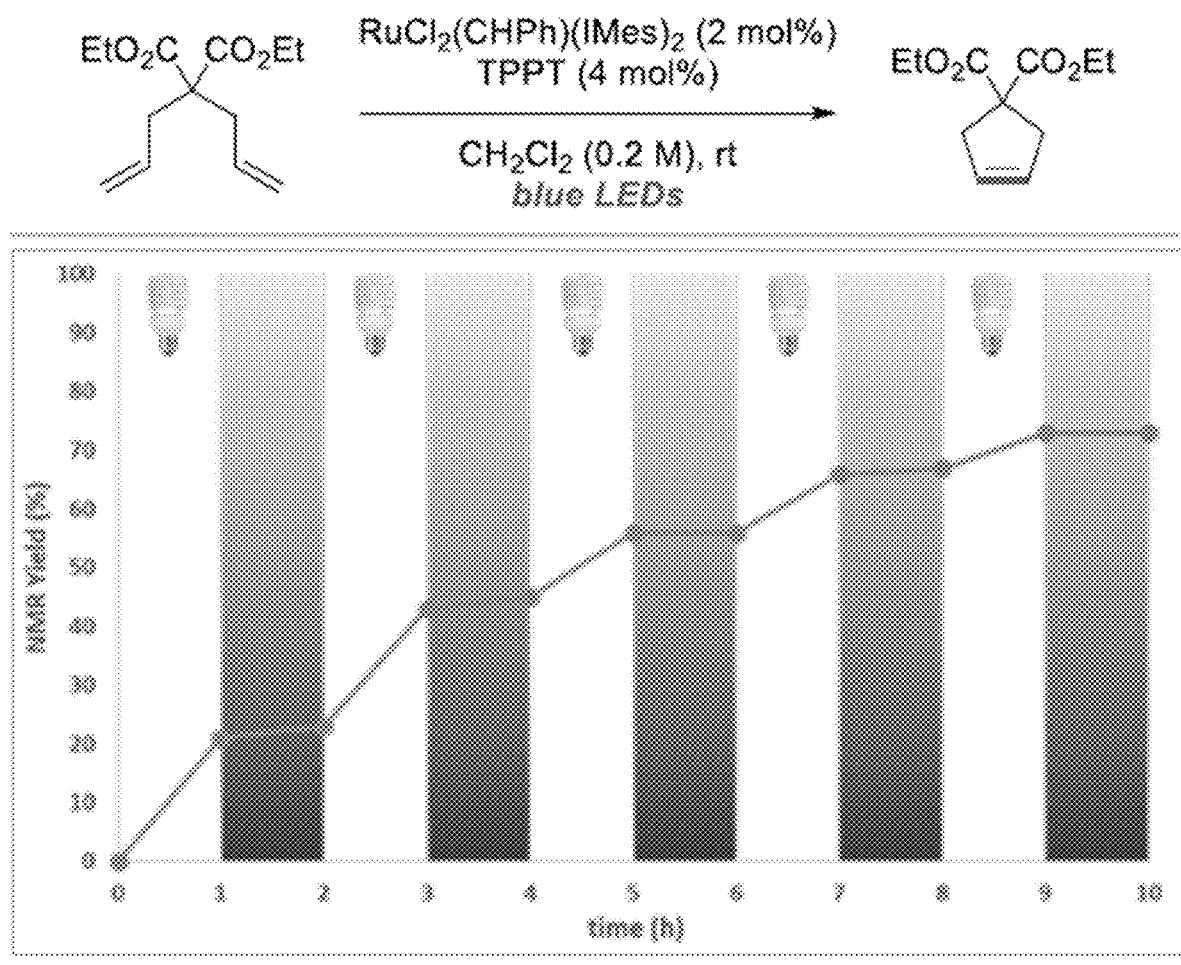
FIG. 3 is a schematic and bar graph showing temporal control over the RCM of diethyl diallylmalonate and corresponding proposed mechanism.
Figure 4:
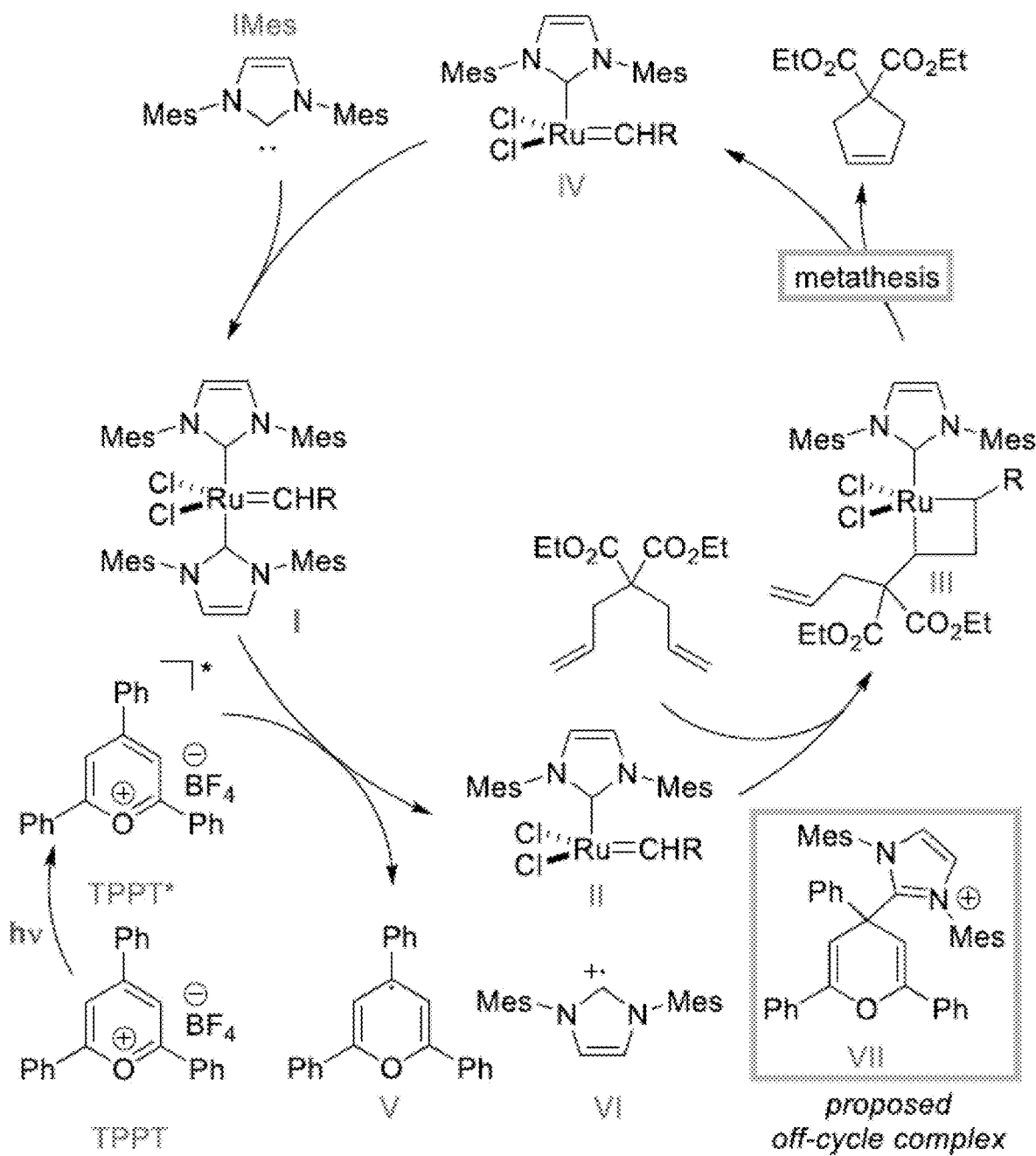
FIG. 4 is a schematic showing the proposed catalytic cycle.
Figure 5:
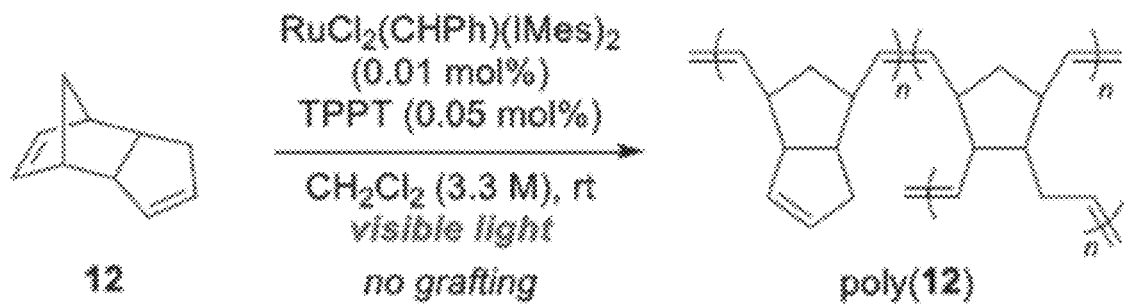
FIG. 5 is a reaction scheme showing the macroscopic patterning of poly(dicyclopentadiene).
Figures 6A, 6B, 6C:
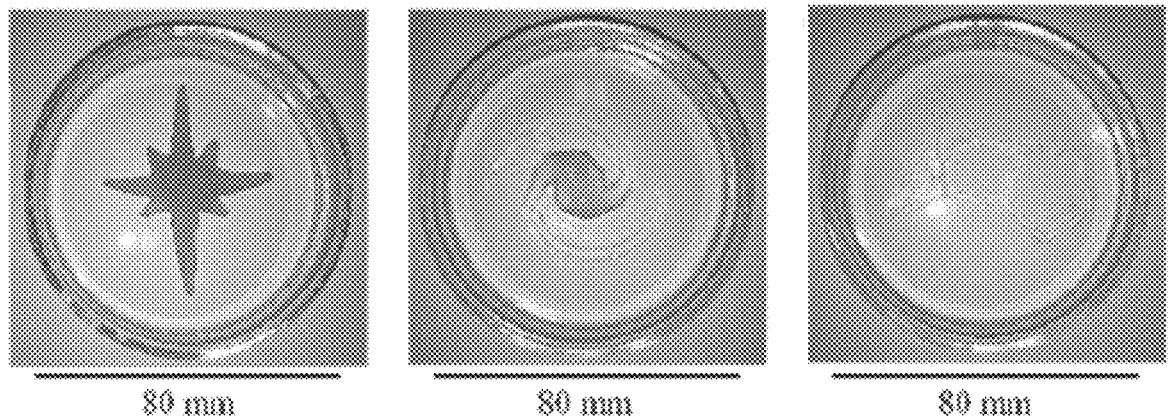
FIGS. 6A-6C are photographs of polymer patterning and photolithographic olefin metathesis polymerization (PLOMP) using visible light, photomasks, and a blue LED (40 W, Kessil).

Further experiments were conducted to examine the influence of light and to probe our ability to exert temporal and spatial controls over the reaction. First, temporal control was evaluated by conducting on/off experiments with alternating periods of irradiation and darkness for the ring closing metathesis of diethyl diallylmalonate. The ability to exert temporal control over a reaction is of great interest for the design of orthogonal multicomponent reactions, as well as for the development of new systems designed to produce new highly functionalized materials. As can be seen in FIGS. 3 and 4, temporal control can be achieved since maximal reactivity was obtained during irradiation whereas darkness only afforded minimal increases in yields (from 0 to 3%).

A series of experiments lead us to suggest the following mechanism for the on/off behavior enabled by photoredox catalysis and light irradiation. See, Ogawa cited above. It is commonly accepted that Ru catalysts mediate olefin metathesis via a coordinatively unsaturated Ru(II) intermediate such as II (FIGS. 3 and 4). Given that only highly oxidizing excited state photocatalysts provide appreciable yield (Table 1), we propose that ligand loss occurs at ambient temperature from an oxidized Ru intermediate, potentially at the IMes moiety to give active metathesis catalyst II and reduced pyrylium V as well as VI. The latter two can combine to form VII, analogous to adducts reported lacking substitution at the 4 position. Release of the IMes provides a pool of free ligand which can coordinate IV and arrest catalysis. See, Antoni, J. Am. Chem. Soc. 2018, 140, 14823-14835; and Branchi, J. Org. Chem. 2004, 69, 8874-8885.

We also interrogated our ability to exert spatial control over metathesis with this system, due to the potential applications in materials science with polymer patterning, 3D printing and photolithography. In this regard, the development of a system controlled by visible light appears especially attractive and convenient. To this end, dicyclopentadiene 12, and some other monomers, were first irradiated with visible light (blue Kessil lamp, 40 W) in the presence of RuCl$_2$(CHPh)(IMes)$_2$ and TPPT through different photomasks in order to produce macroscopic polymers with controlled geometric patterns. Similar patterning could be obtained with: norbornadiene 9, 1,5-cyclooctadiene 10 and 5-ethylidene-2-norbornene 11. Removal of the masks and unreacted monomers nicely affords the corresponding patterned polymers in short irradiation times (15-60 minutes) and with minimal bleeding in the unexposed areas (FIGS. 5-9). The amount of monomer consumed that is not present in the final patterned polymer was estimated at 7% by analysis of the wash using an external reference. Interestingly, the thickness of these patterned polymers can be easily controlled by tuning the irradiation time (see Example 2). Finally, an important feature of this system is its practicality and user-friendliness. While the excited state TPPT* is modestly sensitive to oxygen, the photomask patterning experiments can be performed with minimal precautions of placing the monomer/catalyst mixture under a blanket of inert gas.

Figures 7A, 7B, 7C:
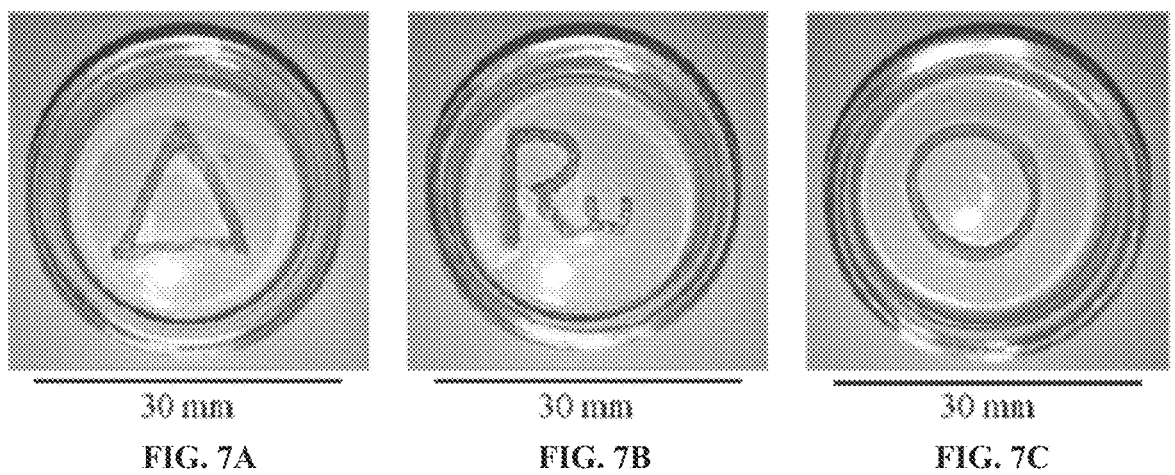
FIGS. 7A-7C are photographs of polymer patterning and photolithographic olefin metathesis polymerization (PLOMP) using visible light and blue laser pointer (200 mW).
Figure 8:
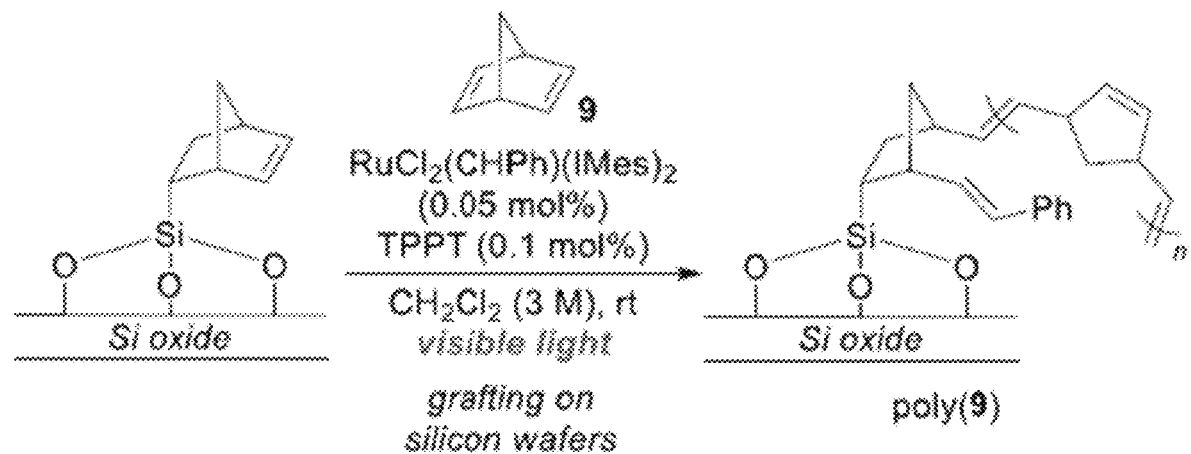
FIG. 8 is a reaction scheme showing the microscopic patterning of poly(norbornadiene) via PLOMP.

Higher resolutions are required in order to apply this visible-light-controlled system for applications in Photo-Lithographic Olefin Metathesis Polymerization (PLOMP). While most photolithographic techniques are based on the use of high resolution photomasks, an attractive alternative is the use of high resolution light sources, such as lasers, which should provide a straightforward way to reach pin-point resolution and find new applications in photolithography. See, Rühe, ACS Nano 2017, 11, 8537-8541. As proof of concept, we could successfully induce similar patterning from dicyclopentadiene solutions using a simple blue laser pointer (200 mV). In these cases, the patterns are directly and conveniently "drawn" from the bulk solution in a few minutes, either manually (FIGS. 7A and 7B) or using an orbital shaker providing constant movement (FIG. 7C).

Figure 9A:
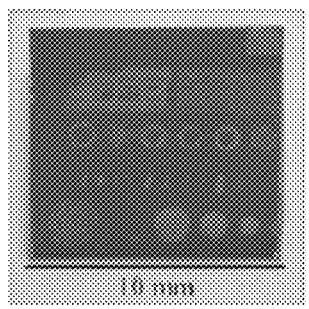
FIGS. 9A-9C are photographs showing polymer patterning and photolithographic olefin metathesis polymerization (PLOMP) using visible light and photomasks and a blue LED (40 W, Kessil).
Figure 9B:
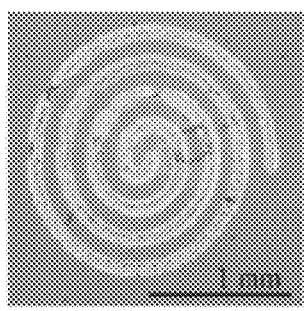
Figure 9C:
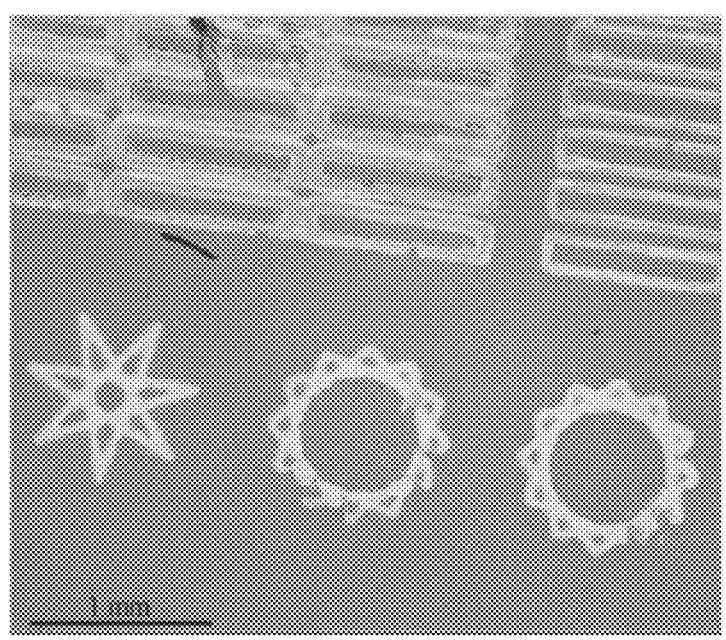

The two afore-described techniques allow the convenient fabrication of macroscopic patterned polymers through spatially-resolved ROMP promoted by visible light and without the need for grafting of the monomers. As for microscopic patterning, we also demonstrate the efficiency of our system for PLOMP applications. Although photolithography is now a commonly used technique in microfabrication, such systems based on olefin metathesis are still rare. To this end, 1 cm×1 cm silicon wafers were first pre-functionalized with a norbornene unit to ensure grafting of the growing polymer onto the surface. See, Harris and Weitekamp cited above. Those pre-functionalized silicon wafers were then used as support to perform the spatially-resolved polymerization of norbornadiene on a microscale by simply irradiating a solution of the monomer, RuCl$_2$(CHPh)(IMes)$_2$ and TPPT in dichloromethane with a regular blue LED light bulb (blue Kessil lamp, 40 W) through high resolution photomasks (FIG. 9A).

Example 2

General Information.

All reactions were carried out in oven-dried glassware under an argon or nitrogen atmosphere employing standard techniques in handling air-sensitive materials.

All solvents were reagent grade. Dichloromethane (anhydrous, >99.8%), hexane (anhydrous, 95%), pyridine (anhydrous, 99.8%) and toluene (anhydrous, 99.8%) were purchased from Sigma-Aldrich and used as supplied. Benzene (anhydrous, 99.8%) was purchased from Merck and used as supplied. Grubbs 1st and 2nd generation catalysts and SIMes were purchased from Sigma Aldrich and used as supplied. IMes was purchased from TCI Chemicals and used as supplied. All photocatalysts used were either synthesized by known methods or bought from commercial sources. 2,4,6-Triphenylpyrylium tetrafluoroborate in particular was purchased from Sigma Aldrich and used as supplied. Trichloro(5-norbornen-2-yl)silane was synthesized based on a reported procedure.1 All other reagents were used as supplied.

All photochemical reactions were performed in 1-dram vials fitted with Teflon caps under irradiation with two blue PR160-440 nm Kessil 40 W LED lamps. Reactions were magnetically stirred and monitored by thin layer chromatography using SiliCycle® 250 μm 60 Å plates. Flash chromatography was performed with silica gel 60 Å (particle size 40-63 μm) supplied by SiliCycle®. Yields refer to chromatographically and spectroscopically pure compounds unless otherwise stated.

All polymer patterning experiments were performed in BRAND® petri dishes (glass, 40 mm×12 mm or 80 mm×15 mm) purchased from Sigma Aldrich. A UKing ZQ-J33 200 mW 532 nm & 450 nm double light 5 in 1 USB laser pointer was purchased from www.laserpointerpro.com. Silicon wafers (4", 2850 Å oxide layer, resistivity 0.001-.005 ohm-cm, p-type, orientation <100>) were purchased from NOVA Electronic Materials (Item #H539626-OX). Masks were drawn in CAD software and printed by CAD/ART Services, Inc. (Brandon, OR).

Proton NMR spectra were recorded using an internal deuterium lock at ambient temperature on a Bruker 500 MHz spectrometer. Internal reference of $\delta_H$ 7.26 was used for CDCl3. Data are presented as follows: chemical shift (in ppm on the δ scale relative to $\delta_{TMS}$=0), multiplicity (s=singlet, d=doublet, t=triplet, q=quartet, m=multiplet, br.=broad, app.=apparent), coupling constant (J/Hz) and integration. Resonances that are either partially or fully obscured are denoted obscured (obs.). Carbon-13 NMR spectra were recorded at 125 MHz using CDCl$_3$ ($\delta_C$ 77.16) as internal reference. Fluorine-19 NMR spectra were recorder at 470 MHz using CF$_3$CH$_2$OH ($\delta_F$—77.59) as external reference.

High-resolution mass spectra were obtained on a Waters XEVO G2XSQToF mass spectrometer. Infrared spectra were recorded on a Perkin Elmer Spectrum Two FT-IR Spectrometer. GPC analysis were performed on an Agilent 1260 Infinity GPC using 2×300 mm Agilent PLGel Mixed-D columns and G1362A RI or G1365D multiwavelength detectors, calibrated against polystyrene standards.

All cyclic voltammetry studies were performed on a CH instruments Model 1232B potentiostat using an EDAQ 1-mm disk glassy carbon working electrode in conjunction with an EDAQ Ag/AgCl reference electrode and a platinum wire from VWR as counter electrode. All experiments were performed in anhydrous dichloromethane (RuCl$_2$(CHPh)(IMes)$_2$ and RuCl$_2$(CHPh)(SIMes)$_2$) or tetrahydrofuran (free IMes and free SIMes) at 5 mM using tetrabutylammonium hexafluorophosphate (0.1 M) as electrolyte. The scan rate was set at 100 mV/s.

Plasma treatments were conducted using a PE-50 Compact Benchtop Plasma Cleaning System manufactured by Plasma Etch, Inc. Micrographs of the patterned silicon wafers were recorded on a Nikon Eclipse LV150N microscope. Step heights were measured by imaging 10 μm sections (0.5 Hz, 256 samples/line) on a Bruker Dimension Icon AFM using a Scanasyst-Air probe in Scanasyst mode.

A. Synthesis of RuCl$_2$(CHPh)(IMes)$_2$ (i) Synthesis of RuCl$_2$(CHPh)(PCy$_3$)(IMes)

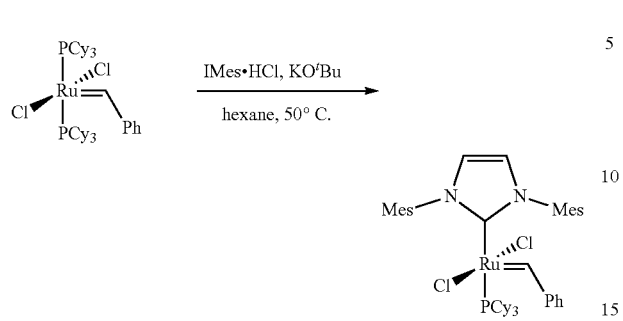

RuCl$_2$(CHPh)(PCy$_3$)(IMes) was synthesized as described in Jafarpour, Organometallics, 2000, 19, 2055-2057. In a glovebox, a 50 mL round bottom flask was charged with Grubbs 1st generation (1.5 g, 1.82 mmol), IMes.HCl (933 mg, 2.73 mmol), KOtBu (450 mg, 4.0 mmol) and anhydrous hexane (15 mL). The flask was sealed and removed from the glovebox before stirring at 50° C. for 5 h. The resulting suspension was cooled to room temperature and filtered through a collection frit. The precipitate was finally washed with water and a minimal amount of hexane before being dried under vacuum to afford the desired RuCl$_2$(CHPh)(PCy$_3$)(IMes) as a purple-brown solid (846 mg, 1.0 mmol, 67% yield). The NMR data are in agreement with the literature values.

(ii) Synthesis of RuCl$_2$(CHPh)(Py)$_2$(IMes)

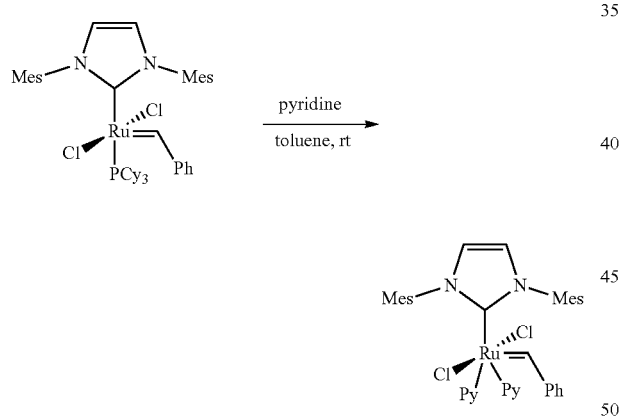

RuCl$_2$(CHPh)(Py)$_2$(IMes) was synthesized as described in Sanford, Organometallics, 2001, 20, 5314-5318. In a glovebox, RuCl$_2$(CHPh)(PCy$_3$)(IMes) (846 mg, 1 mmol) was dissolved in anhydrous toluene (2.5 mL) and pyridine (6.5 mL). The reaction mixture was stirred for 30 min at room temperature. During that time, a quick change in color from red to green could be observed. The reaction mixture was then concentrated under vacuum before pentane was added. The green residue was triturated in pentane and allowed to precipitate for 30 minutes at −20° C. The precipitate was then filtered, washed with cold pentane (−20° C.) and finally dried under vacuum to afford RuCl$_2$(CHPh)(Py)$_2$(IMes) as a green solid (689 mg, 0.95 mmol, 95% yield). The NMR data are in agreement with the literature values.

(iii) Synthesis of RuCl$_2$(CHPh)(IMes)$_2$

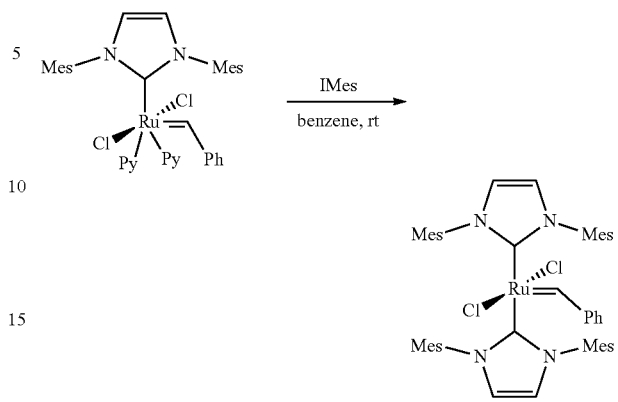

RuCl$_2$(CHPh)(IMes)$_2$ was synthesized as described in Bantreil, Nat. Protoc., 2011, 6, 69-77. In a glovebox, a 100 mL round bottom flask was charged with RuCl$_2$(CHPh)(Py)$_2$(IMes) (944 mg, 1.30 mmol), IMes (397 mg, 1.30 mmol) and anhydrous benzene (50 mL). The brown reaction mixture was stirred overnight at room temperature, filtered and concentrated under vacuum. The crude residue was then precipitated from cold pentane (−20° C.), filtered and washed with cold pentane (−20° C.). To improve its purity, the complex was extracted multiple times with boiling hexanes. The precipitate was therefore taken up in boiling hexanes and filtrated through a collection frit. This was repeated multiple times to recover most of the desired complex. The combined organic layers were finally concentrated under vacuum to afford the desired RuCl$_2$(CHPh)(IMes)$_2$ as a brown solid (670 mg, 0.77 mmol, 59% yield). The NMR data are in agreement with the literature values.

B. Synthesis of RuCl$_2$ (CHPh)(SIMes)$_2$ (i) Synthesis of RuCl$_2$(CHPh)(Py)$_2$SIMes

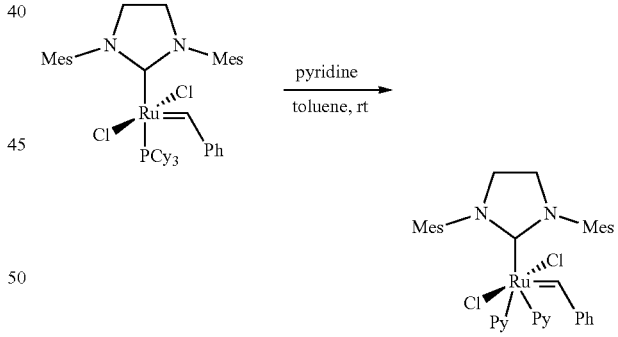

RuCl$_2$(CHPh)(Py)$_2$(SIMes) was synthesized as described in Sanford cited above. In a glovebox, Grubbs 2nd generation (250 mg, 294 μmol) was dissolved in anhydrous toluene (750 μL) and pyridine (1.8 mL). The reaction mixture was stirred for 30 min at room temperature. During that time, a quick change in color from red to green could be observed. The reaction mixture was then poured into cold pentane (−20° C.) inducing precipitation of a green solid. The solid was allowed to fully precipitate for 30 minutes at −20° C. before being filtered, washed with cold pentane (−20° C.) and finally dried under vacuum to afford RuCl$_2$(CHPh)(Py)$_2$(SIMes) as a green solid (196 mg, 270 μmol, 92% yield). The NMR data are in agreement with the literature values.

(ii) Synthesis of RuCl$_2$(CHPh)(SIMes)$_2$

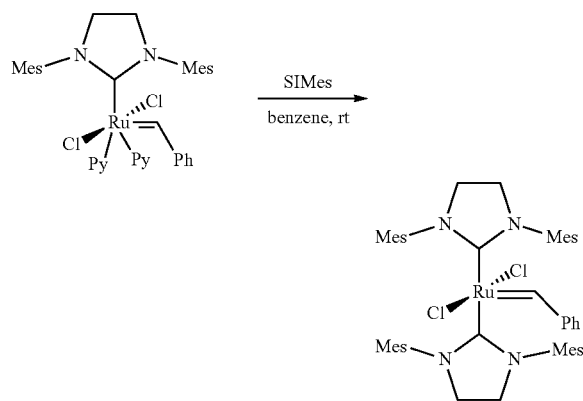

RuCl$_2$(CHPh)(SIMes)$_2$ was prepared as described in Trnka, J. Am. Chem. Soc., 2003, 125, 2546-2558. In a glovebox, a 25 mL round bottom flask was charged with RuCl$_2$(CHPh)(Py)$_2$(SIMes) (196 mg, 270 μmol), SIMes (83 mg, 270 mmol) and benzene (9 mL). The brown reaction mixture was stirred at 45° C. for 24 h before being cooled to room temperature and concentrated under vacuum. The crude residue was then precipitated from cold pentane (−20° C.), filtered and washed with cold pentane (−20° C.). To improve its purity, the complex was extracted multiple times with boiling hexanes. The precipitate was therefore taken up in boiling hexanes and filtrated through a collection frit. This was repeated multiple times to recover most of the desired complex. The combined organic layers were finally concentrated under vacuum to furnish the desired RuCl$_2$(CHPh)(SIMes)$_2$ as a brown solid (150 mg, 171 μmol, 63% yield). The NMR data are in agreement with the literature values.

Cyclic Voltammetry Studies

Cyclic voltammetry studies were run using a glassy carbon electrode, a platinum wire counter electrode and an Ag/AgCl reference electrode. For all studies, tetrabutylammonium hexafluorophosphate was used as the electrolyte in a solution of dichloromethane (RuCl$_2$(CHPh)(IMes)$_2$ and RuCl$_2$(CHPh)(SIMes)$_2$) or tetrahydrofuran (free IMes and free SIMes) while nitrogen was bubbled through the solution prior to data collection. Sweeps were run negative (reductive) on first pass.

The cyclic voltammograms of ruthenium complexes RuCl$_2$(CHPh)(IMes)$_2$ and RuCl$_2$(CHPh)(SIMes)$_2$ both display a pseudo-reversible oxidation at 0.47 V (0.44 V vs SCE) and 0.49 V (0.43 V vs SCE), respectively, which are most probably related to the Ru(II)/Ru(III) couple. In addition, oxidation events at high potentials (>1.8 V) are also observed on both cyclic voltammograms and are probably related to the oxidation of the carbene ligands. See, Tomar, Chem. Commun., 2018, 54, 9753-9756. These oxidation events do not appear to be reversible. While the first oxidation process should be accessible by most Ru- and Ir-based photocatalysts, the events at high potentials are only accessible by much oxidizing photocatalysts such as acridinium and pyrylium derivatives. As described on the next page, only those highly oxidizing photocatalysts display some reactivity.

Mechanistic Discussion

Proposed Mechanistic Cycle

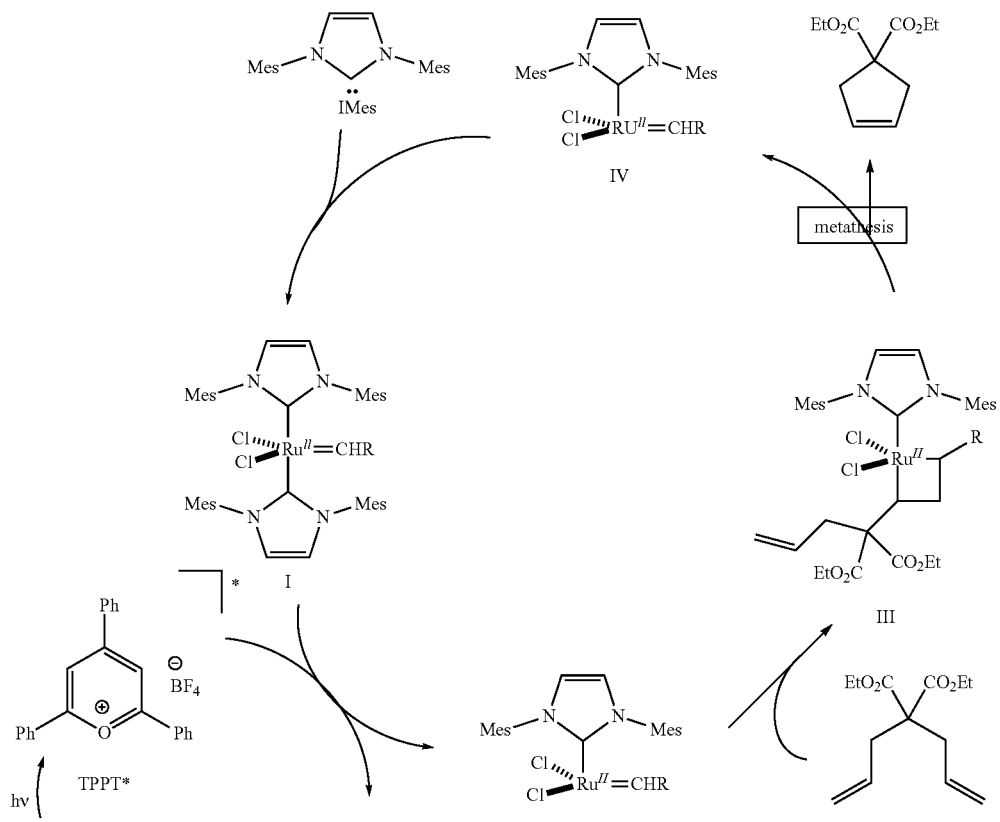

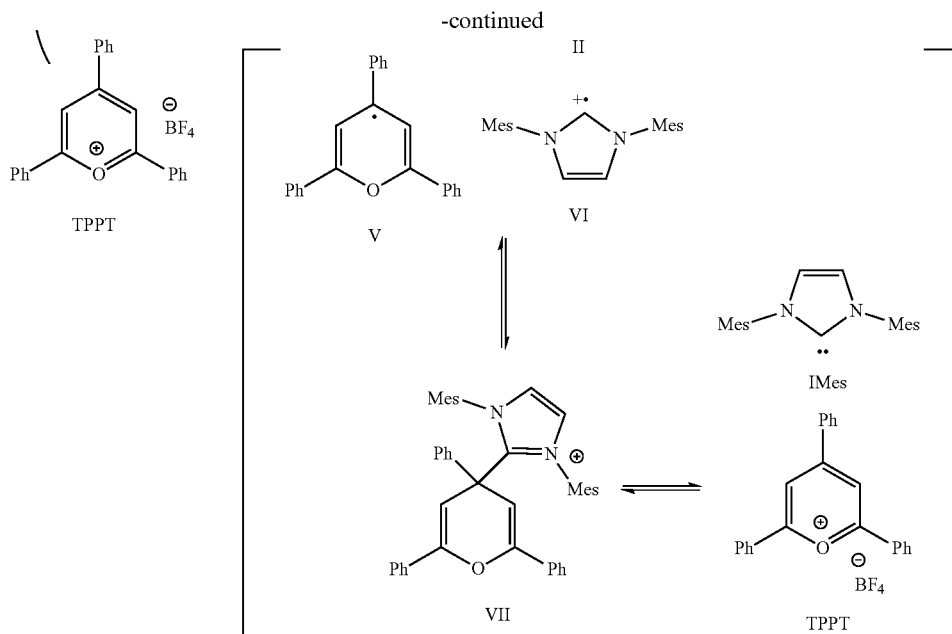

Evaluation of the optimized conditions and cyclic voltammetry support the above mechanisms. Given the high oxidation potential of the Ru catalyst and the necessity of a highly oxidizing photocatalyst we propose oxidation of the IMes ligand to liberate the active Ru(II) catalyst. Literature precedent of analogous redox couples with TPPT invoke formation of intermediate VII. See, Ogawa, J. Am. Chem. Soc., 2015, 137, 1400-1403.

Upon decomplexation, the ground state of TPPT is regenerated and the IMes can coordinate to IV. This complex formation between the reduced TPPT and oxidized IMes rationalizes the imperfect temporal control (0-3% increase during dark periods). TPPT is the optimal catalyst because it is highly oxidizing and lewis acidic, which is accounted for in the proposed mechanism.

NMR experiments probe the nature of the Ru catalysts/TPPT before and after light. A 1:1 solution of the TPPT/Ruthenium catalyst was evaluated over a 36 h period with 1H NMRs recorded every 10 min. Upon irradiation with blue light (5 min) NMR experiments were performed. Diagnostic TPPT peaks have diminished/broadened in the aromatic range. Over the course of the kinetic study new peaks appear to form ~4.8 ppm and ~8.0-8.1 ppm as TPPT appears to disappear after light irradiation. We believe this could be due to complexation between the TPPT and the IMes ligand to form intermediate VII. Further mechanistic studies are currently underway that model the reaction conditions more closely.

Comparison of Ruthenium and TPPT Catalysts Prior and after Blue Light Irradiation.

The $^1$H-NMR spectra of the following solutions were obtained and compared.

See, FIGS. 16-19.

(a) 1:1 TPPT RuCl$_2$(CHPh)(IMes)$_2$, 24 hours, after light
(b) 1:1 TPPT ruthenium catalyst, 1 minute after light
(c) 1:1 TPPT ruthenium catalyst, prior to light
(d) TPPT
(e) ruthenium catalyst These results illustrate that TPPT may complex to the ruthenium catalyst to form an intermediate VII.

Extended Optimization Studies: Screening of Photocatalysts

TABLE 3

| Photocatalyst | Excited state oxidation potential (V vs. SCE) | Excited state energy (kcal/mol) | Yield (%) |
|---|---|---|---|
| Ir(ppy)$_3$ | 0.31 | 55.20 | 0 |
| [Ir(ppy)$_2$(dtbbpy)]PF$_6$ | 0.66 | 49.21 | 0 |
| Ru(bpy)$_3$Cl$_2$ | 0.77 | 46.49 | 0 |
| Fluorescein | 0.77 | 44.74 | 0 |
| Rose Bengal | 0.81 | 41.51 | 0 |
| Eosin Y | 0.83 | 44.05 | 0 |
| Rhodamine B | 0.084 | 41.51 | 0 |
| Rhodamine 6G | 0.95 | 48.20 | 0 |
| Ir(dF—CF$_3$ppy)$_2$(dtbbpy)]PF$_6$ | 1.21 | 60.10 | 0 |
| 4CzIPN | 1.35 | n/a | 0 |
| Ru(bpz)3Cl$_2$ | 1.45 | 48.38 | 0 |
| TAPT | 1.84 | S$_1$: 53.96; T$_1$: 50.96 | 0 |
| MesAcrPhBFr | 2.12 | n/a | 33 |
| MesAcrMeClO$_4$ | 2.18 | S$_1$: 61.57; T$_1$: 44.74 | 8 |
| MesAcrMeBF$_4$ | 2.18 | S$_1$: 61.57; T$_1$: 44.74 | 16 |
| TPPT | 2.55 | S$_1$: 65.26; T$_1$: 53.04 | 84 |

Some known triplet sensitizers such as benzophenone, 4,4'-dimethoxybenzophenone, 4,4'-bis(dimethylamino)benzophenone (or Michler's ketone) and 9-fluorenone have also been investigated to promote the ring closing metathesis of diallyl diethylmalonate. As for most photocatalysts displayed in the above chart, no reaction was observed. See, Table 3.

Figure 9D:
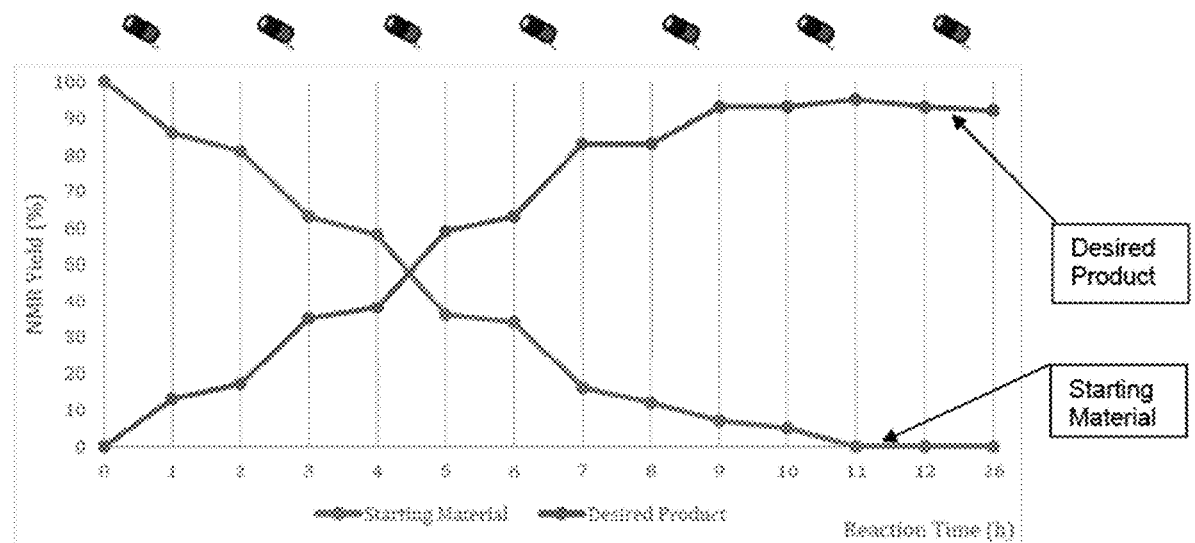
FIG. 9D is the on and off study for the RCM of dibenzyl diallylmalonate.
Figure 10:
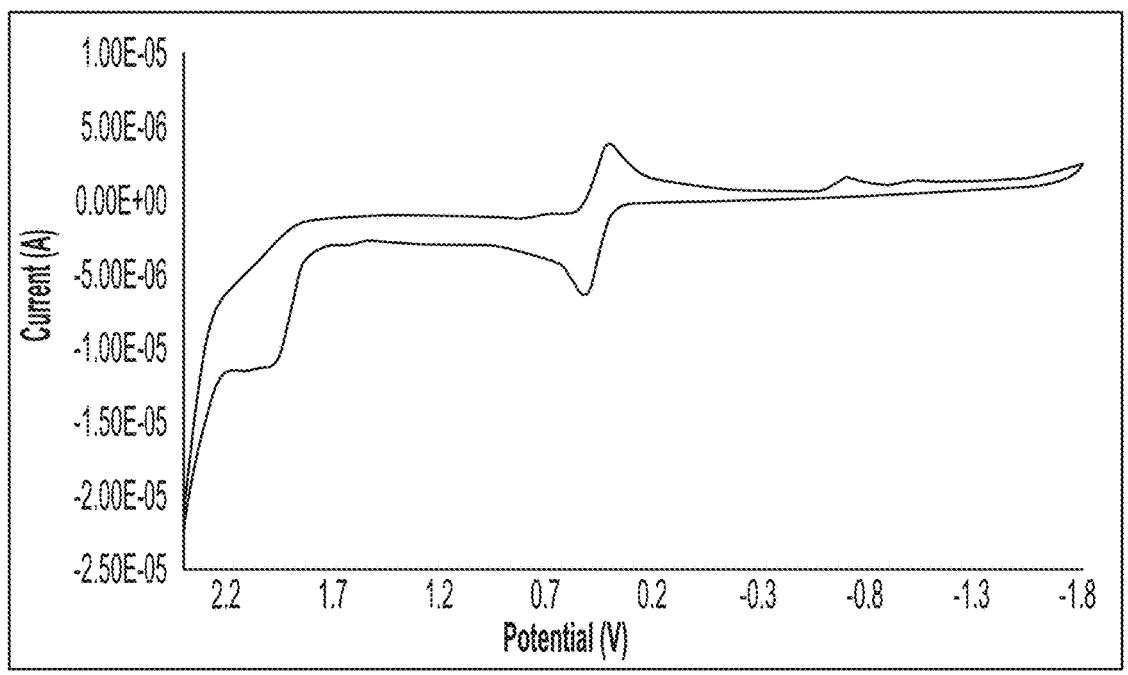
FIG. 10 is the cyclic voltammetry spectrum for $RuCl_2$(CHPh)(IMes)$_2$ versus Ag/AgCl.
Figure 11:
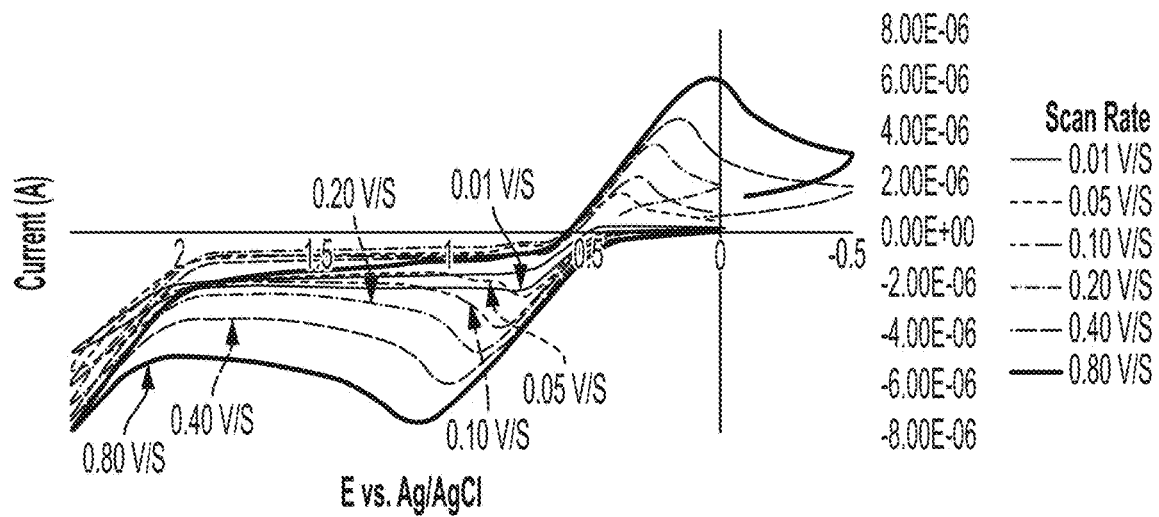
FIG. 11 is the cyclic voltammetry spectrum for $RuCl_2$(CHPh)(IMes)$_2$ versus Ag/AgCl (Differential Scan Rates—Cyclic Voltammetry).
Figure 12:
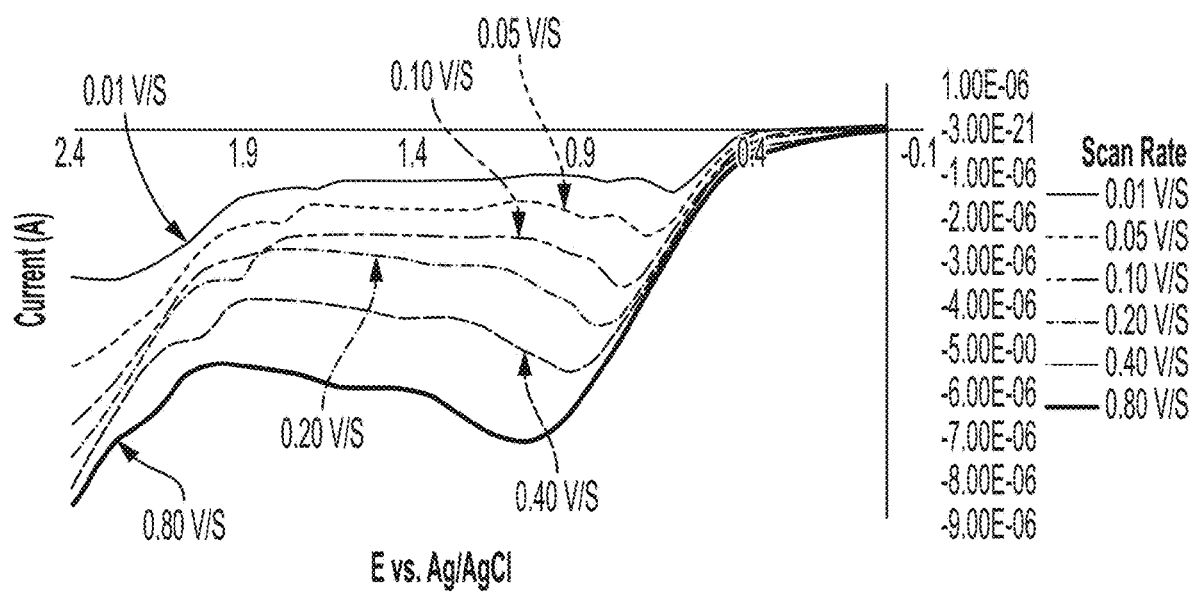
FIG. 12 is the cyclic voltammetry spectrum for $RuCl_2$(CHPh)(IMes)$_2$ versus Ag/AgCl (Differential Scan Rates—Linear Voltammetry).
Figure 13:
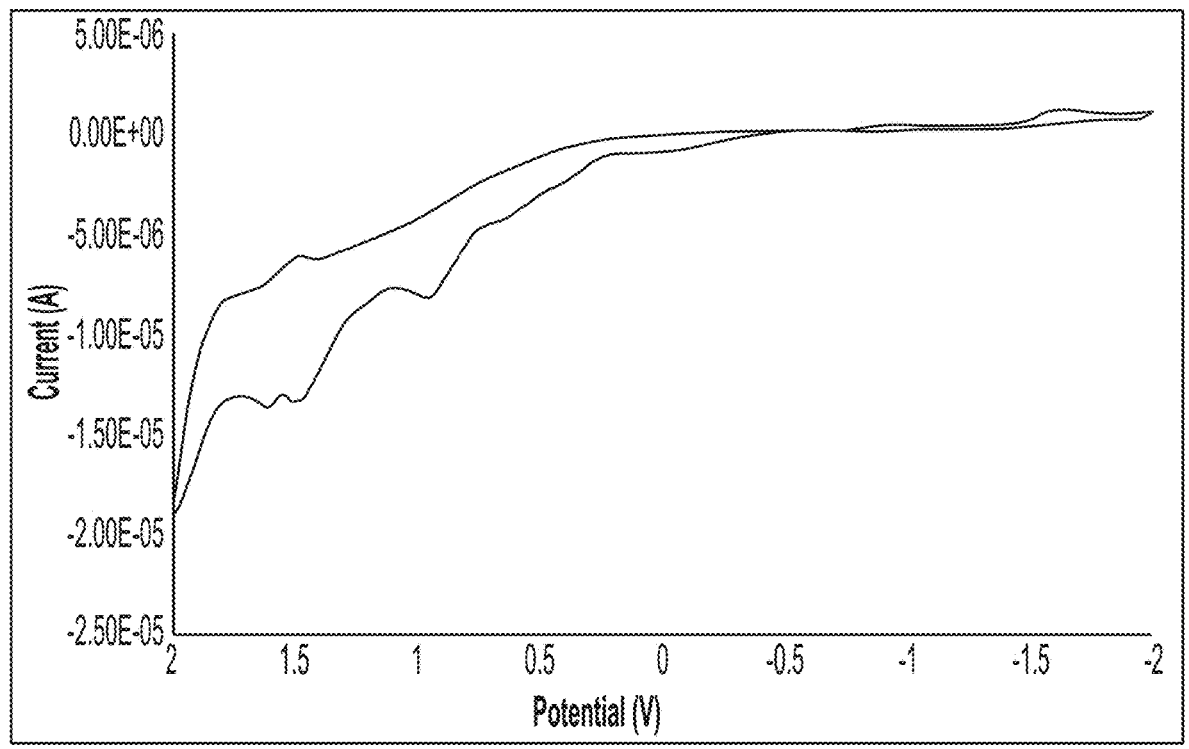
FIG. 13 is the cyclic voltammetry spectrum for IMes versus Ag/AgCl.
Figure 14:
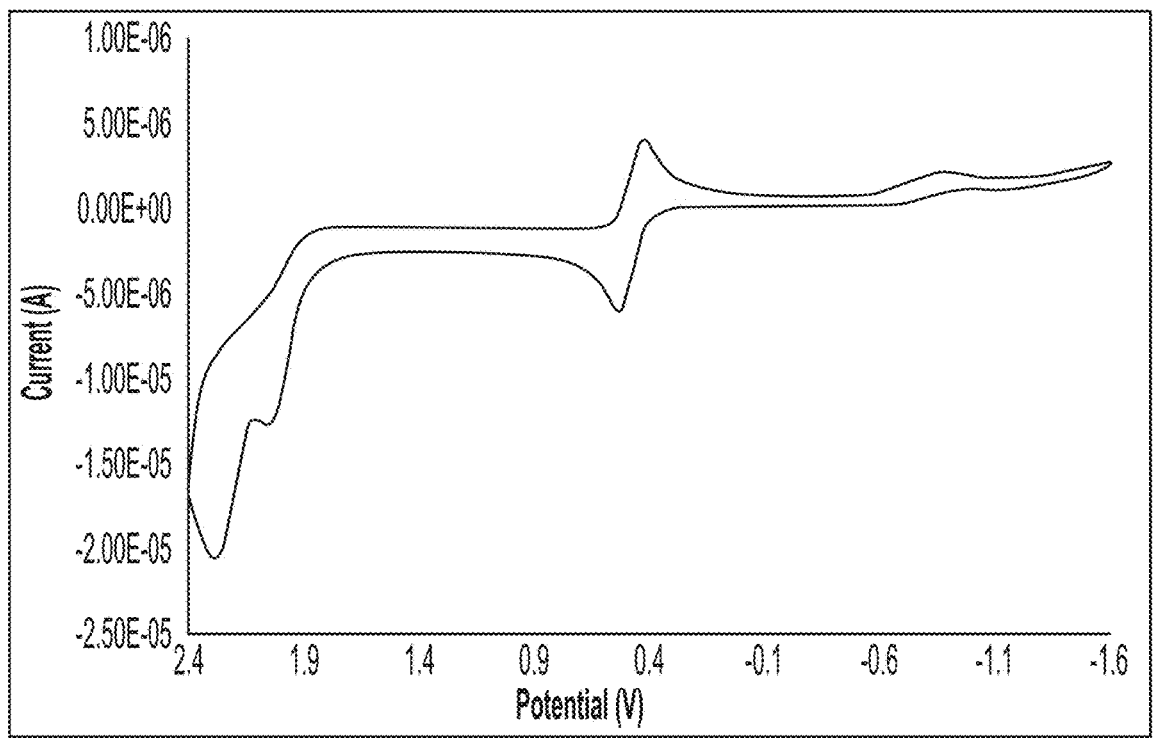
FIG. 14 is the cyclic voltammetry spectrum for $RuCl_2$(CHPh)(SIMes)$_2$ versus Ag/AgCl.
Figure 15:
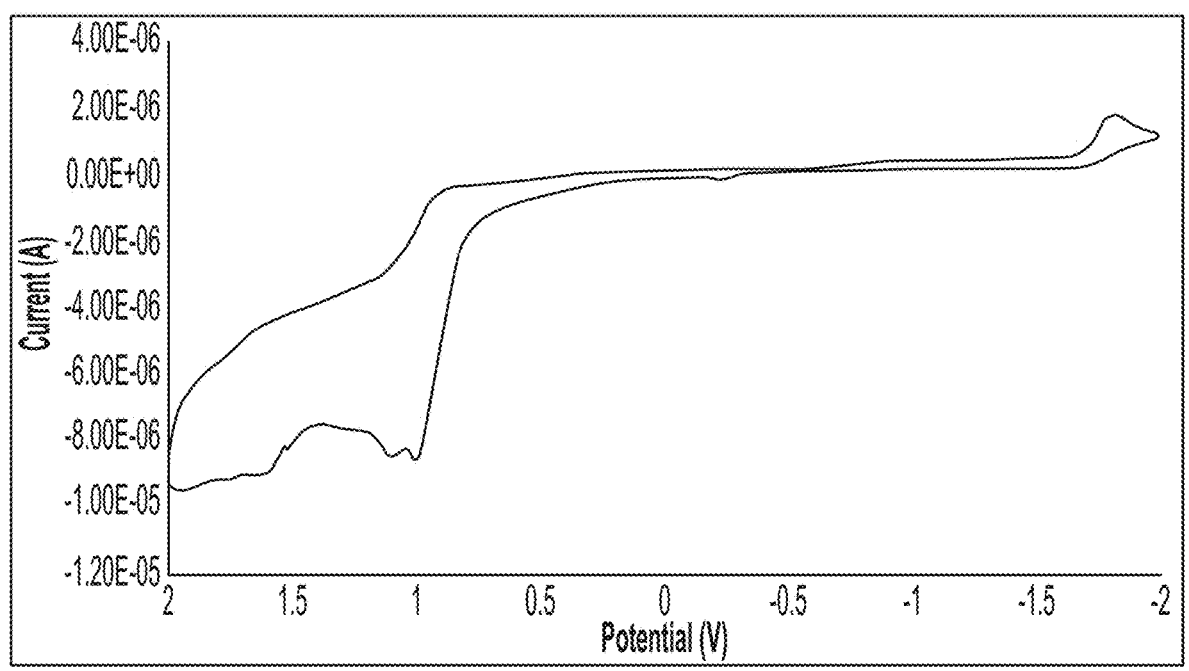
FIG. 15 is the cyclic voltammetry spectrum for SIMes versus Ag/AgCl.
Figure 16:
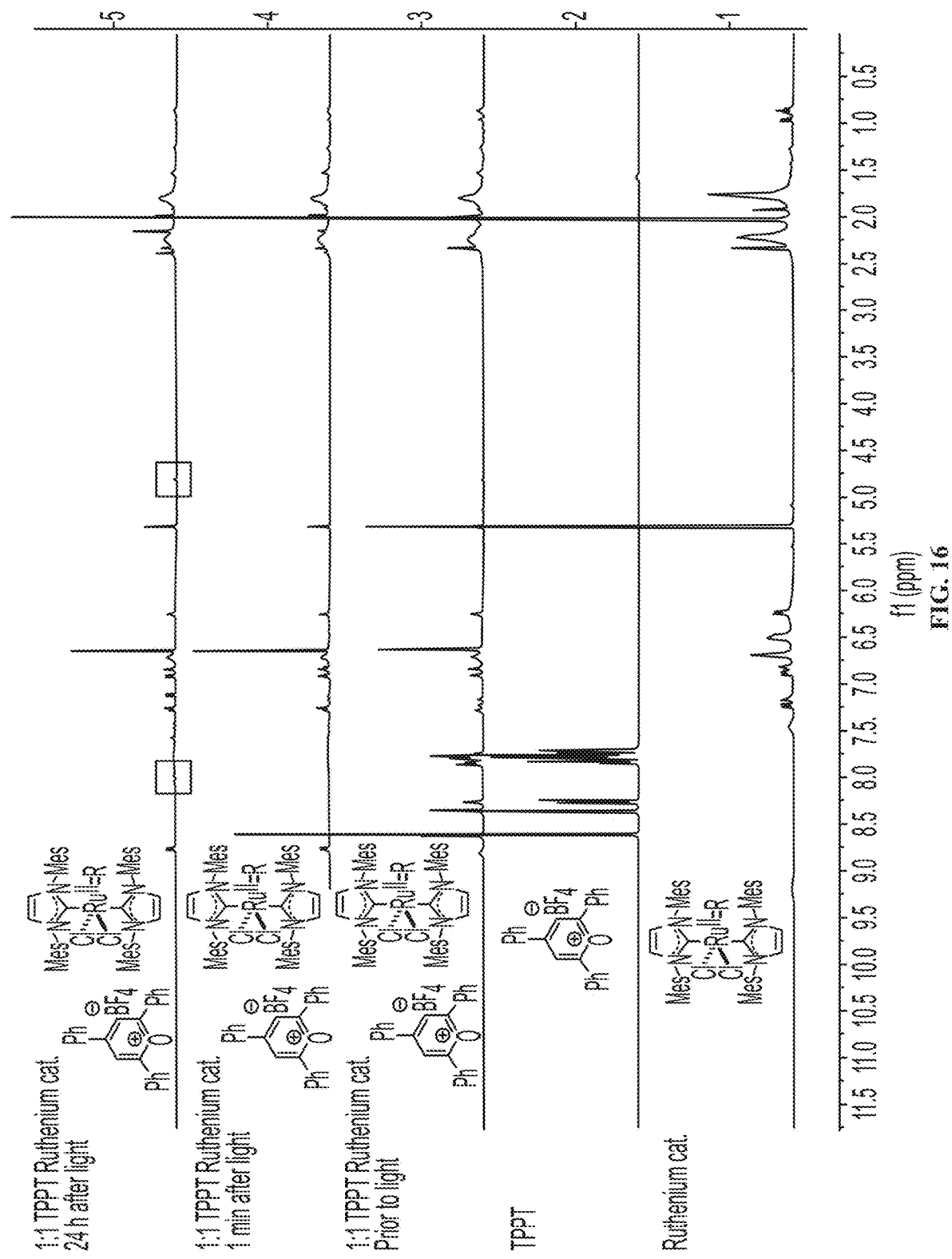
FIG. 16 are $^1$H-NMR spectra comparing the Ruthenium and TPPT catalysts prior and after blue light irradiation.
Figure 17:
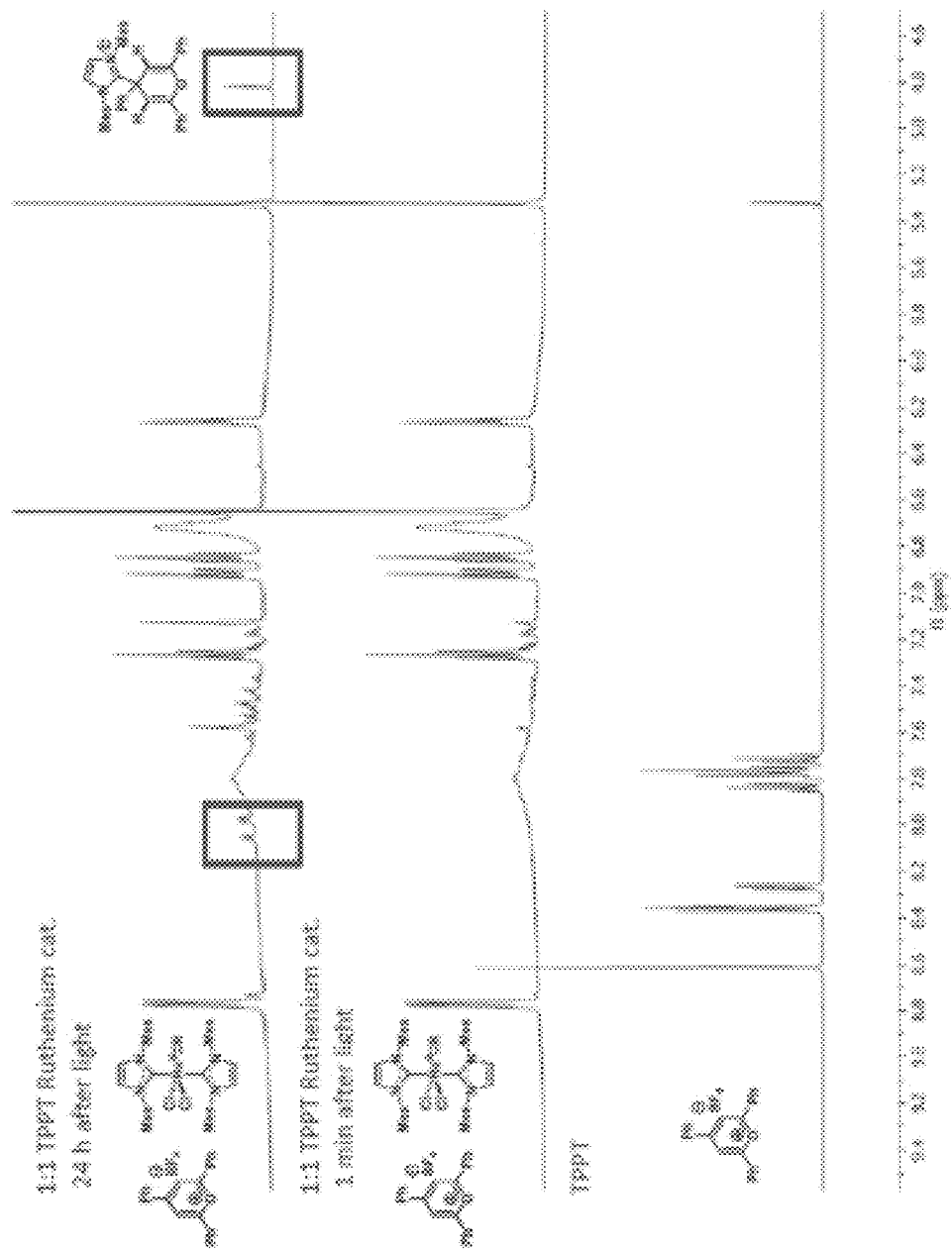
FIG. 17 are sections from FIG. 16 showing diagnostic peaks suggesting complexation of TPPT to potentially form intermediate VII.
Figure 18:
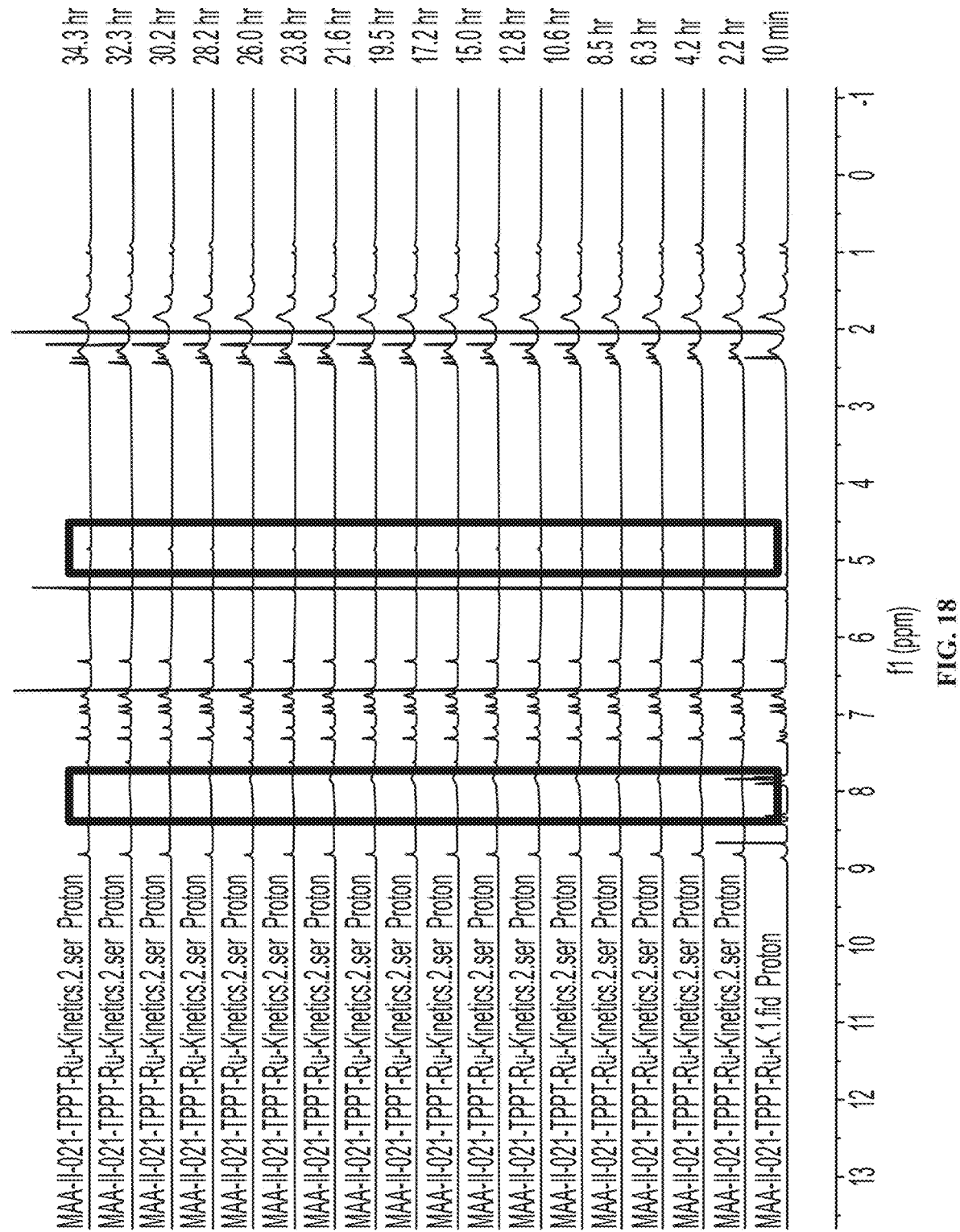
FIG. 18 are $^1$H-NMR spectra showing the kinetic NMR spectroscopy of a 1:1 solution of TPPT and RuCl$_2$(CHPh)(IMes)$_2$ in d-DCM.
Figure 19:
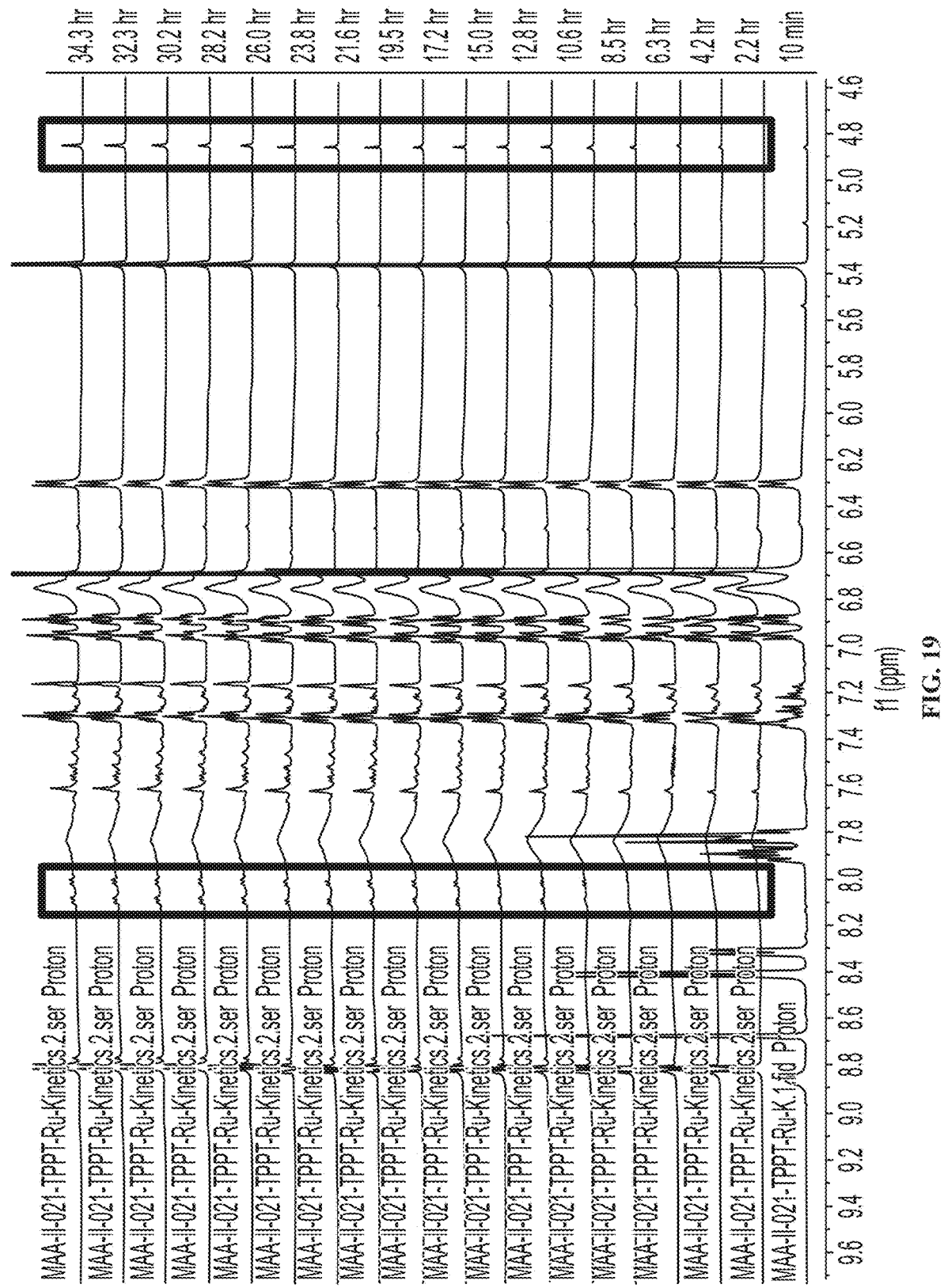
FIG. 19 are sections from FIG. 18 showing the diagnostic peaks.
Figure 20:
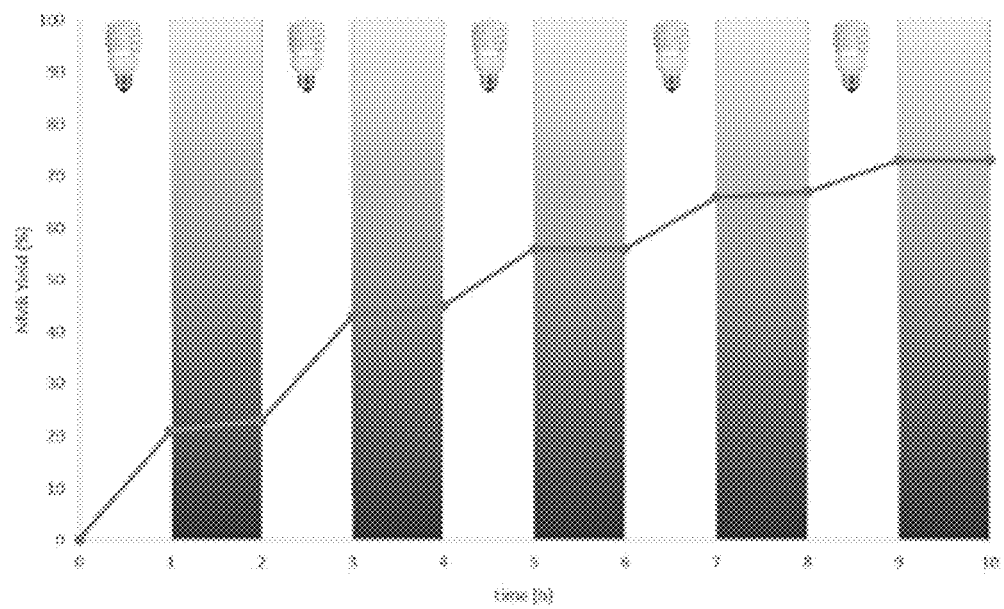
FIG. 20 is a bar graph showing the NMR yield over time of the ring closing metathesis of diethyl diallylmalonate using RuCl$_2$(CHPh)(IMes)$_2$ and 2,4,6-triphenylpyrylium tetrafluoroborate alternating cycles of irradiation and darkness.
Figure 21:
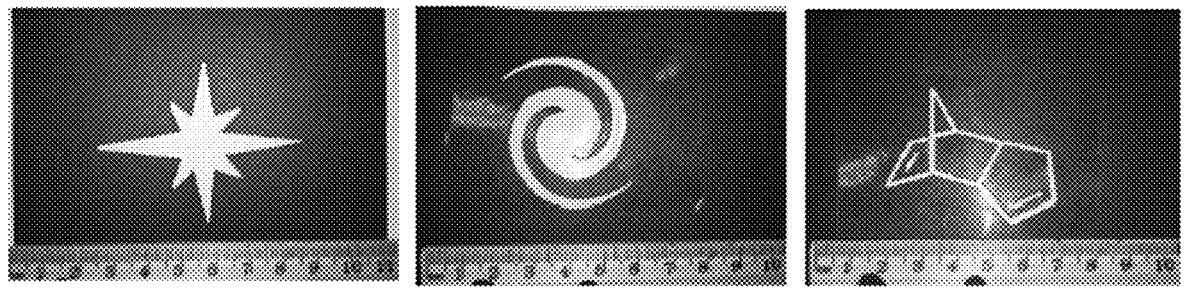
FIG. 21 are masks used to prepare the patterns of FIG. 6.
Figure 22:
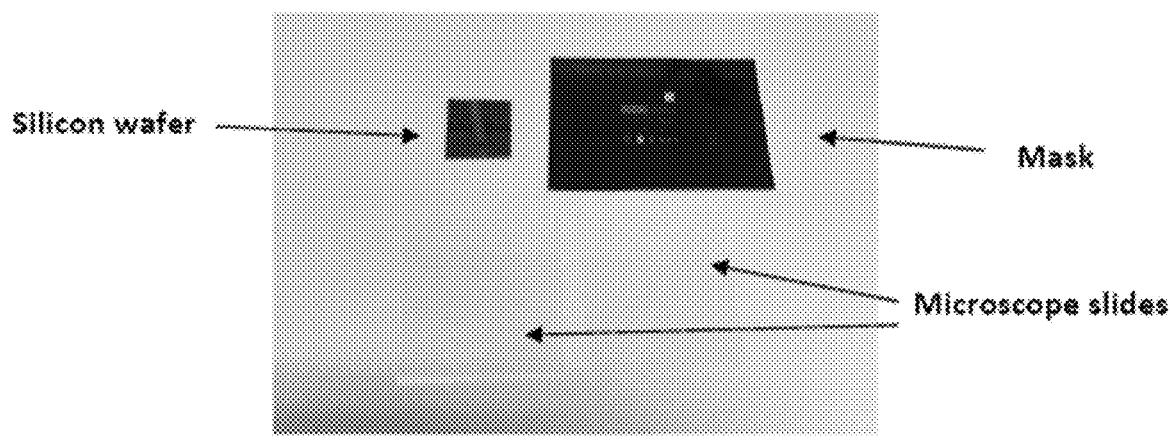
FIGS. 22 and 23 are photographs showing the experimental setup for photolithography on silicon wafers.
Figure 23:
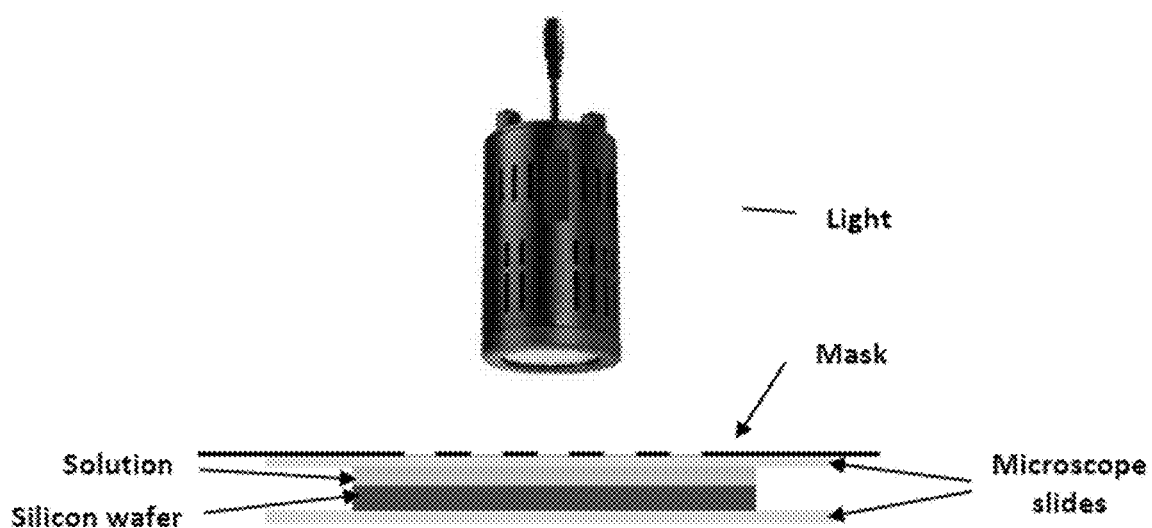
Figure 24A:
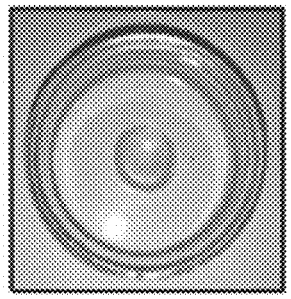
FIGS. 24A-24D are photographs of patterned poly(12, 9, 10 and 11).
Figure 24B:
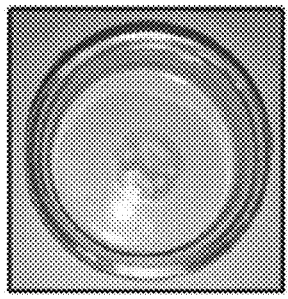
Figure 24C:
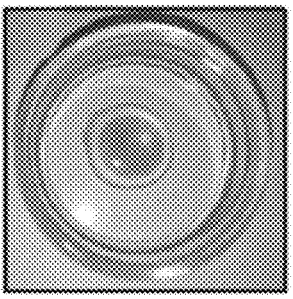
Figure 24D:
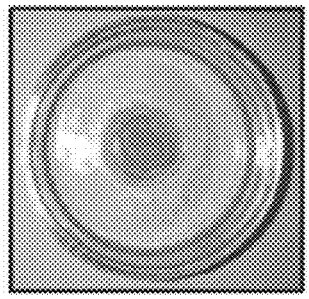
Figure 25A:
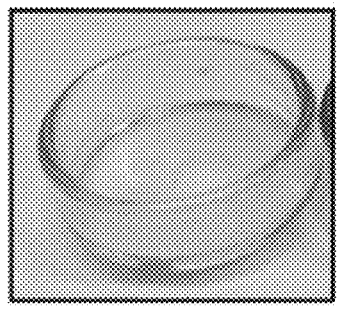
FIGS. 25A-25C are photographs of poly(dicyclopentadiene 12) illustrating Thickness as a function of irradiation time.
Figure 25B:
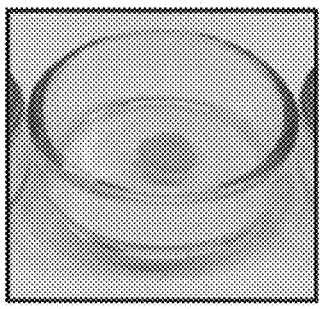
Figure 25C:
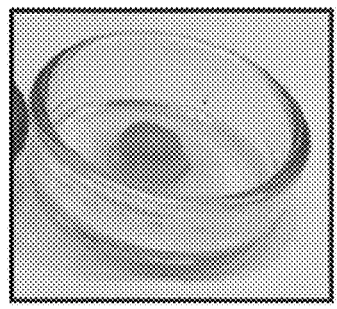

On/Off Experiments: On/off experiments were performed for the ring closing metathesis of diethyl diallylmalonate using 2 mol % of RuCl$_2$(CHPh)(IMes)$_2$ and 4 mol % of 2,4,6-triphenylpyrylium tetrafluoroborate (TPPT) in CH$_2$Cl$_2$ (0.2M) at room temperature over a period of time alternating cycles of irradiation and darkness. The reaction was conducted in the presence of mesitylene, used as internal standard. Aliquots were taken every hour and yields were determined by $^1$H NMR. On/off experiments were also performed with for the RCM of dibenzyl diallylmalonate to provide 75% yield in 3.5 h. The on and off study is shown in FIG. 9D.

Extended Substrate Scope

These two tables display the synthesis of small molecules.

TABLE 4

| Entry | Substrate | Product | Yield[b] (%) |
|---|---|---|---|
| 1 | EtO$_2$C, CO$_2$Et, diallyl | EtO$_2$C, CO$_2$Et cyclopentene | 86 |
| 2 | EtO$_2$C, CO$_2$Et with methallyl/allyl | EtO$_2$C, CO$_2$Et methyl cyclopentene | 84 |
| 3 | EtO$_2$C, CO$_2$Et dimethallyl | EtO$_2$C, CO$_2$Et dimethyl cyclopentene | Trace |
| 4 | Ts-N(allyl)$_2$ | N-Ts pyrroline | 90 |
| 5[c] | Ts-N(butenyl)$_2$ | N-Ts azepine | 89 |
| 6 | Ph-CH(OAllyl)-CH$_2$-CH=CH$_2$ | Ph-dihydropyran | 72 |
| 7[c,d] | Ph-CH=CH-CH$_3$ + CH$_2$=CH-CO$_2$Me | Ph-CH=CH-CH$_2$-CO$_2$Me | 60 |
| 8[c,d] | BzO-CH$_2$CH$_2$CH=CH$_2$ + AcO-CH$_2$CH=CHCH$_2$-OAc | BzO-(CH$_2$)$_2$CH=CHCH$_2$-OAc | 70 |
| 9[c,d] | (CH$_2$)$_4$-OAc allyl + 2-F-styrene | 2-F-C$_6$H$_4$-CH=CH-(CH$_2$)$_4$-OAc | 46 |
| 10[c,e] | cyclooctene + CH$_2$=CH-CO$_2$Me | MeO$_2$C-CH=CH-(CH$_2$)$_6$-CH=CH-CO$_2$Me | 51 |

[a]Conditions: substrate (0.2 mmol), RuCl$_2$(CHPh)(IMes)$_2$ (2 mol %), TPPT (3 mol %), CH$_2$Cl$_2$ (0.2M), rt, blue LEDs, 4 h.
[b]Isolated yields.
[c]4 mol % of TPPT.
[d]Top substrate (0.2 mmol), bottom substrate (0.4 mmol),
[e]Top substrate (0.2 mmol), bottom substrate (0.6 mmol).

TABLE 5
| Entry | Substrate | Product | Yield[b] (%) |
|---|---|---|---|
| 1 | 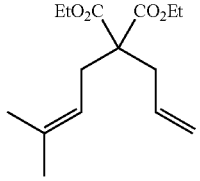 [SMILES: C=CCC(CC=C(C)C)(C(=O)OCC)C(=O)OCC] | 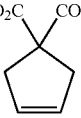 | 80 |
| 2 | 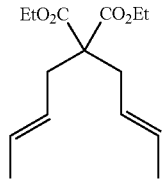 | 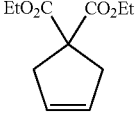 | 85 |
| 3 | 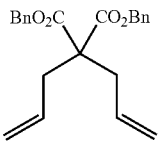 | 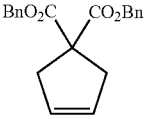 | 79 |
| 4 | 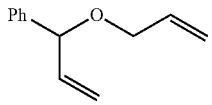 | 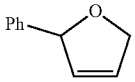 | 71 |
| 5[c] | 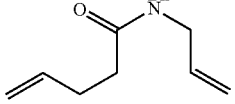 | 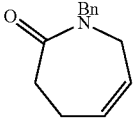 [SMILES: O=C1CCC=CCN1Cc1ccccc1] | 0 |
| 6 | 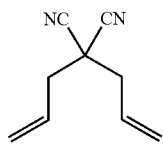 | 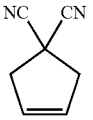 | 0 |
| 7[c] | 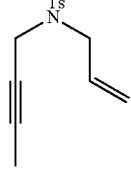 | 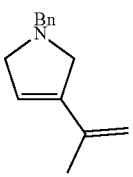 | 40 |
| 8[c,d] |  |  | 50 |
| 9[c,d] | 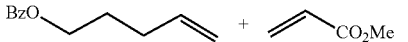 |  | 52 |
| 10[c,d] | 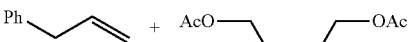 | 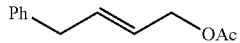 | 60 |
| 10[c,d] | 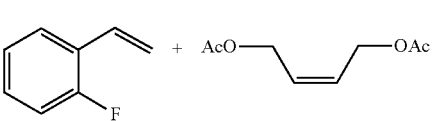 | 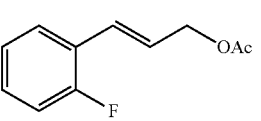 [SMILES: CC(=O)OC/C=C/c1ccccc1F] | 51 |
| 11[c,e] | 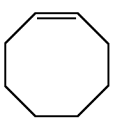 | 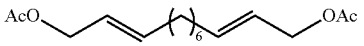 | 53 |

TABLE 5-continued
| Entry | Substrate | Product | Yield[b] (%) |
|---|---|---|---|
| 12[c,e] | 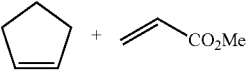 | 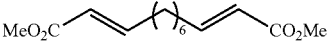 | 58 |
| 13 | 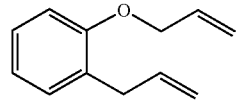 | 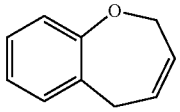 [SMILES: C1=CCc2ccccc2OC1] | <5 |
| 14 | 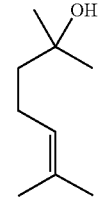 | 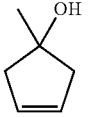 | 0 |
| 15 | 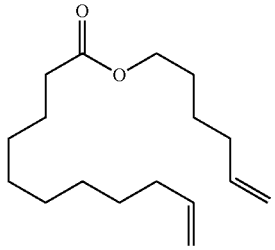 [SMILES: C=CCCCCCCCCC(=O)OCCCCC=C] | 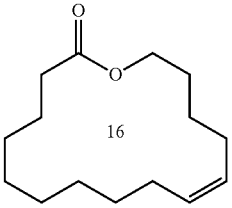 [SMILES: O=C1CCCCCCCC/C=C\CCCCO1] | <1 |
| 16 | 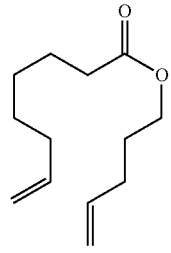 | 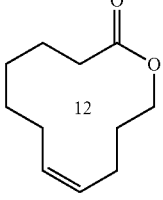 | <1 |
| 17 | 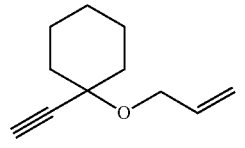 | 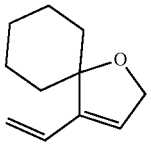 | 20 |
| 18 | 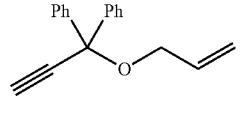 [SMILES: C#CC(OCC=C)(c1ccccc1)c1ccccc1] | 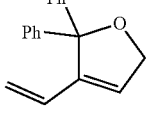 | 10 |
| 19 | 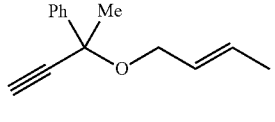 | 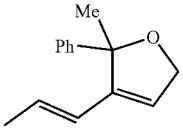 [SMILES: C/C=C/C1=CCOC1(c1ccccc1)c1ccccc1] | 22 |
| 20 | 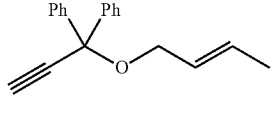 | 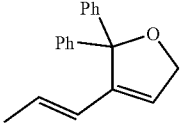 | 5 |

TABLE 5-continued

| Entry | Substrate | Product | Yield[b] (%) |
|---|---|---|---|
| 21 | EtO2C, CO2Et, allyl, alkyne (terminal) | EtO2C, CO2Et cyclopentene with vinyl | 0 |
| 22 | EtO2C, CO2Et, (E)-but-2-enyl, terminal alkyne | EtO2C, CO2Et cyclopentene with (E)-propenyl | 5 |
| 23 | EtO2C, CO2Et, (E)-but-2-enyl, propynyl | EtO2C, CO2Et cyclopentene with 2-butenyl | 5 |
| 24 | EtO2C, CO2Et, allyl, propynyl | EtO2C, CO2Et cyclopentene with isopropenyl | 21 |
| 25 | Ph-C(=O)-N(allyl)2 | Ph-C(=O)-N(2,5-dihydropyrrole) | 8 |
| 26 | Ts-N(2-methylallyl)2 | Ts-N 3,4-dimethyl-2,5-dihydropyrrole | <10 |
| 27 | Ts-N(allyl)(3-butenyl) | Ts-N tetrahydropyridine | 74 |
| 28 | Ts-N(3-butenyl)(3-methyl-3-butenyl) | Ts-N methyl-tetrahydroazepine | 0 |

TABLE 5-continued

| Entry | Substrate | Product | Yield[b] (%) |
|---|---|---|---|
| 29 | N-Ts, propargyl, prenyl | 3-(2-methylpropenyl)-1-Ts-2,5-dihydropyrrole | 18 |
| 30 | N-Ts, propargyl, allyl | 3-vinyl-1-Ts-2,5-dihydropyrrole | 0 |
| 31 | N-Ts, propargyl, crotyl | 3-propenyl-1-Ts-2,5-dihydropyrrole | 0 |
| 32 | OBz-substituted propargyl alcohol (H/Me) + 1-hexene (2 equiv.) | OZb product (H/Me) | 0 |
| 33 | BzO(CH$_2$)$_2$CH=CH$_2$ + CH$_2$=CHCO$_2$Me (2 equiv.) | BzO(CH$_2$)$_2$CH=CHCO$_2$Me | 30 |
| 34 | 4-Cl-C$_6$H$_4$-CH=CH$_2$ + CH$_2$=CHCO$_2$Me (2 equiv.) | 4-Cl-C$_6$H$_4$-CH=CH-CO$_2$Me | 30 |
| 35 | TBSO(CH$_2$)$_4$CH=CH$_2$ + CH$_2$=CHCO$_2$Me (2 equiv.) | TBSO(CH$_2$)$_4$CH=CHCO$_2$Me | 13 |
| 36 | 4-MeO-C$_6$H$_4$-O(CH$_2$)$_2$CH=CH$_2$ + CH$_2$=CHCO$_2$Me (2 equiv.) | 4-MeO-C$_6$H$_4$-O(CH$_2$)$_2$CH=CHCO$_2$Me | 6 |
| 37 | PhCH$_2$CH=CH$_2$ + AcO-CH$_2$CH=CHCH$_2$-OAc (2 equiv.) | PhCH$_2$CH=CHCH$_2$OAc | 60 |
| 38 | BzOCH$_2$C(Me)=CH$_2$ + CH$_2$=CH(CH$_2$)$_4$OAc (2 equiv.) | BzOCH$_2$C(Me)=CH(CH$_2$)$_4$OAc | 10-20 |
| 39 | 2-Br-C$_6$H$_4$-CH=CH$_2$ + CH$_2$=CH(CH$_2$)$_4$OAc (2 equiv.) | 2-Br-C$_6$H$_4$-CH=CH(CH$_2$)$_4$OAc | 25 |
| 40 | CH$_2$=CH(CH$_2$)$_4$OAc + 2-F-C$_6$H$_4$-CH=CH$_2$ (2 equiv.) | 2-F-C$_6$H$_4$-CH=CH(CH$_2$)$_4$OAc | 4 |

TABLE 5-continued
| Entry | Substrate | Product | Yield[b] (%) |
|---|---|---|---|
| 41 | 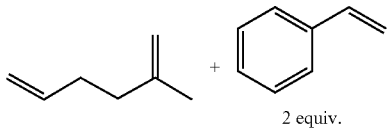 + 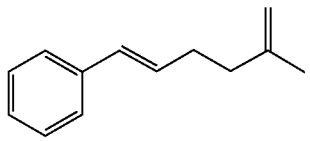<br>2 equiv. | 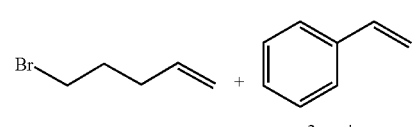 | 0 |
| 42 | 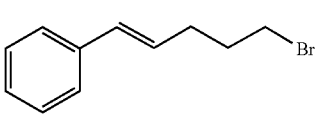 [SMILES: BrCCC/C=C/c1ccccc1] + 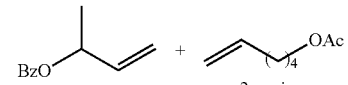<br>2 equiv. | 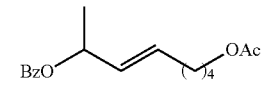 | 0 |
| 43 | 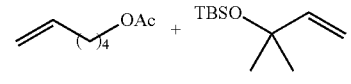 + 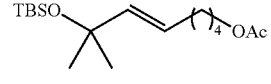<br>2 equiv. | 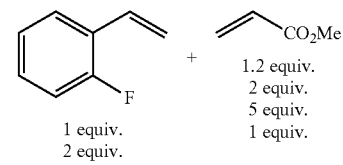 | 25 |
| 44 | 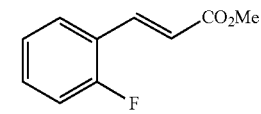 [SMILES: COC(=O)/C=C/c1ccccc1F] + 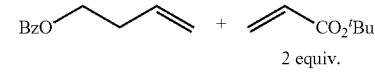<br>2 equiv. | 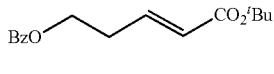 | 0 |
| 45 | 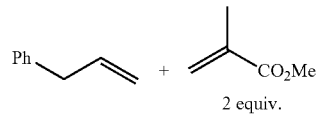<br>1 equiv.<br>2 equiv. + 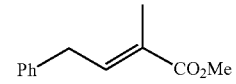<br>1.2 equiv.<br>2 equiv.<br>5 equiv.<br>1 equiv. | 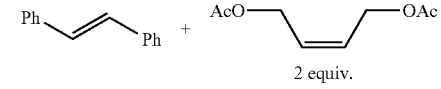 | 18<br>20<br>24<br>12 |
| 46 | 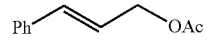 + 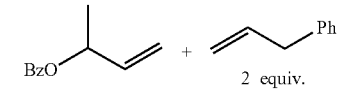<br>2 equiv. | 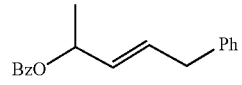 | <30 |
| 47 | 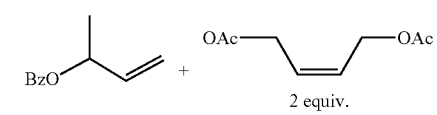 + 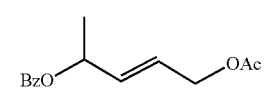<br>2 equiv. | 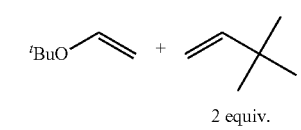 | 5-10 |
| 48 | 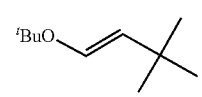 + 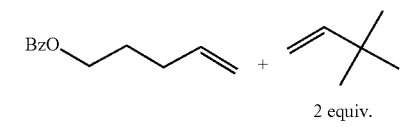<br>2 equiv. | 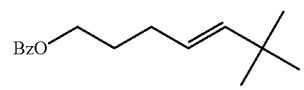 | 0 |
| 49 | + 2 equiv. | | 0 |
| 50 | + 2 equiv. | | 0 |
| 51 | + 2 equiv. | | 10 |
| 52 | + 2 equiv. | | 20 |

TABLE 5-continued

| Entry | Substrate | Product | Yield[b] (%) |
|---|---|---|---|
| 53 | 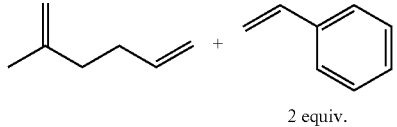 + 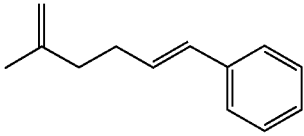 2 equiv. | 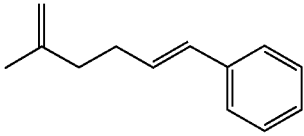 | 22 |
| 54 | 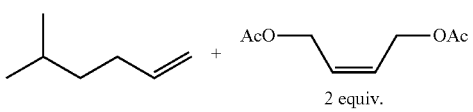 + 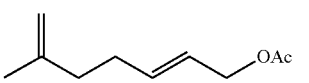 2 equiv. | 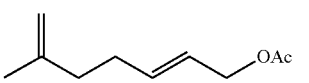 | 36 |
| 55 | 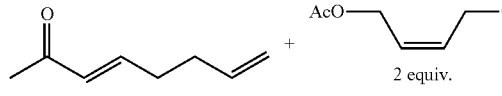 + 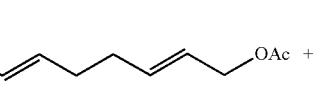 2 equiv. | 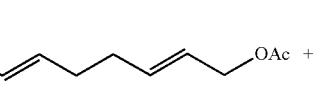 + 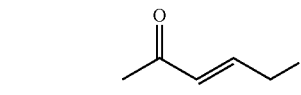 | <40 |
| 56 | 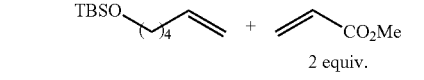 + 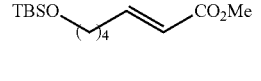 2 equiv. | 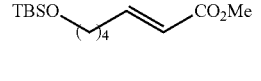 | 8 |
| 57 | 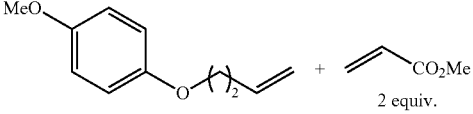 + 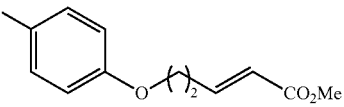 2 equiv. | 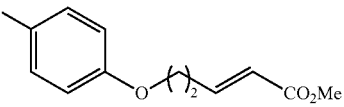 | 0 |
| 58 | 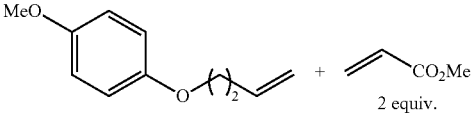 +  2 equiv. |  | 0 |
| 59 | 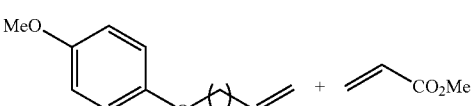 +  2 equiv. |  | 0 |
| 60 |  +  2 equiv. |  | 0 |
| 61 | 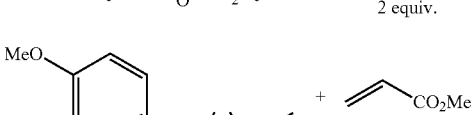 +  2 equiv. |  | 0 |

Scope of the Reaction: Ring-Opening—Cross-Metathesis

The tandem ring-opening—cross-metathesis has also been evaluated starting from several cyclic alkenes and proved to be quite successful in some cases (Scheme 1). The ROCM of cyclooctene with cis-1,4-diacetoxy-2-butene, methyl acrylate and tert-butyl acrylate afforded the desired products in fair yields (53%, 51% and 43% respectively). The use of hex-5-en-1-yl acetate afforded a mixture of inseparable mono- and bis-coupled products with an overall yield below 50%. On the other hand, the use of exo-di-substituted norbornenes only led to polymerization with full conversion of the starting materials and no desired products observed. The ROCM of norbornene itself with cis-1,4-diacetoxy-2-butene and methyl acrylate only led to poor yields of the desired products (20% and 28% respectively). Finally, the ROCM of cyclopentene with cis-1,4-diacetoxy-2-butene led to the formation of the desired product in less than 30% yield whereas the use of methyl acrylate afforded the corresponding product in a 58% yield.

Scheme 1

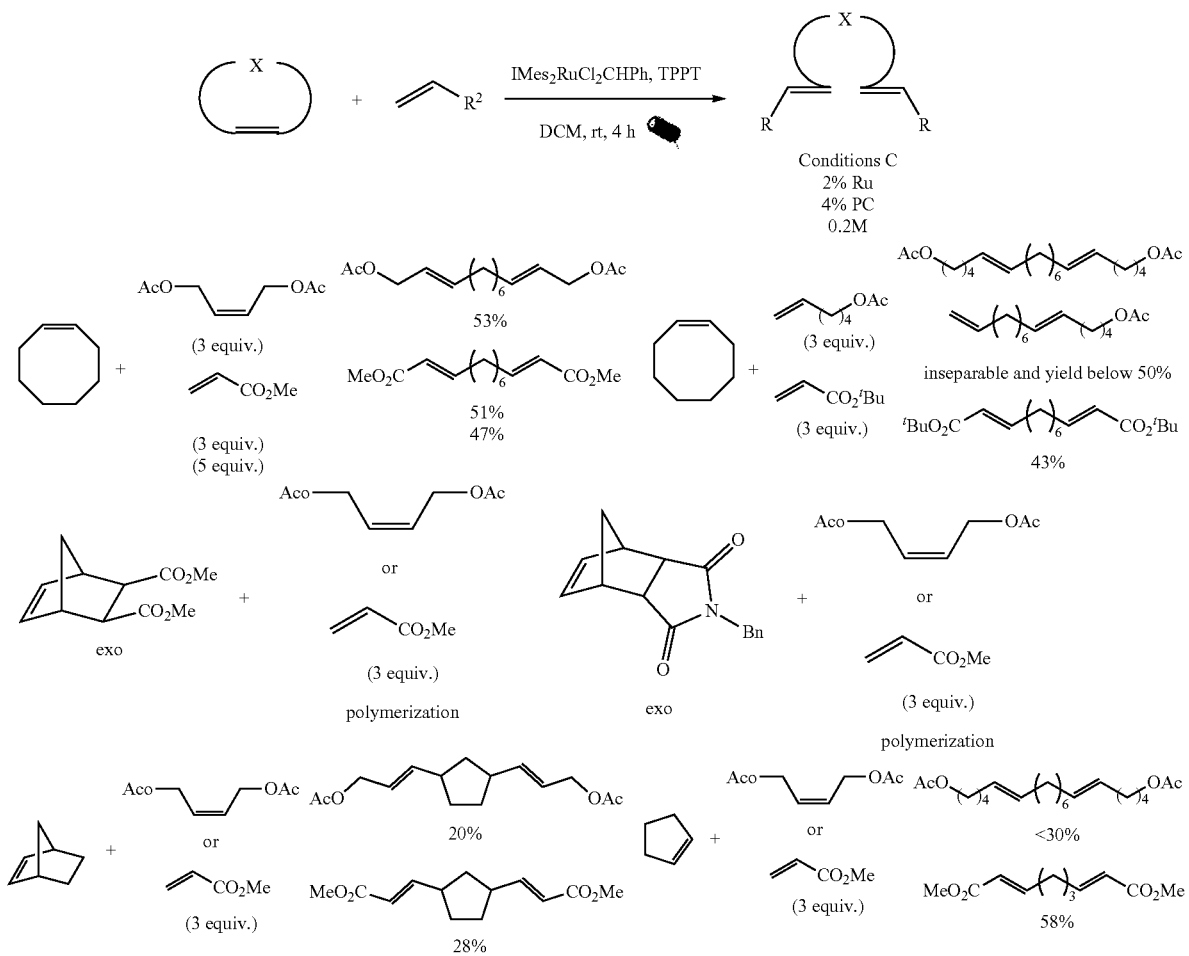

Experimental Setups

Experimental Setup 1: Visible-Light-Controlled Olefin Metathesis

The experimental setup includes a magnetic stirrer placed in a cardboard box, two blue Kessil LED lamps (440 nm) as light sources and a fan to maintain the reaction mixture at room temperature. The Kessil lamps are placed at a distance of 5-10 cm from the vial.

Experimental Setup 2: Polymer Patterning Using Macroscopic Photomasks

The polymer patterning experiments using macroscopic photomasks are conducted in a glovebox. The experimental setup includes: a BRAND® petri dish (glass) in which the polymerization is performed, a blue Kessil LED lamp (440 nm) as the light source, a black paper photomask with the appropriate pattern and a fan to maintain the reaction mixture at room temperature. The Kessil lamp is placed at a distance of 5-10 cm from the petri dish.

Experimental Setup 3: Polymer Patterning Using Blue Laser

The polymer patterning experiments using blue lasers are conducted in a glovebox. The experimental setup includes: a BRAND® petri dish (glass) in which the polymerization is performed, a blue laser pointer (450 nm, 200 mW) as the light source and a magnifying glass to focus the laser beam. The support stand is moved either manually or with an orbital shaker to induce patterning. The blue laser is placed at a distance of 5-10 cm from the petri dish.

Experimental Setup 4: Photolithography on Silicon Wafers

The photolithographic experiments on silicon wafers are conducted in a glovebox. The experimental setup includes: a norbornene-pre-functionalized silicon wafer, two microscope slides (22 mm×22 mm, thickness of 0.13-0.17 mm), a blue Kessil LED lamp (440 nm) as the light source, a high resolution photomask and a fan to maintain the system at room temperature. The Kessil lamp is placed at a distance of 5-10 cm from the silicon wafer.

Experimental Procedures and Characterization Data:
Metathesis for the Synthesis of Small Molecules
General Procedure A: Ring Closing and Enyne Metathesis In a glovebox, an oven-dried 1-dram vial was charged with the substrate (0.2 mmol), 2,4,6-triphenylpyrylium tetrafluoroborate TPPT (2.4 mg, 6 µmol unless otherwise noted), CH$_2$Cl$_2$ (1 mL) and RuCl$_2$(CHPh)(IMes)$_2$ (3.5 mg, 4 µmol). The vial was tightly sealed and removed from the glovebox before stirring at room temperature under blue LEDs irradiation for 4 h (experimental setup 1). The reaction mixture was then concentrated under vacuum and purified by flash column chromatography over silica gel.

General Procedure B: Cross-Metathesis

In a glovebox, an oven-dried 1-dram vial was charged with the limiting olefin (0.2 mmol), 2,4,6-triphenylpyrylium tetrafluoroborate TPPT (3.2 mg, 8 μmol), $CH_2Cl_2$ (1 mL), the excess olefin (0.4 mmol) and $RuCl_2(CHPh)(IMes)_2$ (3.5 mg, 4 μmol). The vial was tightly sealed and removed from the glovebox before stirring at room temperature under blue LEDs irradiation for 4 h (experimental setup 1). The reaction mixture was then concentrated under vacuum and purified by flash column chromatography over silica gel.

General Procedure C: Ring Opening—Cross-Metathesis

In a glovebox, an oven-dried 1-dram vial was charged with the cyclic olefin (0.2 mmol), 2,4,6-triphenylpyrylium tetrafluoroborate TPPT (3.2 mg, 8 μmol), $CH_2Cl_2$ (1 mL), the terminal olefin (0.6 mmol) and $RuCl_2(CHPh)(IMes)_2$ (3.5 mg, 4 μmol). The vial was tightly sealed and removed from the glovebox before stirring at room temperature under blue LEDs irradiation for 4 h (experimental setup 1). The reaction mixture was then concentrated under vacuum and purified by flash column chromatography over silica gel.

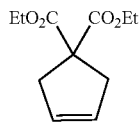

Diethyl cyclopent-3-ene-1,1-dicarboxylate. Prepared according to General Procedure A. Yield: 86% (36.7 mg, 173 μmol) from diethyl diallylmalonate, 80% (34.1 mg, 161 μmol) from diethyl 2-allyl-2-(3-methylbut-2-en-1-yl)malonate and 85% (36.2 mg, 170 μmol) from diethyl 2,2-bis-(but-2-enyl)malonate. Solvent system for flash column chromatography: hexanes/EtOAc: 95/5; Pale yellow oil. This compound has been previously reported. See, Yao, J. Am. Chem. Soc., 2004, 126, 74-75.

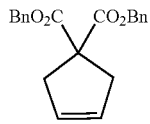

Dibenzyl cyclopent-3-ene-1,1-dicarboxylate. Prepared according to General Procedure A. Yield: 79% (53.4 mg, 159 μmol). Solvent system for flash column chromatography: hexanes/EtOAc: 95/5; Colorless oil. $^1$H NMR (500 MHz, $CDCl_3$): δ 7.36-7.24 (m, 10H), 5.62 (s, 2H), 5.14 (s, 4H), 3.07 (s, 4H); $^{13}$C NMR (125 MHz, $CDCl_3$): δ 171.9, 135.6, 128.6, 128.3, 128.1, 127.9, 67.3, 59.0, 41.0; IR (ATR): $v_{max}$ 3063, 2926, 1756, 1724, 1459, 1246, 1163, 1062, 975, 731, 694, 453 cm-1; ESIHRMS m/z calcd for $C_{21}H_{21}O_4$ [M+H]+ 337.1434, found 337.1440.

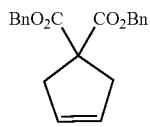

Diethyl 3-methylcyclopent-3-ene-1,1-dicarboxylate. Prepared according to General Procedure A. Yield: 84% (38.2 mg, 169 μmol). Solvent system for flash column chromatography: hexanes/EtOAc: 95/5; Colorless oil. This compound has been previously reported. See, Xi, Org. Lett., 2007, 9, 3259-3261.

1-Tosyl-2,5-dihydro-1H-pyrrole. Prepared according to General Procedure A.

Yield: 90% (40.2 mg, 180 μmol). Solvent system for flash column chromatography: hexanes/EtOAc: 90/10; White solid. This compound has been previously reported. See, Hongfa, Org. Lett., 2007, 9, 3259-3261.

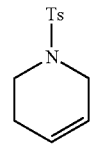

1-Tosyl-1,2,3,6-tetrahydropyridine. Prepared according to General Procedure A using 2 μmol of $RuCl_2(CHPh)(IMes)_2$ and 4 μmol of TPPT. Yield: 74% (35.3 mg, 149 μmol). Solvent system for flash column chromatography: hexanes/EtOAc: 90/10; White solid. This compound has been previously reported. See, Lipschutz, J. Org. Lett., 2011, 76, 4379-4391.

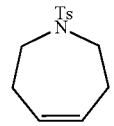

1-Tosyl-2,3,6,7-tetrahydro-1H-azepine. Prepared according to General Procedure A using 2 μmol of $RuCl_2(CHPh)(IMes)_2$ and 4 μmol of TPPT. Yield: 89% (45.0 mg, 179 μmol). Solvent system for flash column chromatography: hexanes/EtOAc: 95/5; White solid. This compound has been previously reported. See, Wu, Eur. J. Org. Chem., 2012, 6777-6784.

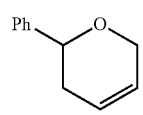

2-Phenyl-3,6-dihydro-2H-pyran. Prepared according to General Procedure A. Yield: 72% (23.0 mg, 143 μmol). Solvent system for flash column chromatography: hexanes/EtOAc: 97/3; Colorless oil. This compound has been previously reported. See, Broggi, Chem. Eur. J., 2010, 16, 9215, 9225.

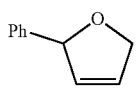 [SMILES: C1=CC(c2ccccc2)OC1]

2-Phenyl-2,5-dihydrofuran. Prepared according to General Procedure A. Yield: 71% (20.8 mg, 142 μmol). Solvent system for flash column chromatography: hexanes/EtOAc: 97/3; Colorless oil. This compound has been previously reported. See, Munoz, Adv. Synth. Catal., 2010, 352, 2189-2194.

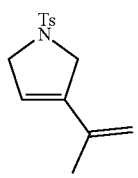 [SMILES: C=C(C)C1=CCN(S(=O)(=O)c2ccc(C)cc2)C1]

3-(Prop-1-en-2-yl)-1-tosyl-2,5-dihydro-1H-pyrrole. Prepared according to General Procedure A using 2 μmol of RuCl$_2$(CHPh)(IMes)$_2$ and 4 μmol of TPPT. Yield: 40% (21.1 mg, 80 μmol). Solvent system for flash column chromatography: hexanes/EtOAc: 97/3; White solid. This compound has been previously reported. See, Fürstner, Chem. Eur. J., 2001, 7, 3236-3253.

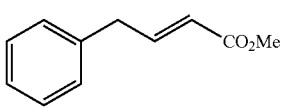 [SMILES: COC(=O)/C=C/Cc1ccccc1]

Methyl (E)-4-phenylbut-2-enoate. Prepared according to General Procedure B using allyl benzene (0.2 mmol) and methyl acrylate (0.4 mmol). Yield: 60% (21.3 mg, 121 μmol). Solvent system for flash column chromatography: hexanes/EtOAc: 95/5; Pale yellow oil. This compound has been previously reported. See, Wang, J. Am. Chem. Soc., 2007, 129, 276-277.

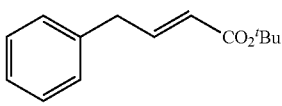 [SMILES: CC(C)(C)OC(=O)/C=C/Cc1ccccc1]

tert-Butyl (E)-4-phenylbut-2-enoate. Prepared according to General Procedure B using allyl benzene (0.2 mmol) and tert-butyl acrylate (0.4 mmol). Yield: 50% (22.0 mg, 101 μmol). Solvent system for flash column chromatography: hexanes/EtOAc: 95/5; Pale yellow oil. This compound has been previously reported. See, Bunnage, Tetrahedron, 1994, 50, 3975-3986.

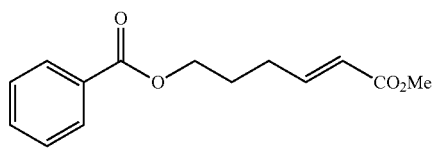 [SMILES: COC(=O)/C=C/CCCOC(=O)c1ccccc1]

(E)-6-(tert-Butoxy)-6-oxohex-4-en-1-yl benzoate. Prepared according to General Procedure B using pent-4-en-1-yl benzoate (0.2 mmol) and methyl acrylate (0.4 mmol). Yield: 52% (25.8 mg, 104 μmol). Solvent system for flash column chromatography: hexanes/EtOAc: 90/10; Yellow oil. This compound has been previously reported. See, Busque, Tetrahedron, 1995, 51, 1503-1508.

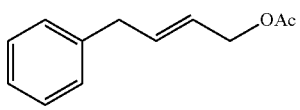 [SMILES: CC(=O)OC/C=C/Cc1ccccc1]

(E)-4-Phenylbut-2-en-1-yl acetate. Prepared according to General Procedure B using allyl benzene (0.2 mmol) and cis-1,4-diacetoxy-2-butene (0.4 mmol). Yield: 60% (E/Z: 9/1, 23.0 mg, 121 μmol). Solvent system for flash column chromatography: hexanes/EtOAc: 95/5; Colorless oil. This compound has been previously reported. See, Henderson, Org. Lett., 2010, 12, 824-827.

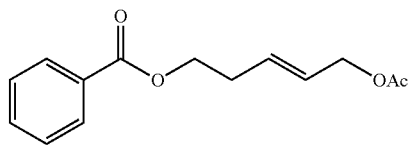 [SMILES: CC(=O)OC/C=C/CCOC(=O)c1ccccc1]

(E)-5-Acetoxypent-3-en-1-yl benzoate. Prepared according to General Procedure B using but-3-en-1-yl benzoate (0.2 mmol) and cis-1,4-diacetoxy-2-butene (0.4 mmol). Yield: 70% (E/Z: 9/1, 34.9 mg, 703 μmol). Solvent system for flash column chromatography: hexanes/EtOAc: 85/15; Colorless oil; $^1$H NMR (500 MHz, CDCl$_3$): E isomer δ 8.05 (app. d, J=8.3 Hz, 2H), 7.58 (app. tt, J=7.4 and 1.3 Hz, 1H), 7.46 (t, J=8.1 Hz, 2H), 5.85 (dtt, J=15.5, 6.6 and 1.2 Hz, 1H), 5.75 (dtt, J=15.5, 6.3 and 1.3 Hz, 1H), 4.55 (dd, J=6.3 and 0.9 Hz, 2H), 4.39 (t, J=6.5 Hz, 2H), 2.56 (qd, J=6.7 and 1.1 Hz, 2H), 2.06 (s, 3H); $^{13}$C NMR (75 MHz, CDCl$_3$): δ 170.9, 166.6, 133.2, 131.1, 130.4, 129.7, 128.4, 127.0, 64.9, 63.8, 31.9, 21.1; IR (ATR): ν$_{max}$ 2939, 1717, 1451, 1379, 1271, 1229, 1111, 1026, 968, 712 cm$^{-1}$; ESIHRMS m/z calcd for C$_{14}$H$_{16}$O$_4$Na [M+Na]+271.0941, found 271.0946.

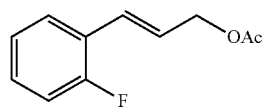 [SMILES: CC(=O)OC/C=C/c1ccccc1F]

(E)-3-(2-Fluorophenyl)allyl acetate. Prepared according to General Procedure B using 2-fluorostyrene (0.2 mmol) and cis-1,4-diacetoxy-2-butene (0.4 mmol). Yield: 51% (20.1 mg, 103 μmol). Solvent system for flash column chromatography: hexanes/EtOAc: 90/10; Colorless oil. This compound has been previously reported.21 (E)-6-(2-Fluorophenyl)hex-5-en-1-yl acetate. Prepared according to General Procedure B using 2-fluorostyrene (0.2 mmol) and hex-5-en-1-yl acetate (0.4 mmol). Yield: 46% (21.7 mg, 92 μmol). Solvent system for flash column chromatography: hexanes/EtOAc: 96/4; Colorless oil; $^1$H NMR (500 MHz, CDCl$_3$): δ 7.42 (td, J=7.7 and 1.7 Hz, 1H), 7.19-7.13 (m, 1H), 7.06 (td, J=7.4 and 1.0 Hz, 1H), 7.00 (ddd, J=10.9, 8.1 and 1.1 Hz, 1H), 6.55 (d, J=15.8 Hz, 1H), 6.28 (dt, J=15.9 and 7.1 Hz, 1H), 4.09 (t, J=6.6 Hz, 2H), 2.27 (qd, J=7.4 and 1.2 Hz, 2H), 2.05 (s, 3H), 1.73-1.66 (m, 2H), 1.59-1.52 (m, 2H); $^{13}$C NMR (125 MHz, CDCl$_3$): δ 171.3, 160.0 (d, J=246.6 Hz), 133.0 (d, J=4.3 Hz), 128.2 (d, J=8.3 Hz), 127.1 (d, J=3.8 Hz), 125.5 (d, J=12.3 Hz), 124.1 (d, J=3.5 Hz), 122.8 (d, J=3.6 Hz), 115.7 (d, J=22.1 Hz), 64.4, 33.0, 28.2, 25.7, 21.1; 19F NMR (470 MHz, CDCl$_3$): δ −119.4 (m); IR (ATR): ν$_{max}$ 2934, 1736, 1486, 1365, 1233, 1037, 969, 754, 606 cm$^{-1}$; ESIHRMS m/z calcd for C$_{14}$H$_{17}$FO$_2$Na [M+Na]+ 259.1105, found 259.1110.

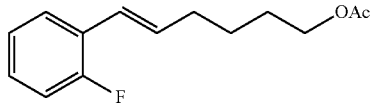 [SMILES: CC(=O)OCCCC/C=C/c1ccccc1F]

(E)-6-(2-Fluorophenyl)hex-5-en-1-yl acetate. Prepared according to General Procedure B using 2-fluorostyrene (0.2 mmol) and hex-5-en-1-yl acetate (0.4 mmol). Yield: 46% (21.7 mg, 92 µmol). Solvent system for flash column chromatography: hexanes/EtOAc: 96/4; Colorless oil; $^1$H NMR (500 MHz, CDCl$_3$): δ 7.42 (td, J=7.7 and 1.7 Hz, 1H), 7.19-7.13 (m, 1H), 7.06 (td, J=7.4 and 1.0 Hz, 1H), 7.00 (ddd, J=10.9, 8.1 and 1.1 Hz, 1H), 6.55 (d, J=15.8 Hz, 1H), 6.28 (dt, J=15.9 and 7.1 Hz, 1H), 4.09 (t, J=6.6 Hz, 2H), 2.27 (qd, J=7.4 and 1.2 Hz, 2H), 2.05 (s, 3H), 1.73-1.66 (m, 2H), 1.59-1.52 (m, 2H); $^{13}$C NMR (125 MHz, CDCl$_3$): δ 171.3, 160.0 (d, J=246.6 Hz), 133.0 (d, J=4.3 Hz), 128.2 (d, J=8.3 Hz), 127.1 (d, J=3.8 Hz), 125.5 (d, J=12.3 Hz), 124.1 (d, J=3.5 Hz), 122.8 (d, J=3.6 Hz), 115.7 (d, J=22.1 Hz), 64.4, 33.0, 28.2, 25.7, 21.1; 19F NMR (470 MHz, CDCl$_3$): δ −119.4 (m); IR (ATR): ν$_{max}$ 2934, 1736, 1486, 1365, 1233, 1037, 969, 754, 606 cm$^{-1}$; ESIHRMS m/z calcd for C$_{14}$H$_{17}$FO$_2$Na [M+Na]+259.1105, found 259.1110.

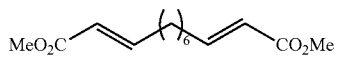

Dimethyl (2E,10E)-dodeca-2,10-dienedioate. Prepared according to General Procedure C using cis-cyclooctene (0.2 mmol) and methyl acrylate (0.6 mmol). Yield: 51% (26.0 mg, 102 µmol). Solvent system for flash column chromatography: hexanes/EtOAc: 90/10; Pale yellow oil; $^1$H NMR (500 MHz, CDCl$_3$): δ 6.95 (dt, J=15.5 and 6.9 Hz, 2H), 5.81 (dt, J=15.6 and 1.5 Hz, 2H), 3.72 (s, 6H), 2.19 (qd, J=7.2 and 1.5 Hz, 4H), 1.49-1.40 (m, 4H), 1.36-1.27 (m, 4H); $^{13}$C NMR (125 MHz, CDCl$_3$): δ 167.3, 149.7, 121.1, 51.5, 32.2, 29.0, 28.0; IR (ATR): ν$_{max}$ 2927, 2854, 1721, 1656, 1435, 1269, 1195, 1178, 1038, 980, 716 cm$^{-1}$; ESIHRMS m/z calcd for C$_{14}$H$_{23}$O$_4$ [M+H]+ 255.1591, found 255.1596.

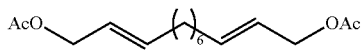

(2E,10E)-Dodeca-2,10-diene-1,12-diyl diacetate. Prepared according to General Procedure C using cis-cyclooctene (0.2 mmol) and cis-1,4-diacetoxy-2-butene (0.6 mmol). Yield: 53% (E,E/E,Z: 9/1, 30.0 mg, 106 µmol). Solvent system for flash column chromatography: hexanes/EtOAc: 95/5; Colorless oil; $^1$H NMR (500 MHz, CDCl$_3$): E/E isomer δ 5.76 (app. dt, J=15.3 and 6.8 Hz, 2H), 5.55 (dtt, J=15.3, 6.5 and 1.3 Hz, 2H), 4.50 (dd, J=6.5 and 0.7 Hz, 4H), 2.07-2.01 (m, 4H), 2.06 (obs. s, 6H), 1.42-1.33 (m, 4H), 1.32-1.25 (m, 4H); $^{13}$C NMR (125 MHz, CDCl$_3$): δ 171.0, 136.7, 123.9, 65.5, 32.3, 29.1, 28.9, 21.2; IR (ATR): ν$_{max}$ 2926, 2854, 1737, 1446, 1363, 1228, 1023, 965, 698, 607 cm$^{-1}$; ESIHRMS m/z calcd for C$_{16}$H$_{26}$O$_4$Na [M+Na]+ 305.1723, found 305.1729.

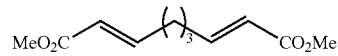

Dimethyl (2E,7E)-nona-2,7-dienedioate. Prepared according to General Procedure C using cyclopentene (0.2 mmol) and methyl acrylate (0.6 mmol). Yield: 58% (24.5 mg, 115 µmol). Solvent system for flash column chromatography: hexanes/EtOAc: 90/10; Pale yellow oil. This compound has been previously reported.[22]

Experimental Procedure and Characterization Data:
Ring Opening Metathesis Polymerization
General Procedure In a glovebox, an oven-dried 1-dram vial was charged with the monomer (0.2 mmol), 2,4,6-triphenylpyrylium tetrafluoroborate TPPT (0.79 mg, 2 µmol), CD2Cl$_2$ (1 mL) and RuCl$_2$(CHPh)(IMes)$_2$ (0.87 mg, 1 µmol). Mesitylene (27.8 µL, 0.2 mmol) was added and used as internal standard to monitor conversion. The vial was tightly sealed and removed from the glovebox before stirring at room temperature under blue LEDs irradiation for 1 h (experimental setup 1). The reaction mixture was then poured into methanol and the desired polymer was finally isolated by filtration, washed thoroughly with methanol and pentane and dried under vacuum.

Dicyclopentadiene was polymerized using 0.1 µmol of RuCl$_2$(CHPh)(IMes)$_2$ and 0.5 µmol of TPPT during 15 minutes.

Poly[bicyclo[2.2.1]hept-2-ene] 1. Conversion: >95%. $^1$H NMR (500 MHz, CDCl3): δ 5.34 (br. s, 1H), 5.21 (br. s, 1H), 2.79 (br. s, 1H), 2.43 (br. s, 1H), 1.96-1.68 (m, 3H), 1.35 (br. s, 2H), 1.12-0.93 (m, 1H).

Poly[exo,exo-dibenzyl bicyclo[2.2.1]hept-5-ene-2,3-dicarboxylate]2. Conversion: >95%. $^1$H NMR (500 MHz, CDCl$_3$): δ 7.30-7.15 (m, 10H), 5.39-5.10 (m, 2H), 5.00-4.70 (m, 4H), 3.56-3.28 (m, 1H), 3.07-2.68 (m, 3H), 2.30-1.80 (m, 1H), 1.28-0.99 (m, 1H).

Poly[exo,exo-7-oxabicyclo[2.2.1]hept-5-ene-2,3-diylbis (methylene) diacetate] 3. Conversion: 95%. $^1$H NMR (500 MHz, CDCl$_3$): δ 5.79-5.52 (m, 2H), 4.49 (br. s, 1H), 4.24-4.07 (m, 5H), 2.06-2.01 (m, 6H).

Poly[(bicyclo[2.2.1]hept-5-en-2-yloxy)(tert-butyl)dimethylsilane] 4. Conversion: >95%. $^1$H NMR (500 MHz, CDCl$_3$): δ 5.47-5.09 (m, 2H), 3.63-3.31 (m, 2H), 3.02-2.32 (m, 2H), 2.21-1.65 (m, 3H), 1.52-1.04 (m, 2H), 0.89 (br. s, 9H), 0.02 (br. s, 6H).

Estimation of the Krel Light/Dark for the Polymerization of Dicyclopentadiene 12

Following the general procedure described above, polymerization of dicyclopentadiene was performed under blue LED irradiation, stopped after 90 seconds and immediately quenched by addition of excess ethyl vinyl ether. Analysis of the crude reaction mixture by $^1$H NMR showed 16% polymerization, which corresponds to 10.666% polymerization per minute (Experiment 1). Additionally, polymerization of dicyclopentadiene has also been performed with the reaction mixtures being maintained in the dark (wrapped with thin foil). The reaction mixtures were stirred in the dark for 24 h (less than 5% polymerization observed), 3 days (5% polymerization observed) or 7 days (9% polymerization observed). From the last experiments (9% polymerization observed after 7 days), we can estimate the rate of polymerization in the dark to be 9×10−4% polymerization per minute. The ratio between Experiment 2 and 4 (10.6666/9×10−4) gives a krel light/dark of 12,000.

Experimental Procedures and Results:

Polymer Patterning Using Masks

All patterning experiments were run in a glovebox to exclude oxygen and ensure good reproducibility. Importantly, performing the reaction outside the glovebox with no other precautions than flushing the reaction mixture with an argon flow gave identical results.

General Procedures

Dicyclopentadiene 12 as Monomer

In a glovebox, an oven-dried 20 mL scintillation vial was charged with 2,4,6-triphenylpyrylium tetrafluoroborate TPPT (2.0 mg, 5 µmol), $CH_2Cl_2$ (3 mL) and $RuCl_2(CHPh)(IMes)_2$ (0.87 mg, 1 µmol). Dicyclopentadiene (1.32 g, 10 mmol) was then added and the solution was transferred into a BRAND® petri dish (glass, 40 mm×12 mm). The petri dish was placed on the mask and light was shined through the mask for 15 minutes (experimental setup 2). The petri dish was finally removed from the glovebox and the unreacted monomer was thoroughly washed away with dichloromethane to afford the desired patterned poly(dicyclopentadiene).

When the patterning experiments were performed on a bigger scale, the amounts of dicyclopentadiene, catalysts, dichloromethane and the size of the petri dish were adjusted as followed: dicyclopentadiene (7.93 g, 60 mmol), $RuCl_2(CHPh)(IMes)_2$ (5.2 mg, 6 µmol), 2,4,6-triphenylpyrylium tetrafluoroborate TPPT (11.9 mg, 30 µmol) and $CH_2Cl_2$ (26 mL) in a BRAND® petri dish (glass, 80 mm×15 mm). Light was shined for 30 minutes.

Norbornadiene 9 as Monomer

In a glovebox, an oven-dried 20 mL scintillation vial was charged with 2,4,6-triphenylpyrylium tetrafluoroborate TPPT (5.9 mg, 15 µmol), $CH_2Cl_2$ (2.5 mL) and $RuCl_2(CHPh)(IMes)_2$ (6.5 mg, 7.5 µmol). Norbornadiene (1.52 mL, 15 mmol) was then added and the solution was transferred into a BRAND® petri dish (glass, 40 mm×12 mm). The petri dish was placed on the mask and light was shined through the mask for 1 h (experimental setup 2). The petri dish was finally removed from the glovebox and the unreacted monomer was thoroughly washed away with dichloromethane to afford the desired patterned poly(norbornadiene).

1,5-Cyclooctadiene 10 as Monomer

In a glovebox, an oven-dried 20 mL scintillation vial was charged with 2,4,6-triphenylpyrylium tetrafluoroborate TPPT (5.0 mg, 12.5 µmol), $CH_2Cl_2$ (2.5 mL) and $RuCl_2(CHPh)(IMes)_2$ (5.4 mg, 6.25 µmol). 1,5-Cyclooctadiene (1.53 mL, 12.5 mmol) was then added and the solution was transferred into a BRAND® petri dish (glass, 40 mm×12 mm). The petri dish was placed on the mask and light was shined through the mask for 15 minutes (experimental setup 2). The petri dish was finally removed from the glovebox and the unreacted monomer was thoroughly washed away with dichloromethane to afford the desired patterned poly(1,5-cyclooctadiene).

5-Ethylidene-2-Norbornene 11 as Monomer

In a glovebox, an oven-dried 20 mL scintillation vial was charged with 2,4,6-triphenylpyrylium tetrafluoroborate TPPT (4.0 mg, 10 µmol), $CH_2Cl_2$ (2.5 mL) and $RuCl_2(CHPh)(IMes)_2$ (4.3 mg, 5 µmol). 5-Ethylidene-2-norbornene (1.34 mL, 10 mmol) was then added and the solution was transferred into a BRAND® petri dish (glass, 40 mm×12 mm). The petri dish was placed on the mask and light was shined through the mask for 15 minutes (experimental setup 2). The petri dish was finally removed from the glovebox and the unreacted monomer was thoroughly washed away with dichloromethane to afford the desired patterned poly(5-ethylidene-2-norbornene).

The thickness of the patterned polymers can be easily modulated by tuning the time of irradiation, as can be seen on the above picture displaying poly(dicyclopentadiene) patterns obtained after 5 minutes (0.2 mm), 15 minutes (1.6-2.0 mm) and 60 minutes (3.8 mm) of irradiation. All measures were made using an electronic digital micrometer).

Experimental Procedure and Results:

Polymer Patterning using Blue Laser

General Procedure

In a glovebox, an oven-dried 20 mL scintillation vial was charged with 2,4,6-triphenylpyrylium tetrafluoroborate TPPT (2.0 mg, 5 µmol), $CH_2Cl_2$ (3 mL) and $RuCl_2(CHPh)(IMes)_2$ (0.87 mg, 1 µmol). Dicyclopentadiene (1.32 g, 10 mmol) was then added and the solution was transferred into a BRAND® petri dish (glass, 40 mm×12 mm). Irradiation was carried out with a blue laser pointer (450 nm, 200 mW) through a magnifying glass. The support stand holding the laser was then moved either manually over 30-40 minutes or with an orbital shaker for 10 minutes (experimental setup 3). The petri dish was finally removed from the glovebox and unreacted monomer was thoroughly washed away with dichloromethane to afford the desired patterned poly(dicyclopentadiene).

Experimental Procedures and Results:

Photolithographic Applications on Silicon Wafers

The strategy exploited for the photolithographic ring-opening metathesis polymerization of norbornadiene onto silicon wafers is similar to the strategy previously reported by Fourkas and coworkers.[23] First, the functionalization of the silicon oxide layer of the silicon wafers with trichloro(5-norbornen-2-yl)silane was performed in order to attach a norbornene unit at the surface of the wafers. Our standard visible-light-promoted ring opening metathesis polymerization of norbornadiene was then performed on the silicon wafers which covalently bound to the growing polymer thanks to the norbornene unit present at the surface. Removal of the unreacted monomer finally afforded the desired patterned poly(norbornadiene) at the surface of the silicon wafers. See, Scheme 2.

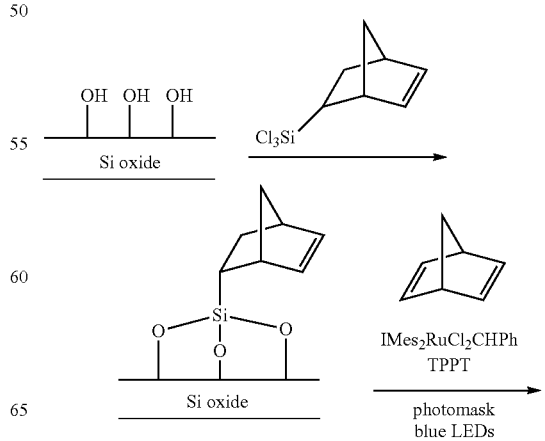

Scheme 2

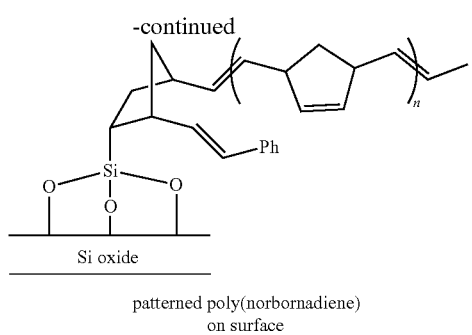

patterned poly(norbornadiene) on surface

Functionalization of Silicon Wafers with Trichloro(5-Nor-bornen-2-Yl)Silane

Silicon wafers were cleaned by sonication in acetone (2×15 minutes) and isopropanol (2×15 minutes), rinsed with isopropanol, dried under a stream of N2 and finally placed in an $O_2$ plasma chamber under vacuum (100 mTorr) using a power of 50 watts for 2 minutes. The silicon wafers were immediately functionalized with trichloro(5-norbornen-2-yl)silane.

In a glovebox, a 60 mL screw-cap jar was charged with 20 mL of a solution of trichloro(5-norbornen-2-yl)silane (0.2 mL) in anhydrous toluene (20 mL). Four to five 1 cm×1 cm silicon wafers with a native silicon oxide layer were added to the solution which was agitated overnight on an orbital shaker at room temperature. The silicon wafers were then thoroughly rinsed with anhydrous toluene, dried under a stream of N2 and stored in a glovebox prior to use.

Angle contact measurements with a water drop were indicative of the successful grafting of the norbornene unit at the silicon wafer surface (34° for a non-functionalized silicon wafer, 85° for a norbornene-functionalized silicon wafer).

Procedure for the photolithographic patterning of norbornene-functionalized silicon wafers In a glovebox, a norbornene-functionalized silicon wafer was placed on a microscope slide (22 mm×22 mm, thickness of 0.13-0.17 mm). Four to five drops of a solution of norbornadiene (305 μL, 3 mmol), $RuCl_2(CHPh)(IMes)_2$ (1.3 mg, 1.5 μmol) and 2,4,6-triphenylpyrylium tetrafluoroborate (1.2 mg, 3 μmol) in $CH_2Cl_2$ (1 mL) were then added to cover the silicon wafer. A second microscope slide (22 mm×22 mm, thickness of 0.13-0.17 mm) was then quickly placed on top of the silicon wafer/solution. The mask was then placed on top of the second microscope slide and light was shined through the mask for 10 minutes. The silicon wafer was developed by pouring it twice into DCM for 1 minute before letting it dry under a steam of N2 to finally afford the desired patterned poly(norbornadiene) film.

REFERENCES FOR EXAMPLE 2

1 Cunico, J. Org. Chem. 1971, 36, 929-932.
2 Jafarpour, Organometallics 2000, 19, 2055-2057.
3 (a) Huang, J. Am. Chem. Soc. 1999, 121, 2674-2678. (b) Bantreil, Nat. Protoc. 2011, 6, 69-77.
4 (a) Sanford, Organometallics 2001, 20, 5314-5318. (b) Conrad, Organometallics 2003, 22, 1986-1988.
5 Kotyk, Organometallics 2009, 28, 5424-5431.
6 Trnka, J. Am. Chem. Soc. 2003, 125, 2546-2558.
7 Tomar, Chem. Commun., 2018, 54, 9753-9756.
8 Ogawa, J. Am. Chem. Soc. 2015, 137, 1400-1403
9 Yao, Q.; Zhang, Y. J. Am. Chem. Soc. 2004, 126, 74-75.
10 Xi, Org. Lett. 2011, 13, 6188-6191.
11 Hongfa, Org. Lett. 2007, 9, 3259-3261.
12 Lipshutz, J. Org. Chem. 2011, 76, 4379-4391.
13 Wu, Org. Chem. 2012, 6777-6784.
14 Broggi, Chem. Eur. J. 2010, 16, 9215-9225.
15 Paz Muñoz, Adv. Synth. Catal. 2010, 352, 2189-2194.
16 Fürstner, A.; Chem. Eur. J. 2001, 7, 3236-3253.
17 Wang, S.-Y.; Ji, S.-J.; Loh, T.-P. J. Am. Chem. Soc. 2007, 129, 276-277.
18 Bunnage, Tetrahedron 1994, 50, 3975-3986.
19 Busqué, F.; Tetrahedron 1995, 51, 1503-1508.
20 Henderson, Org. Lett. 2010, 12, 824-827.
21 Li, Z.; Zhang, Y.; Liu, Z.-Q. Org. Lett. 2012, 14, 74-77.
22 Hata, Org. Lett. 2008, 10, 5031-5033.
23 Harris, Adv. Matter. 2005, 17, 39-42.

Example 3: Synthesis and Activity of Pyrylium Photocatalysts

A number of pyrylium derivatives with different electron-donating and withdrawing groups were prepared. Pyryliums 1 and 2 are commercially available. All pyryliums were previously reported except for pyrylium 18. Pyryliums 1-15 and 19-20 were synthesized according to procedures previously reported and well established. The procedure for the synthesis of pyrylium 18 is described herein. These pyrylium derivatives are as identified in Table 6

TABLE 6

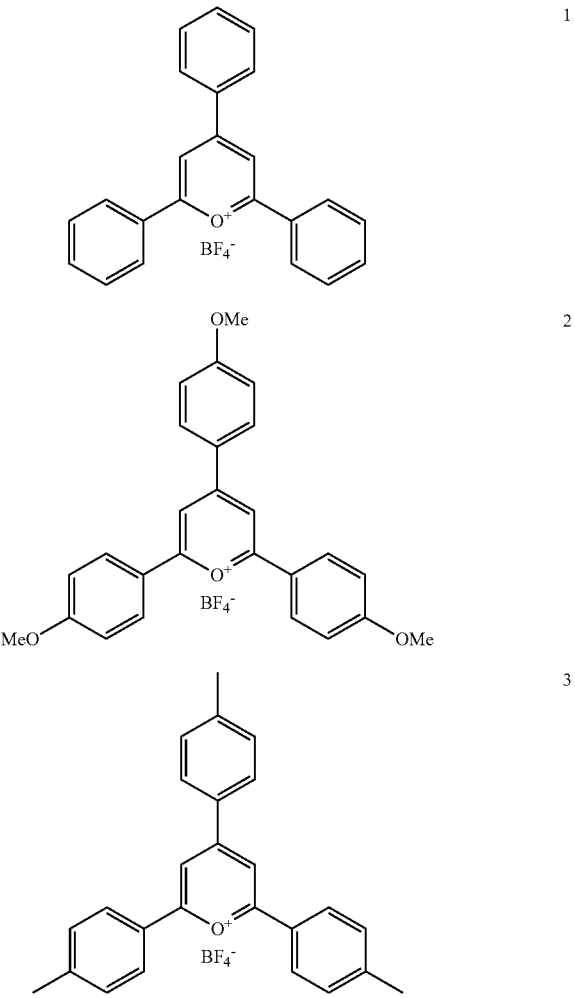

TABLE 6-continued
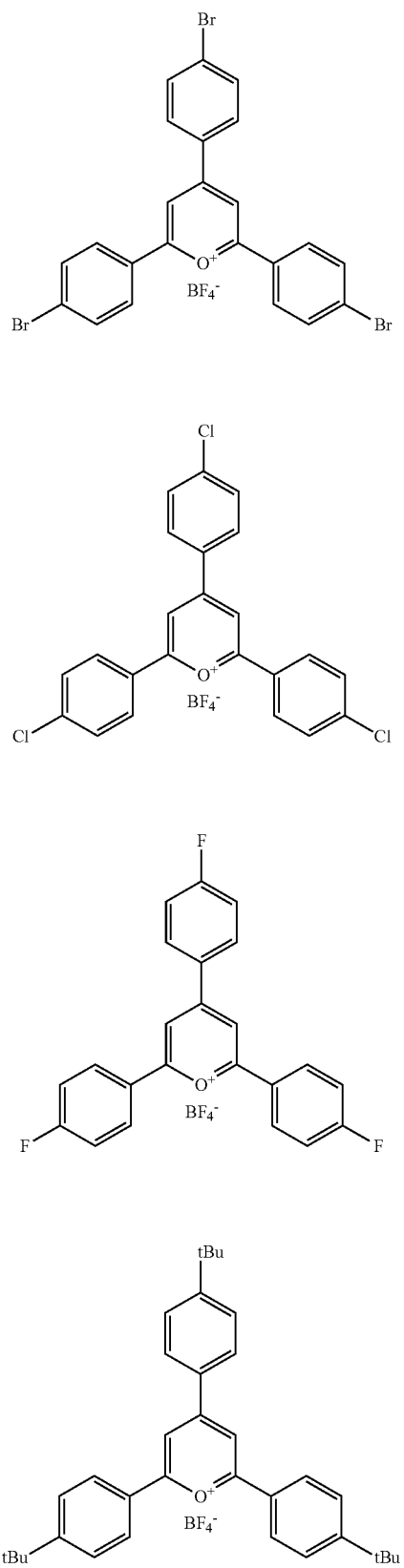
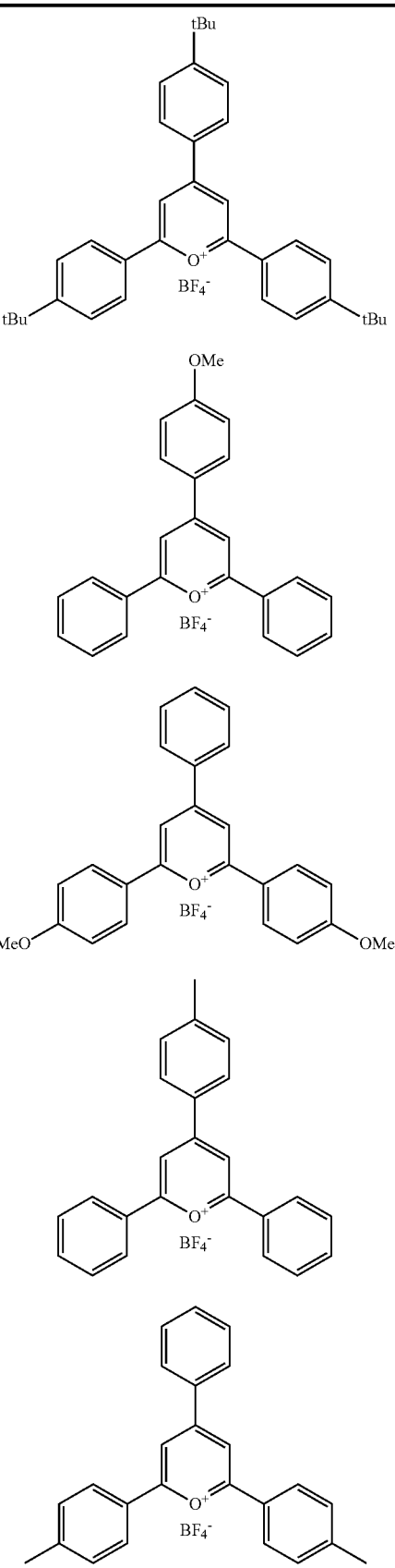

TABLE 6-continued
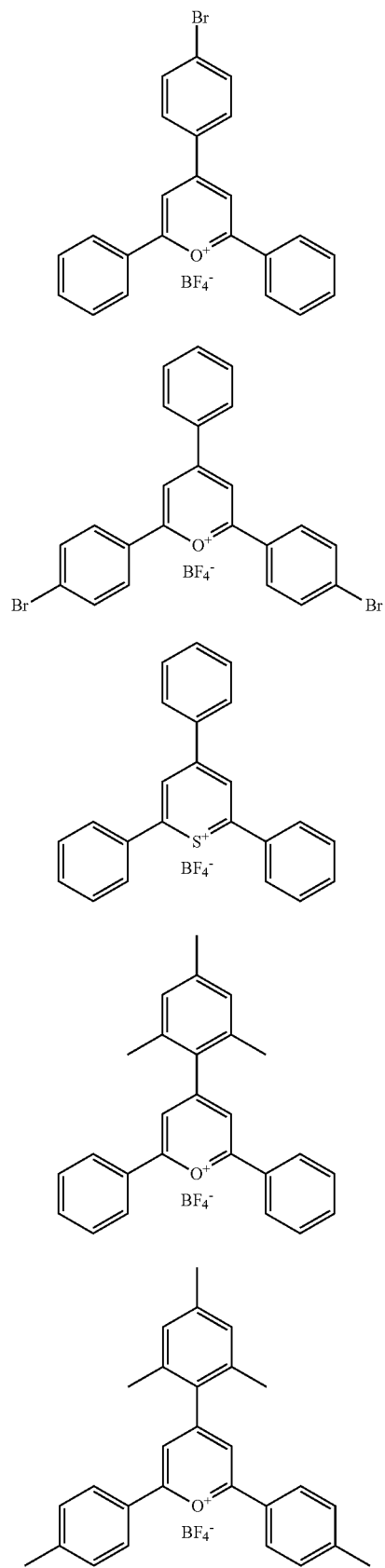
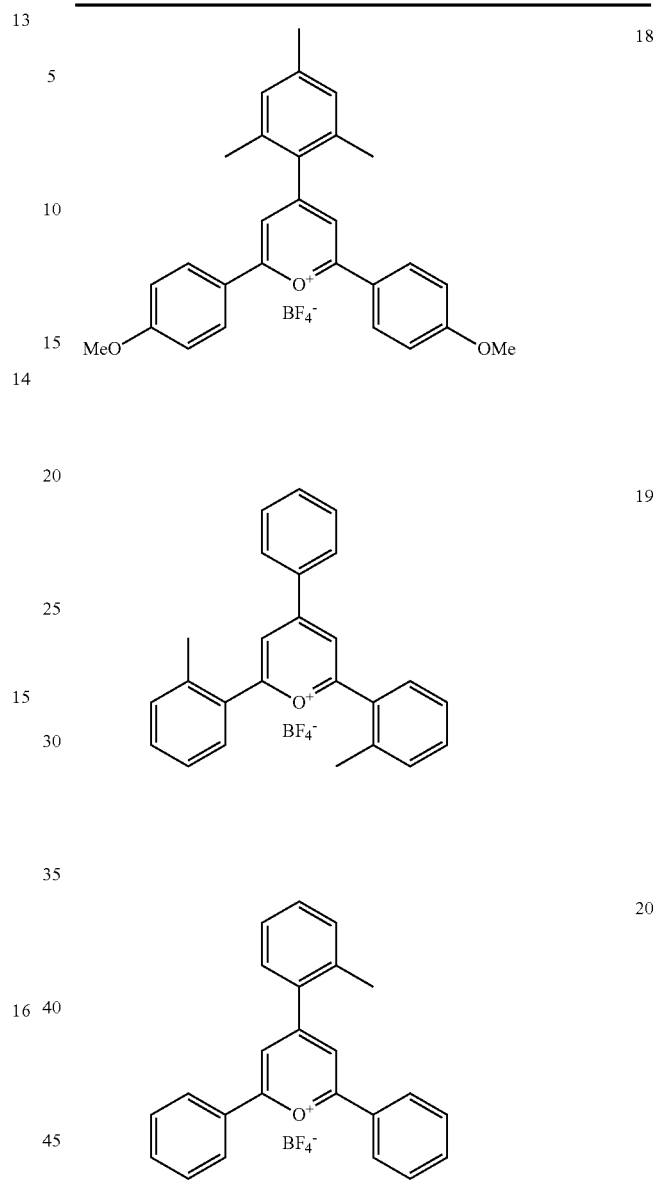
The new pyrylium compounds were used in the ring closing metathesis of diethyl diallylmalonate using (IMes)$_2$RuCl$_2$CHPh. See, Scheme 3 and the yields in Table 7.
Scheme 3
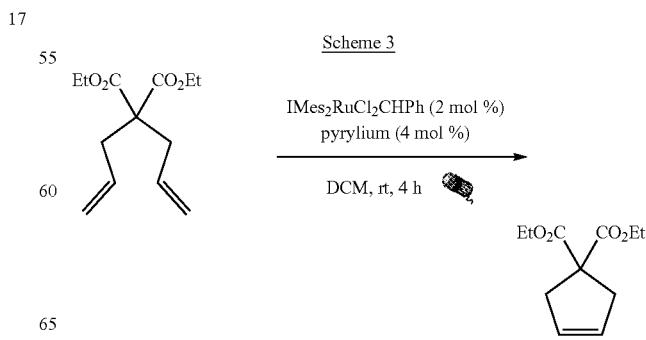

TABLE 7

| Compound | Yield | Compound | Yield |
|---|---|---|---|
| 2,4,6-triphenylpyrylium BF4 | 83 | 2,4,6-tris(4-methoxyphenyl)pyrylium BF4 | 0 |
| 2,4,6-tris(4-methylphenyl)pyrylium BF4 | 28 | 2,4,6-tris(4-bromophenyl)pyrylium BF4 | 83 |
| 2,4,6-tris(4-chlorophenyl)pyrylium BF4 | 85 | 2,4,6-tris(4-fluorophenyl)pyrylium BF4 | 80 |
| 2,4,6-tris(4-tert-butylphenyl)pyrylium BF4 | 19 | 2,4,6-tris(2-methylphenyl)pyrylium BF4 | 83 |

TABLE 7-continued
| Compound | Yield | Compound | Yield |
| --- | --- | --- | --- |
| 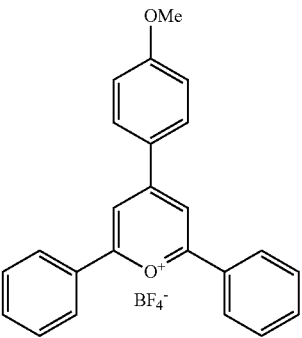 | 3 | 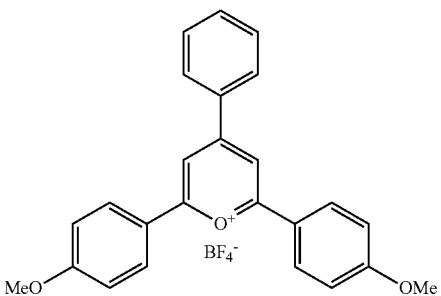 | 2 |
| 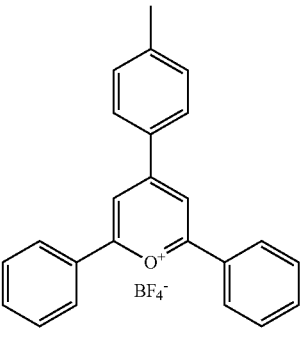 | 80 | 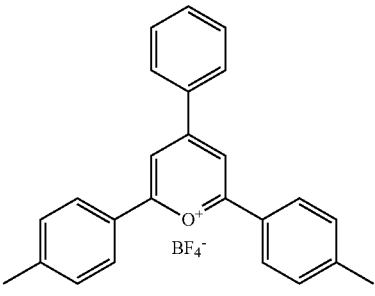 | 32 |
| 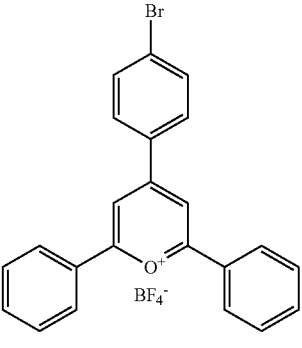 | 83 | 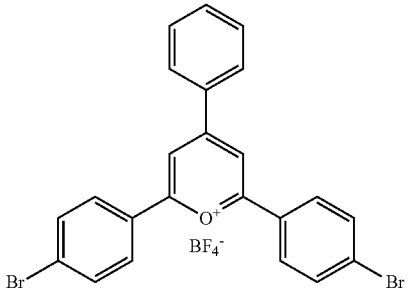 | 84 |
| 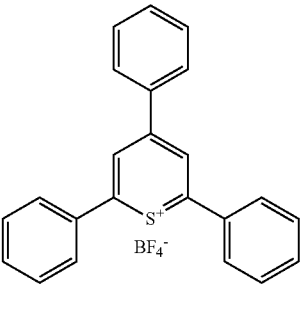 | 82 | 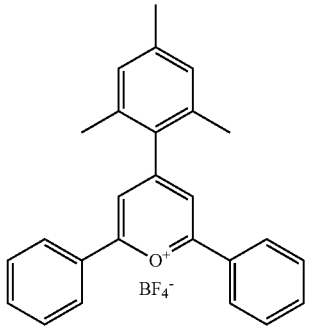 | 48 |

TABLE 7-continued

| Compound | Yield | Compound | Yield |
|---|---|---|---|
| (structure) | 34 | (structure) | 5 |
| (structure) | 82 | (structure) | 80 |

As can be seen, it seems that, compared to TPPT, new pyryliums possessing electron-withdrawing groups and some derivatives possessing slightly electron-donating groups are also efficient to promote the RCM of diethyl diallylmalonate.

The same RCM of diethyl diallylmalonate (Scheme 4) was performed with the photoredox catalysts using TPPT and those in Table 8.

TABLE 8

PC$_1$

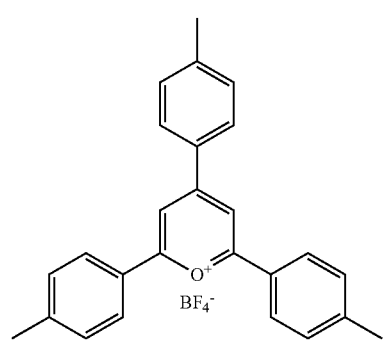

TABLE 8-continued

PC$_2$

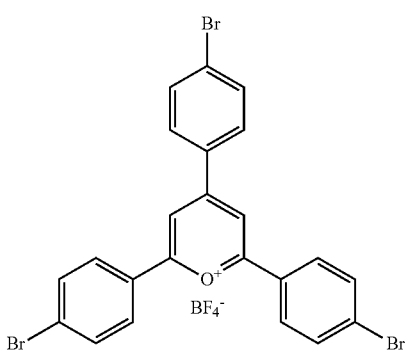

PC$_3$

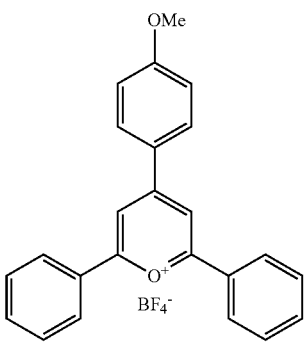

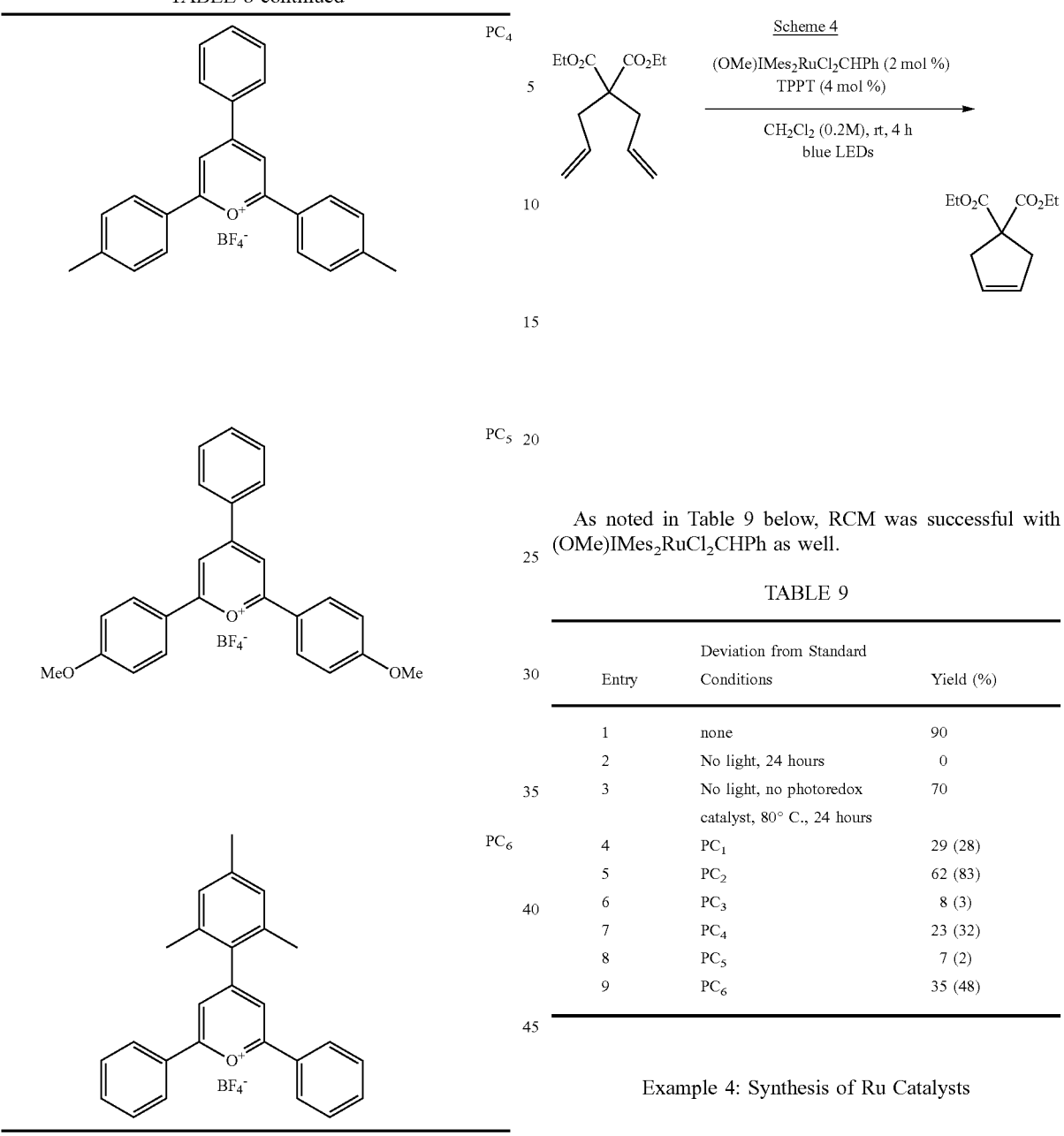
As noted in Table 9 below, RCM was successful with (OMe)IMes$_2$RuCl$_2$CHPh as well.
TABLE 9
| Entry | Deviation from Standard Conditions | Yield (%) |
|---|---|---|
| 1 | none | 90 |
| 2 | No light, 24 hours | 0 |
| 3 | No light, no photoredox catalyst, 80° C., 24 hours | 70 |
| 4 | PC$_1$ | 29 (28) |
| 5 | PC$_2$ | 62 (83) |
| 6 | PC$_3$ | 8 (3) |
| 7 | PC$_4$ | 23 (32) |
| 8 | PC$_5$ | 7 (2) |
| 9 | PC$_6$ | 35 (48) |
Example 4: Synthesis of Ru Catalysts
A. Synthesis of (OMe)IMes$_2$RuCl$_2$CHPh
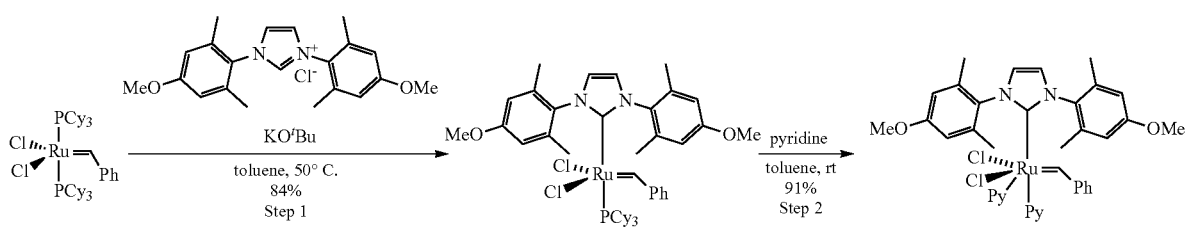

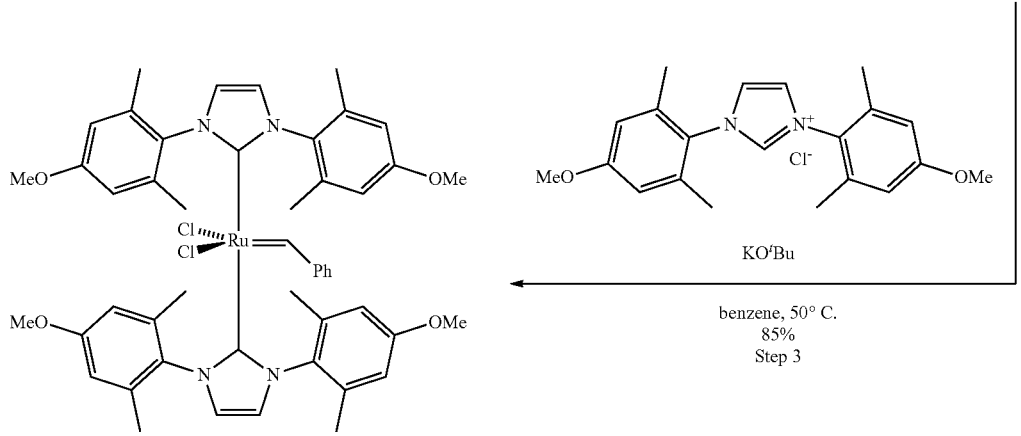

Step 1: In a glovebox, a 25 mL round bottom flask was charged with Grubbs 1st generation (206 g, 0.25 mmol), (OMe)IMes.HCl (140 mg, 0.375 mmol), KO$^t$Bu (42 mg, 0.375 mmol) and anhydrous toluene (10 mL). The flask was sealed and removed from the glovebox before stirring at 50° C. for 2 h. The reaction mixture was cooled to room temperature and concentrated under vacuum. The crude residue was finally washed with water and a minimal amount of hexane before being dried under vacuum to afford the desired (OMe)IMesRu(PCy$_3$)Cl$_2$CHPh as a purple-brown solid (185 mg, 0.210 mmol, 84% yield).

Step 2: In a glovebox, (OMe)IMesRu(PCy$_3$)Cl$_2$CHPh (185 mg, 0.210 mmol) was dissolved in anhydrous toluene (680 μL) and pyridine (1.35 mL). The reaction mixture was stirred for 30 min at room temperature. During that time, a quick change in color from red to green could be observed. The reaction mixture was then concentrated under vacuum before pentane was added. The green residue was triturated in pentane and allowed to precipitate for 30 minutes at −20° C. The precipitate was then filtered, washed with cold pentane (−20° C.) and finally dried under vacuum to afford (OMe)IMesRu(Py$_2$)Cl$_2$CHPh as a green solid (145 mg, 0.192 mmol, 91% yield).

Step 3: In a glovebox, a 5 mL round bottom flask was charged with (OMe)IMes.HCl (52 mg, 0.138 mmol), KOtBu (16 mg, 0.138 mmol) and anhydrous benzene (2.5 mL). The reaction mixture was stirred for 45 min at room temperature in the glovebox before addition of (OMe)IMesRu(Py$_2$)Cl$_2$CHPh (105 mg, 0.138 mmol). The brown reaction mixture was then stirred at 45° C. for 6 h and concentrated under vacuum. The crude residue was finally washed with water and a minimal amount of hexane before being dried under vacuum to afford the desired (OMe)IMes$_2$RuCl$_2$CHPh as a brown solid (110 mg, 0.118 mmol, 85% yield).

B. Synthesis of (OMe)SIMes$_2$RuCl$_2$CHPh

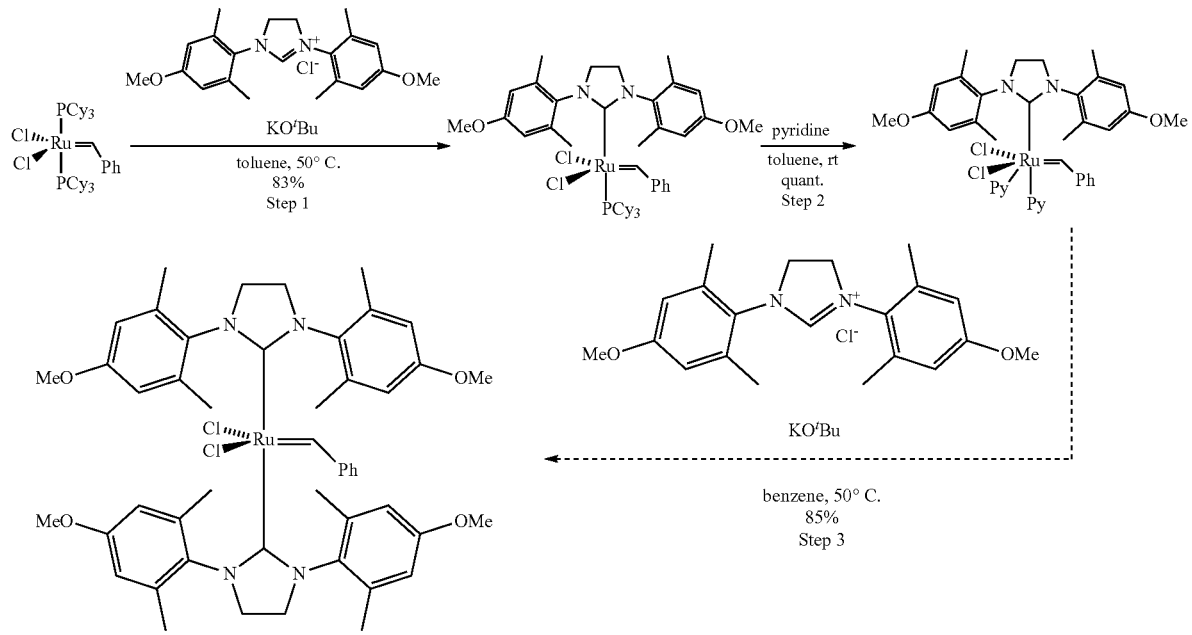

Step 1: In a glovebox, a 25 mL round bottom flask was charged with Grubbs 1st generation (206 g, 0.25 mmol), (OMe)SIMes.HCl (187 mg, 0.5 mmol), KO$^t$Bu (56 mg, 0.5 mmol) and anhydrous toluene (10 mL). The flask was sealed and removed from the glovebox before stirring at 50° C. for 2 h. The reaction mixture was cooled to room temperature and concentrated under vacuum. The crude residue was dissolved in dichloromethane, washed with water and concentrated under vacuum. The crude residue was finally crystallized in hexane, filtered, washed with a minimal amount of hexane and dried under high vacuum to afford the desired (OMe)SIMesRu(PCy$_3$)Cl$_2$CHPh as a red-pink solid (184 mg, 0.209 mmol, 83% yield).

Step 2: In a glovebox, (OMe)SIMesRu(PCy$_3$)Cl$_2$CHPh (180 mg, 0.204 mmol) was dissolved in anhydrous toluene (500 µL) and pyridine (1.32 mL). The reaction mixture was stirred for 30 min at room temperature. During that time, a quick change in color from red to green could be observed. The reaction mixture was then concentrated under vacuum before pentane was added. The green residue was triturated in pentane and allowed to precipitate for 30 minutes at −20° C. The precipitate was then filtered, washed with cold pentane (−20° C.) and finally dried under vacuum to afford (OMe)SIMesRu(Py$_2$)Cl$_2$CHPh as a green solid (155 mg, 0.204 mmol, quant. yield).

Step 3: The synthesis of (OMe)SIMes$_2$RuCl$_2$CHPh from 38 mg (0.05 mmol) of (OMe)SIMesRu(PCy$_3$)Cl$_2$CHPh proceeds using the same conditions used for the synthesis of the corresponding (OMe)IMes$_2$RuCl$_2$CHPh.

Example 5: Comparative Studies

A. Studies Lacking Light, Photoredox Catalyst, or Ruthenium Catalyst

A series of control experiments was conducted to determine the importance of light, photoredox catalyst, and ruthenium catalyst. As a first set of experiments using IMes$_2$RuCl$_2$CHPH, the RCM of diethyl diallylmalonate was performed in the absence of light, absence of ruthenium catalyst, and absence of light. See, Scheme 5.

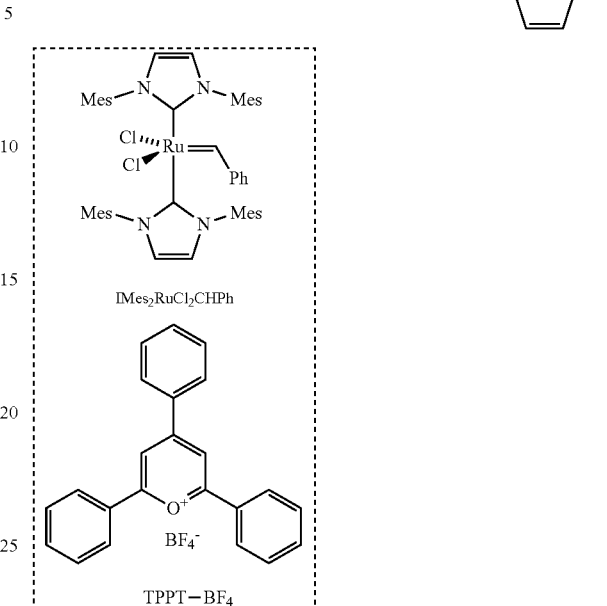

These results show that there is no reaction in the absence of photocatalyst at room temperature, light, or ruthenium catalyst. As such, the same experiments were performed using SIMes$_2$RuCl$_2$CHPh. See, Scheme 6.

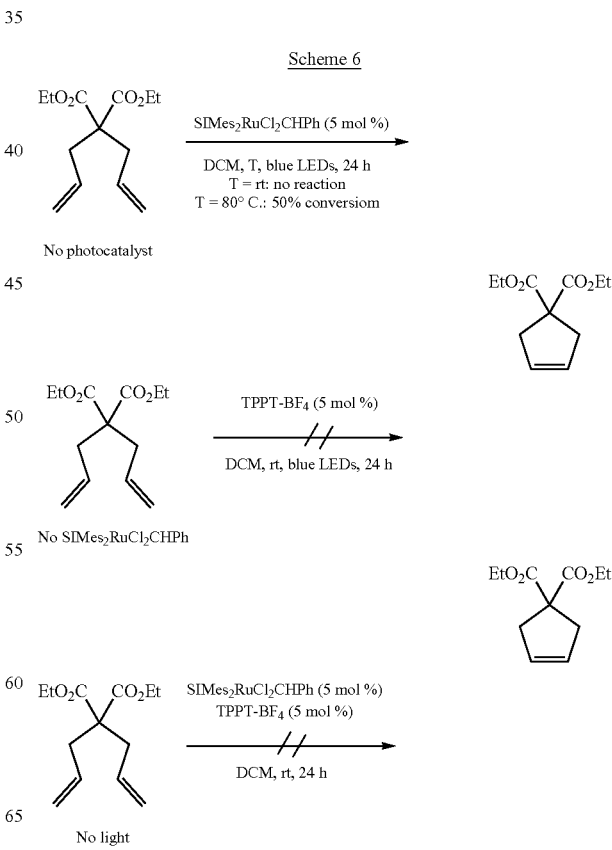

-continued

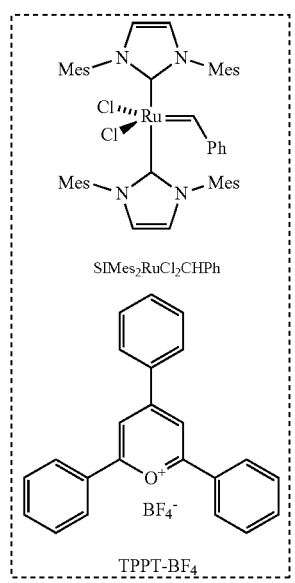

These results also show that there is no reaction in the absence of photocatalyst at room temperature, light, or ruthenium catalyst.

B. Organic Oxidants

In an effort to probe the importance of the photoredox catalyst, the RCM of diethyl diallylmalonate was performed using TCNE (tetracyanoethylene) or ferrocenium. See, Scheme 7.

Scheme 7

As shown in Table 10, ferrocenium resulted in a moderate yield, only in the presence of light.

TABLE 10

| Oxidant | Dark/light | Yield (%) |
|---|---|---|
| TCNE (10 mol %) | Dark | 0 |
| TCNE (10 mol %) | Light | 0 |
| $Cp_2FePF_6$ (10 mol %) | Dark | 0 |
| $Cp_2FePF_6$ (1 equiv.) | Dark | 0 |
| Cp2FePF6 (10 mol %) | Light | 39 |

C. Sub-Stoichiometric Experiments

Experiments were run in an effort to determine the impact of sub-stoichiometric amounts of various norbornene substituted reagents 1-5 and using 25 mol % of the ruthenium catalyst and 50 mol % of the photoredox catalyst. See, Scheme 8.

Scheme 8 tetramer or polymer

1

2

3

4

5

These results showed that monomers 1 and 2 (exo, exo) only showed one benzylidene peak corresponding to the starting $IMes_2Ru$ complex (no other signals) and the two monomers were consumed within an hour. The use of norbornene 3 and 25 mol % of Ru led to instantaneous polymerization. Further, monomers 4 and 5 (endo, endo) were not consumed using 25 mol % of Ru even after 4 hours.

Example 6: Reaction Optimization Studies

A. Concentration and Reaction Time Effects (i) Experiment #1

The influence of concentration and reaction time on the RCM of diethyl diallylmalonate using 5 mol % of ruthenium catalyst and 5 mol % of photoredox catalyst was analyzed. See, Scheme 9.

Scheme 9

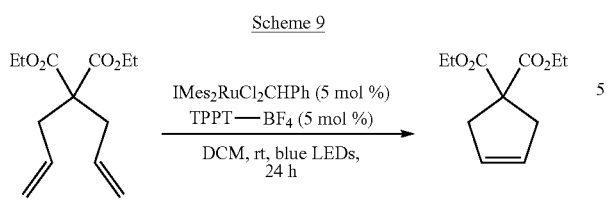

| Concentration | Yield (conv.) |
|---|---|
| 0.05M | 62% (73%) |
| 0.075M | 56% (64%) |
| 0.1M | 82% (>99%) |
| 0.2M | 73% (83%) |

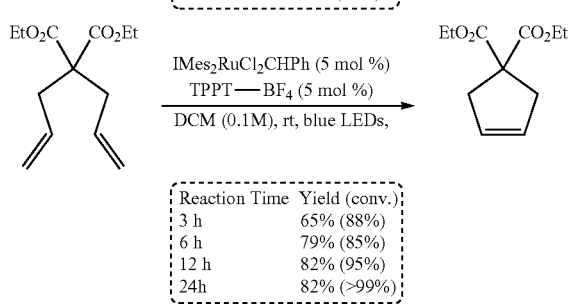

| Reaction Time | Yield (conv.) |
|---|---|
| 3 h | 65% (88%) |
| 6 h | 79% (85%) |
| 12 h | 82% (95%) |
| 24h | 82% (>99%) |

These results illustrate that although 0.1 M is an optimal concentration, a concentration of 0.2 M gives an acceptable yield. In addition, the reaction seems to be done after 6 hours.

(ii) Experiment #2

For these experiments, 5 mol % of the ruthenium catalyst and 7.5 mol % of the photoredox catalyst were used to study the influence of the concentration and reaction time on the RCM of diethyl diallylmalonate. See, Scheme 10.

Scheme 10

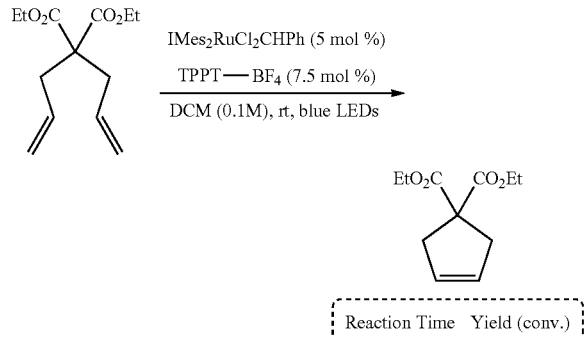

| Reaction Time | Yield (conv.) |
|---|---|
| 3 h | 90% (>99%) |
| 12 h | 82% (>99%) |
| 24 h | 80% (>99%) |

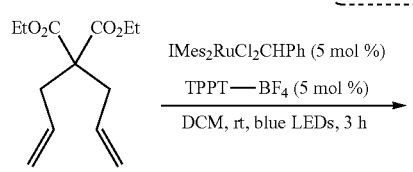

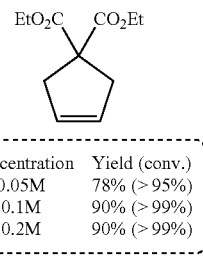

| Concentration | Yield (conv.) |
|---|---|
| 0.05M | 78% (>95%) |
| 0.1M | 90% (>99%) |
| 0.2M | 90% (>99%) |

These results illustrate that the reaction is complete in minimal time and that concentrations of 0.1 M and 0.2M are both efficient.

(iii) Experiment #3

The RCM of diethyl diallylmalonate was performed using slight amounts of metathesis catalysts (0.1 and 0.05 mol %). See, Scheme 11.

Scheme 11

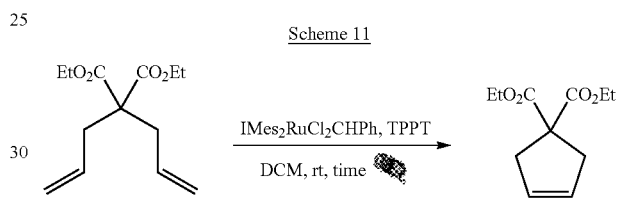

Table 11 illustrates that the conversion and yields were equal and ranged from 8 to 33%.

TABLE 11

| Ru (mol %) | TPPT (mol %) | Time (h) | Yield (%) |
|---|---|---|---|
| 0.1 | 0.2 | 4 | 29 |
| 0.1 | 0.2 | 20 | 33 |
| 0.05 | 0.1 | 4 | 8 |

B. Catalyst Loadings

(i) Experiment #1

These experiments were performed to study the influence of the catalysts loadings on the reaction. See, Scheme 12.

Scheme 12

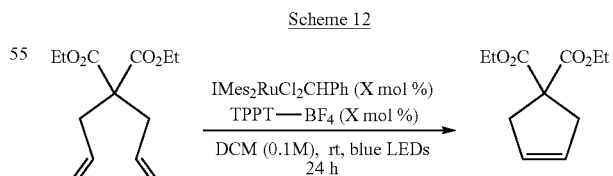

These results illustrate that the use of 5 mol % of Ru and 7.5 mol % of photoredox catalyst was optimal. However, reducing the amounts of catalysts to 2 mol % of each or to 5 mol % of Ru and 2 mol % of PC still resulted in fair amounts of product.

TABLE 12

| Ru/Photoredox Catalyst Loading (mol %) | Yield (conv.) |
|---|---|
| 5/5 | 82%/(>99%) |
| 2/2 | 14% (43%) |
| 2.5/5 | 67%/(>99%) |
| 5/2 | 9% (17%) |
| 5.75 | 82%/(>99%) |
| 5/10 | 50%/(>99%) |

(ii) Experiment #2

Additional experiments were performed, reducing the catalysts loadings. Scheme 13.c Scheme 13

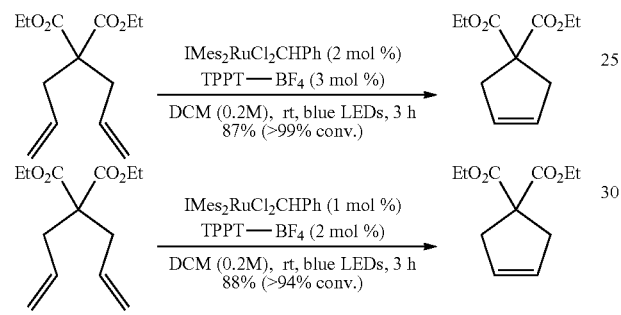

In summary, the use of 2 mol % of Ru and 3 mol % of PC is as efficient as the use of 5 mol % of Ru and 7.5 mol % of PC providing that the concentration is increased to 0.2 M.

Example 7: Photocatalysts Screening

Several photocatalysts were used in the RCM of diethyl diallylmalonate. See, Scheme 14.

Scheme 14

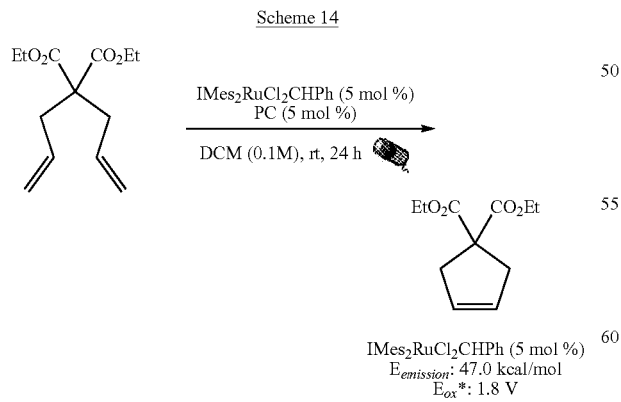

The following catalysts have triplet state of similar energy to the Ru catalyst, as well as to the TPPT photocatalyst (53 kcal).

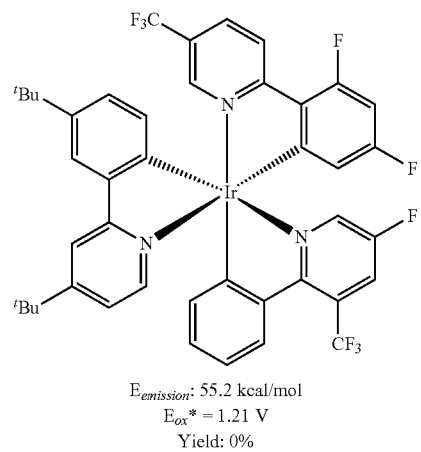

$E_{emission}$: 55.2 kcal/mol
$E_{ox}^*$ = 1.21 V
Yield: 0%

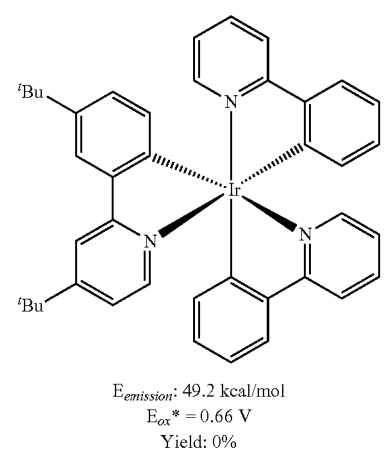

$E_{emission}$: 49.2 kcal/mol
$E_{ox}^*$ = 0.66 V
Yield: 0%

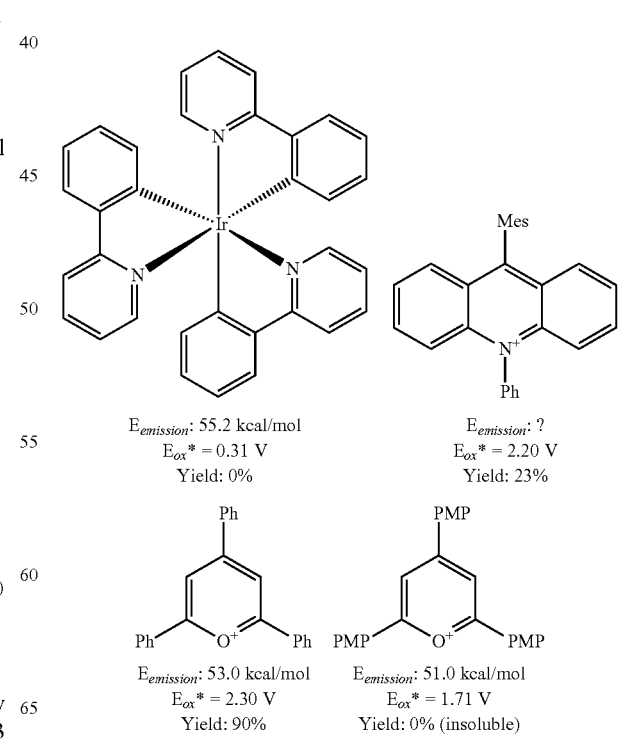

$E_{emission}$: 55.2 kcal/mol
$E_{ox}^*$ = 0.31 V
Yield: 0%

$E_{emission}$: ?
$E_{ox}^*$ = 2.20 V
Yield: 23%

$E_{emission}$: 53.0 kcal/mol
$E_{ox}^*$ = 2.30 V
Yield: 90%

$E_{emission}$: 51.0 kcal/mol
$E_{ox}^*$ = 1.71 V
Yield: 0% (insoluble)

-continued

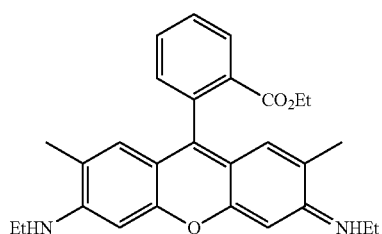

Rhodamine 6G
$E_{emission}$: 48.2 kcal/mol
$E_{ox}^* = 0.95$ V
Yield: 0%

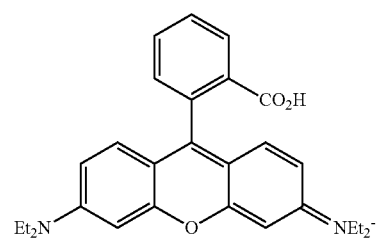

Rhodamine B
$E_{emission}$: 41.5 kcal/mol
$E_{ox}^* = 0.84$ V
Yield: 0%

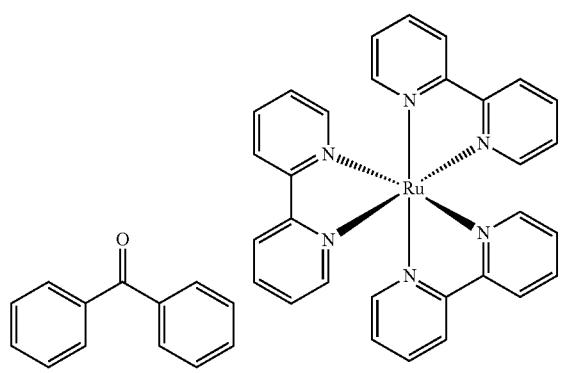

$E_{emission}$: 69.2 kcal/mol
$E_{ox}^* = 1.28$ V
Yield: 0%

$E_{emission}$: 46.5 kcal/mol
$E_{ox}^* = 0.77$ V
Yield: 0%

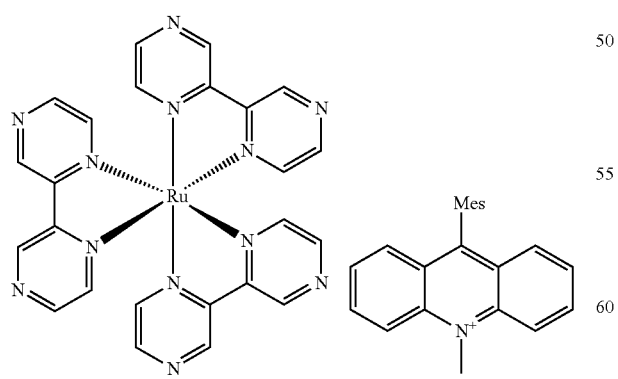

$E_{emission}$: 48.4 kcal/mol
$E_{ox}^* = 1.45$ V
Yield: 0%

$E_{emission}$: 50.2 kcal/mol
$E_{ox}^* = 2.06$ V
Yield: 34%

-continued

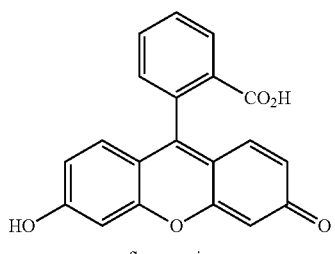

fluorescein
$E_{emission}$: 44.7 kcal/mol
$E_{ox}^* = 0.78$ V
Yield: 0%

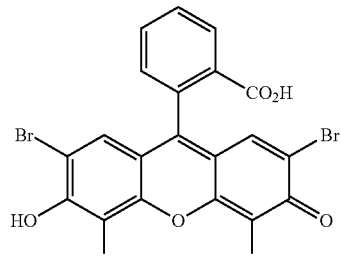

Eosin Y
$E_{emission}$: 44.0 kcal/mol
$E_{ox}^* = 0.79$ V
Yield: 0%

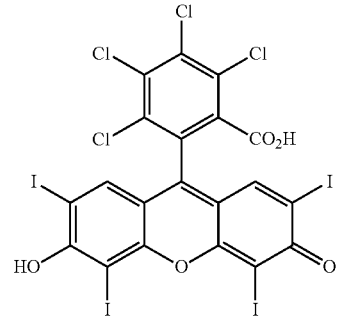

Rose Bengal
$E_{emission}$: 41.5 kcal/mol
$E_{ox}^* = 0.81$ V
Yield: 0%

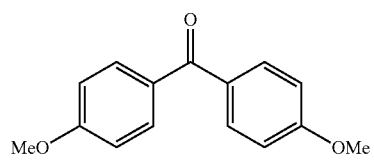

$E_{emission}$: ?
$E_{ox}^* = ?$
Yield: 0%

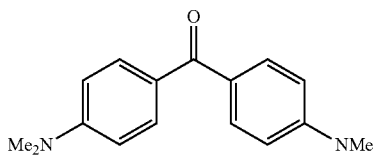

$E_{emission}$: 62.3 kcal/mol
$E_{ox}^* = 0.48$ V
Yield: 0%

-continued

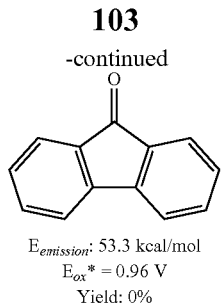

$E_{emission}$: 53.3 kcal/mol
$E_{ox}$* = 0.96 V
Yield: 0%

Although some of these photocatalysts have triplet state energies very close to the energy of the Ru catalyst, none of the photoredox catalysts aside from pyrylium or acridinium photocatalysts are capable of promoting metathesis.

Example 8: ROMP Using a Mask (i) Test #1
ROMP was performed using a mask and norbornadiene as the monomer. Specifically, the reaction was performed using 0.05 mol % of Ru and 0.1 mol % of TPPT during 1 h at high concentration in DCM (6M).

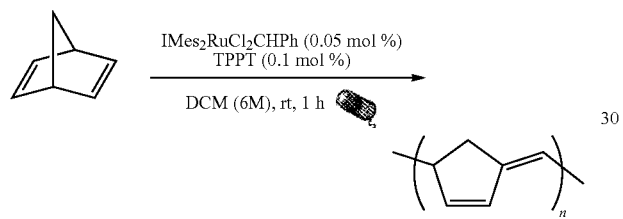

Figure 26A:
FIGS. 26A-26B are photographs of the ROMP of norbornadiene with a foil mask.
Figure 26B:
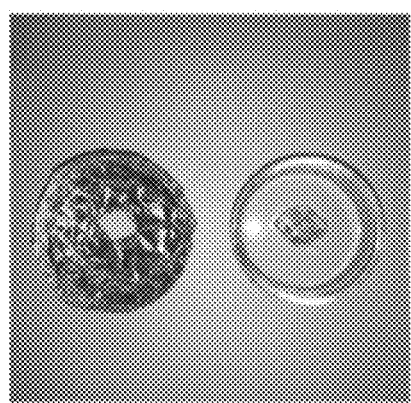
Figure 27A:
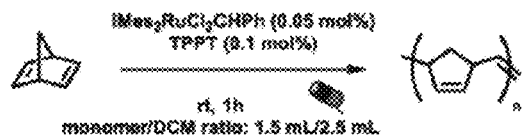
FIGS. 27A-27D are photographs of the ROMP of norbornadiene (FIG. 27A), COD (FIG. 27B), 5-ethylidene-2-norbornene (FIG. 27C), and dicyclopentadiene (FIG. 27D), using a black paper mask. Photographs on the left are immediately after irradiation and photographs on the right are 5 hours after irradiation.
Figure 27A:
Figure 27B:
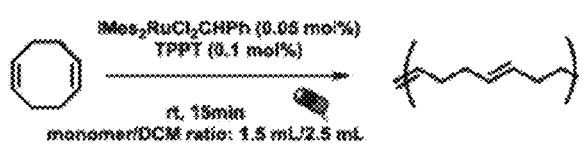
Figure 27B:
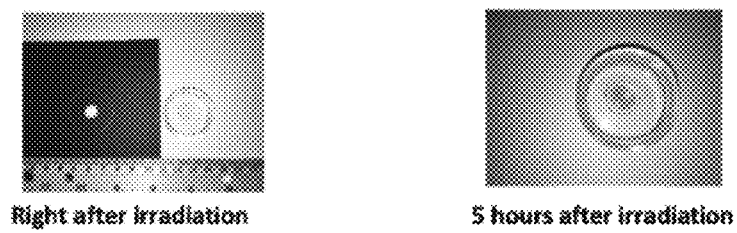
Figure 27C:
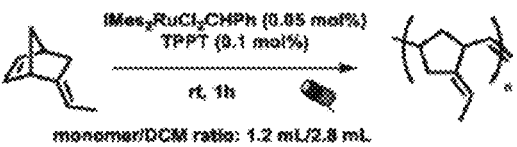
Figure 27C:
Figure 27D:
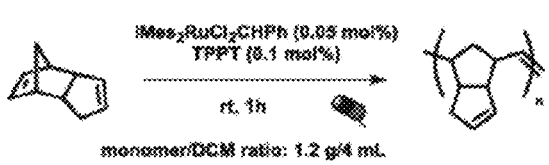
Figure 27D:

In these conditions, the ROMP using a mask furnishes the corresponding polymer with the desired special pattern and reduced side-polymerization in the dark areas. See, FIG. 26.

Test #2
These experiments were performed as described above, but in a glovebox, using norbornadiene, 1,5-cyclooctadiene (COD), 5-ethylidene-2-norbornene, N-methyl-5-norbornene-2,3-dicarboximide, and dicyclopentadiene, respectively, and black paper as the mask. While norbornadiene, 1,5-cyclooctadiene (COD) and 5-ethylidene-2-norbornene provided the desired pattern, N-methyl-5-norbornene-2,3-dicarboximide did not. See, FIG. 27.

Test #3
Additional patterns were generated using 0.05 mol % of Ru with dicyclopentadiene, as well as 5-ethylidene-2-norbornene, as the monomers. As shown in FIG. 28, the Columbia crown could be obtained with varying efficiencies using 5-ethylidene-2-norbornene and dicyclopentadiene.

(iv) Test #4
More complex patterns were prepared in a sequential fashion. The procedure was performed by 1) creating a first pattern using a first mask, 2) developing the pattern by washing with DCM, 3) creating a second pattern using a second mask, and 4) developing the final combined pattern by washing with DCM. To make the distinction between the two different sub-pattern, the solution of the first polymerization was dyed. See, FIG. 29.

Example 9: ROMP with a Laser Pointer

These experiments were performed to induce metathesis using blue-light laser pointers instead of Kessil lamps. Although the RCM of diethyl diallylmalonate using the laser pointer was unsuccessful, the ROMP of dicyclopentadiene was successful. Polymerization occurred in 15-20 seconds. See. FIG. 30.

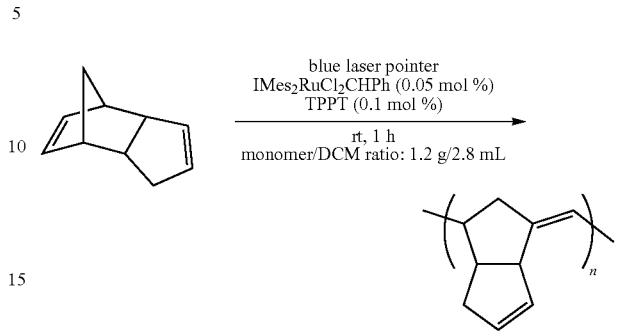

Example 10: Synthesis of Photoredox Catalyst

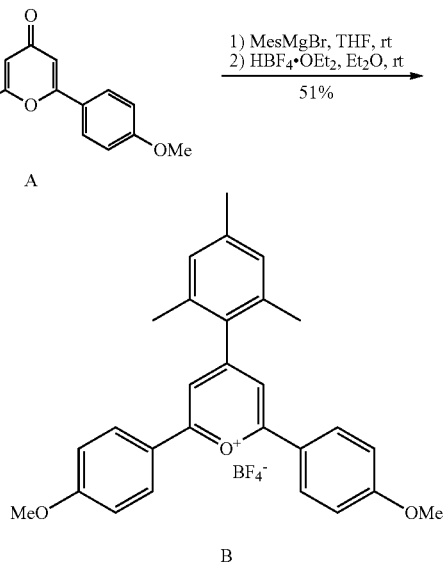

The preparation of pyrylium B is based on a procedure reported in the literature. See, Org. Lett. 2017, 19, 2989. In a flame dried 250 mL round bottom flask, known pyran-4-one A (1.36 g, 4.42 mmol) was dissolved in 120 mL of anhydrous THF under argon before addition of a solution of 2-mesitylmagnesium bromide (1M in THF, 23 mL, 23 mmol) dropwise at room temperature. The reaction mixture was stirred at room temperature overnight, quenched with saturated aqueous solution of $NH_4C_1$ and 10% HCl (1:1 mixture), extracted with dichloromethane, washed with brine, dried over magnesium sulfate, filtered and concentrated under high vacuum. The crude residue was dissolved in anhydrous diethyl ether (50 mL) and $HBF_4.Et_2O$ complex (730 μL, 5.3 mmol) was added dropwise leading to precipitation of a red solid. After stirring for 30 minutes to allow complete precipitation, the precipitate was finally collected by filtration through a glass frit, washed with diethyl ether and dried under high vacuum to afford the desired pyrylium B as a red solid (51%, 1.11 g, 2.21 mmol).

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document and the references cited therein are hereby incorporated herein by reference, each in its entirety, for all purposes.

What is claimed is:

1. A composition for metathesizing a first alkenyl or alkynyl group with a second alkenyl or alkynyl group, comprising:
   (i) a ruthenium metathesis catalyst that is (SIMes)$_2$RuCl$_2$CHPh or (IMes)$_2$RuCl$_2$CHPh:

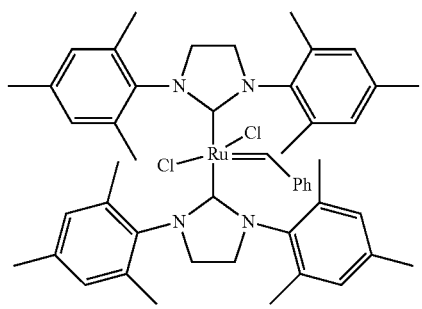

(SIMes)$_2$RuCl$_2$CHPh

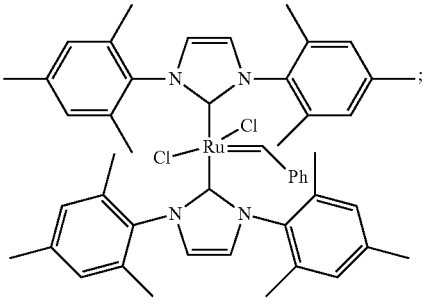

(IMes)$_2$RuCl$_2$CHPh and
   (ii) a photoredox catalyst that is: Ferrocenium hexafluorophosphate,

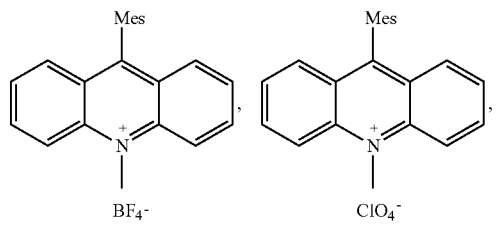

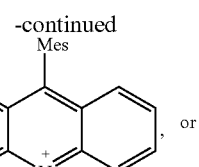

, or

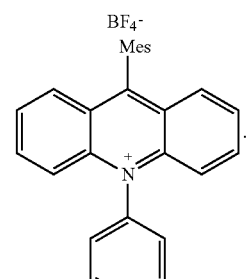

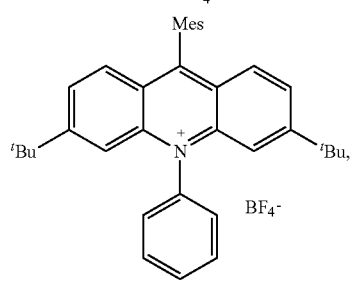

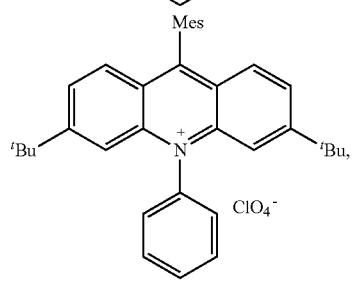

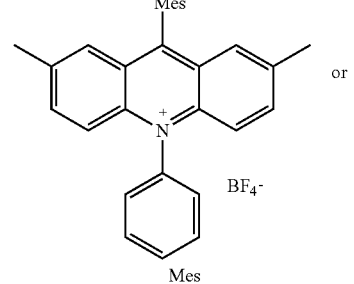

, or

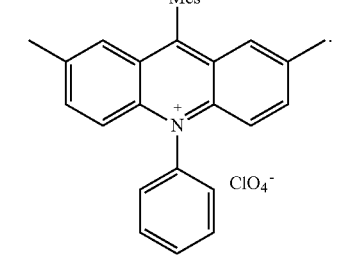

2. The composition of claim 1, wherein the photoredox catalyst is activated by visible light at a wavelength of about 350 nm to about 750 nm.

3. The composition of claim 1, wherein the ruthenium metathesis catalyst is (SIMes)₂RuCl₂CHPh.

4. The composition of claim 1, wherein the ruthenium metathesis complex is (IMes)₂RuCl₂CHPh.

5. The composition of claim 1, wherein the photoredox catalyst is ferrocenium hexafluorophosphate.

6. The composition of claim 1, wherein the photoredox catalyst is

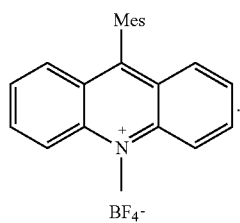

7. The composition of claim 1, wherein the photoredox catalyst is

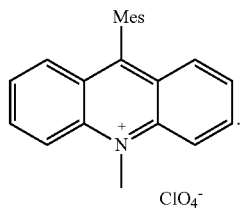

8. The composition of claim 1, wherein the photoredox catalyst is

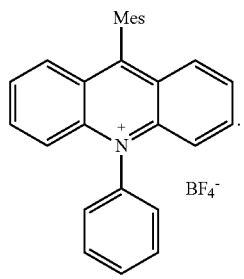

9. The composition of claim 1, wherein the photoredox catalyst is

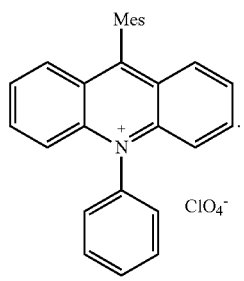

10. A method for chemical metathesis, comprising applying visible light to the composition of claim 1 in the presence of a ruthenium metathesis catalyst and a photoredox catalyst that is activated by visible light.

11. The method of claim 10, wherein the visible light has a wavelength of about 350 nm to about 750 nm.

12. The method of claim 10, that is performed at a temperature of about 20 to about 30° C.

13. The method of claim 10, comprising about 0.01 to about 10 mol %, based on the mol % of the one compound or first and second compound, of the ruthenium metathesis catalyst.

14. The method of claim 10, wherein the concentration of the one compound or first and second compound is about 0.01 to about 5 M.

* * * * *